US 8,293,911 B2

(12) United States Patent
Vernier et al.

(10) Patent No.: US 8,293,911 B2
(45) Date of Patent: *Oct. 23, 2012

(54) DERIVATIVES OF 4-(N-AZACYCLOALKYL) ANILIDES AS POTASSIUM CHANNEL MODULATORS

(75) Inventors: Jean-Michel Vernier, Laguna Niguel, CA (US); Martha Alicia De La Rosa, San Diego, CA (US); Huanming Chen, Irvine, CA (US); Jim Zhen Wu, Aliso Viejo, CA (US); Gary Lee Larson, Cypress, CA (US); Ian Wayne Cheney, Mission Viejo, CA (US)

(73) Assignee: Valeant Pharmaceuticals International, Aliso Viejo, CA (US)

( * ) Notice: Subject to any disclaimer, the term of this patent is extended or adjusted under 35 U.S.C. 154(b) by 283 days.

This patent is subject to a terminal disclaimer.

(21) Appl. No.: 11/894,877

(22) Filed: Aug. 22, 2007

(65) Prior Publication Data

US 2008/0139610 A1    Jun. 12, 2008

Related U.S. Application Data

(60) Provisional application No. 60/839,941, filed on Aug. 23, 2006.

(51) Int. Cl.
*C07D 217/02* (2006.01)
*C07D 217/22* (2006.01)
*A61K 31/472* (2006.01)

(52) U.S. Cl. ......... 546/144; 514/307; 514/309; 546/141

(58) Field of Classification Search .................. None
See application file for complete search history.

(56) References Cited

U.S. PATENT DOCUMENTS

| | | | |
|---|---|---|---|
| 4,181,803 A | 1/1980 | Morita et al. |
| 4,554,281 A | 11/1985 | vonBebenburg et al. |
| 4,668,684 A | 5/1987 | Tibes et al. |
| 4,778,799 A | 10/1988 | Tibes et al. |
| 4,923,974 A | 5/1990 | Ueda et al. |
| 5,032,591 A | 7/1991 | Evans et al. |
| 5,162,346 A | 11/1992 | Lobisch et al. |
| 5,234,947 A | 8/1993 | Cherksey |
| 5,262,419 A | 11/1993 | Aberg et al. |
| 5,284,861 A | 2/1994 | Lobisch et al. |
| 5,384,330 A | 1/1995 | Dieter et al. |
| 5,428,039 A | 6/1995 | Cohen |
| 5,502,058 A | 3/1996 | Mayer et al. |
| 5,643,921 A | 7/1997 | Grover |
| 5,679,706 A | 10/1997 | D'Alonzo et al. |
| 5,760,007 A | 6/1998 | Shank |
| 5,800,385 A | 9/1998 | Demopulos et al. |
| 5,849,789 A | 12/1998 | Rostock et al. |
| 5,852,053 A | 12/1998 | Rostock et al. |
| 5,858,017 A | 1/1999 | Demopulos et al. |
| 5,860,950 A | 1/1999 | Demopulos et al. |
| 5,914,425 A | 6/1999 | Meisel et al. |
| 5,925,634 A | 7/1999 | Olney |
| 6,117,900 A | 9/2000 | Rundfeldt et al. |
| 6,211,171 B1 | 4/2001 | Sawynok et al. |
| 6,218,411 B1 | 4/2001 | Koga |
| 6,265,417 B1 | 7/2001 | Carroll |
| 6,281,211 B1 | 8/2001 | Cai et al. |
| 6,326,385 B1 | 12/2001 | Wickenden et al. |
| 6,348,486 B1 | 2/2002 | Argentieri et al. |
| 6,395,736 B1 | 5/2002 | Parks et al. |
| 6,451,857 B1 | 9/2002 | Hurtt et al. |
| 6,469,042 B1 | 10/2002 | Hewawasam et al. |
| 6,472,165 B1 | 10/2002 | Rundfeldt et al. |
| 6,495,550 B2 | 12/2002 | McNaughton-Smith et al. |
| 6,500,455 B1 | 12/2002 | Frantsits |
| 6,537,991 B1 | 3/2003 | Shaw et al. |

(Continued)

FOREIGN PATENT DOCUMENTS

CA         2542434         5/2005

(Continued)

OTHER PUBLICATIONS

Armand et al., "Effects of retigabine (D-23129) on different patterns of epileptiform activity induced by 4-aminopyridine in rat entorhinal cortex hippocampal slices," *Naunyn-Schmiedeberg's Arch Pharmacol* 359:33-39 (1999).

Armijo et al., "Ion channels and epilepsy," *Curr Pharm Des.* 11:1975-2003 (2005).

Barhanin, M., et al., "$K_V$LQT1 and ISK (minK) proteins associate to form the $I_{Ks}$ cardiac potassium current," *Nature* 384(6604):78-80 (1996).

Beeby et al. "The synthesis and properties of 2:7-Disubstituted 1:2:3:4-tetrahydroisoquinolines," *J. Chem. Soc.* ¶ 385, 1799-1803 (1949).

Bialer et al., "Progress report on new antiepileptic drugs: a summary of the fourth Eilat conference (EILAT IV)," *Epilepsy Res.* 34:1-41 (1999).

(Continued)

*Primary Examiner* — Timothy Thomas
(74) *Attorney, Agent, or Firm* — Jones Day

(57) ABSTRACT

This invention provides a compound of formula IA

IA

[chemical structure: substituted anilide with azacycloalkyl fused ring system, showing substituents $R_1$, $R_2$, $R_3$, $R_4$, $R'$, and $-N(H)-C(=X)-(Y)_q-R_5$]

where X=O or S; Y is O or S; q=1 or 0; and other substituents are defined herein. Such compounds can affect the opening of, or otherwise modulate, voltage-gated potassium channels. They are potentially useful for the treatment and prevention of diseases and disorders which are affected by activation or modulation of potassium ion channels. One such condition is seizure disorders.

13 Claims, No Drawings

U.S. PATENT DOCUMENTS

| | | | |
|---|---|---|---|
| 6,538,004 | B2 | 3/2003 | Drizin |
| 6,538,151 | B1 | 3/2003 | Meisel et al. |
| RE38,115 | E | 5/2003 | Smith et al. |
| 6,589,986 | B2 | 7/2003 | Bowlby et al. |
| 6,593,335 | B1 | 7/2003 | Carroll |
| 6,642,209 | B1 | 11/2003 | Fukunaga |
| 6,645,521 | B2 | 11/2003 | Cassel |
| 6,737,422 | B2 | 5/2004 | McNaughton-Smith et al. |
| 7,045,551 | B2 | 5/2006 | Wu et al. |
| 7,160,684 | B2 | 1/2007 | Argentieri et al. |
| 7,250,511 | B2 | 7/2007 | Bavetsias |
| 7,309,713 | B2 | 12/2007 | Rundfeldt et al. |
| 7,419,981 | B2 | 9/2008 | Field et al. |
| 2002/0013349 | A1 | 1/2002 | Wickenden |
| 2002/0015730 | A1 | 2/2002 | Hoffmann et al. |
| 2002/0183395 | A1 | 12/2002 | Argentieri |
| 2004/0198724 | A1 | 10/2004 | McNaughton-Smith |
| 2005/0070570 | A1 | 3/2005 | Garcia et al. |
| 2005/0089473 | A1 | 4/2005 | Black et al. |
| 2005/0089559 | A1 | 4/2005 | Szelenyi |
| 2005/0090547 | A1 | 4/2005 | Szelenyi |
| 2005/0202394 | A1 | 9/2005 | Dobson |
| 2005/0277579 | A1 | 12/2005 | Krishnan et al. |
| 2007/0066612 | A1 | 3/2007 | Khanzhin et al. |

FOREIGN PATENT DOCUMENTS

| | | |
|---|---|---|
| DE | 3337593 | 10/1983 |
| DE | 3604575 A1 | 8/1986 |
| DE | 103 49 729.3 | 10/2003 |
| DE | 103 59 335 | 5/2005 |
| EP | 189788 A1 | 8/1986 |
| EP | 0 343 429 | 5/1989 |
| EP | 1 334 972 | 8/2003 |
| EP | 1 407 768 | 4/2004 |
| EP | 1 813 285 A1 | 8/2007 |
| JP | 2000 14350 | 5/2000 |
| JP | 2000 143510 A | 5/2000 |
| RU | 2006117525 | 12/2005 |
| WO | WO/00/55137 | 9/2000 |
| WO | WO 00/59487 A2 | 10/2000 |
| WO | WO 00/59508 A1 | 10/2000 |
| WO | WO 01/01970 | 1/2001 |
| WO | WO 01/01972 A2 | 1/2001 |
| WO | WO 01/09612 | 2/2001 |
| WO | WO 01/22953 A2 | 4/2001 |
| WO | WO 02/80898 | 10/2002 |
| WO | WO 03/020706 | 3/2003 |
| WO | WO 03/097586 | 11/2003 |
| WO | WO 03106454 A1 * | 12/2003 |
| WO | WO 2004/082677 | 3/2004 |
| WO | WO 2004/058739 | 7/2004 |
| WO | WO 2004/080950 | 9/2004 |
| WO | WO 2004/096767 | 11/2004 |
| WO | WO 2004/096767 A1 | 11/2004 |
| WO | WO 2004/105795 | 12/2004 |
| WO | WO 2005/087754 | 3/2005 |
| WO | WO 2005/039576 A1 | 5/2005 |
| WO | WO 2005/048975 | 6/2005 |
| WO | WO 2005/100349 A2 | 10/2005 |
| WO | WO 2006/029623 | 3/2006 |
| WO | WO 2006/092143 | 9/2006 |
| WO | WO 2008/024398 A2 | 2/2008 |
| WO | WO 2008/066900 A1 | 6/2008 |

OTHER PUBLICATIONS

Bialer, "Progress report on new antiepileptic drugs: a summary of the Sixth Eilat Conference (EILAT VI)," *Epilepsy Res.* 51:31-71 (2002).

Bialer, "Progress report on new antiepileptic drugs: a summary of the Seventh Eilat Conference (EILAT VII)," *Epilepsy Res.* 61:1-48 (2004).

Biervert et al., "A potassium channel mutation in neonatal human epilepsy," *Science* 279:403-406 (1998).

Blackburn-Munro and Jensen, "The anticonvulsant retigabine attenuates nociceptive behaviours in rat models of persistent and neuropathic pain," *Eur J Pharmacol.* 460: 109-116 (2003).

Brown and Adams, "Muscarinic suppression of a novel voltage-sensitive $K^+$ current in a vertebrate neurone," *Nature* 283:673-676 (1980).

Brown, D.A., *Ion Channels*, T. Narahashi, Ed. (Plenum Press, New York) pp. 55-94 (1988).

Charlier et al., "A pore mutation in a novel KQT-like potassium channel gene in an idiopathic epilepsy family," *Nat Genet.* 18:53-55 1998.

Cooper et al., "Colocalization and coassembly of two human brain M-type potassium channel subunits that are mutated in epilepsy." *Proc Natl Acad Sci USA* 97:4914-4919 (2000).

Delmas and Brown, "Pathways modulating neural KCNQ/M (Kv7) potassium channels," *Nat Rev Neurosci.* 6:850-862 (2005).

Dickenson al., "Neurobiology of neuropathic pain: mode of action of anticonvulsants," *Eur. J. Pain* 6:51-60 (2002).

Dost et al., "The anticonvulsant retigabine potently suppresses epileptiform discharges in the low Ca ++ and low Mg++ model in the hippocampal slice preparation," *Epilepsy Res.* 38:53-56 (2000).

Friedel and Fitton, "Flupirtine: a review of its analgesic properties, and therapeutic efficacy in pain states," *Drugs* 45:548-569 (1993).

Hiller et al., "Retigabine N-glucuronidation and its potential role in enterohepatic circulation," *Drug Metab Dispos.* 27(5):605-612 (1999).

Hunt and Mantyh, "The molecular dynamics of pain control," *Nat Rev Neurosci.* 2:83-91 (2001).

Jentsch, "Neuronal KCNQ potassium channels; physiology and role in disease," *Nat. Rev Neurosci.*, 1:21-30 (2000).

Jiang et al., "X-ray structure of a voltage-dependent K+ channel," *Nature* 423:33-41 (2003).

Kharkovets et al., "Mice with altered KCNQ4 $K^+$ channels implicate sensory outer hair cells in human progressive deafness," *EMBO J* 25:642-652 (2006).

Kibbe *Handbook of Pharmaceutical Excipients* (Pharmaceutical Press, London) (2000).

Kubisch et al., "KCNQ4, a novel potassium channel expressed in sensory outer hair cells, is mutated in dominant deafness," *Cell* 96:437-446 (1999).

Lamas et al., "Effects of a cognition-enhancer, linopirdine (DuP 996), on M-type potassium currents ($I_{K(M)}$) and some other voltage- and ligand-gated membrane currents in rat sympathetic neurons," *Eur. J Neurosci.*, 9:605-616 (1997).

Lee et al., "Structure of the KvAP voltage-dependent $K^+$ channel and its dependence on the lipid membrane," *Proc Natl Acad Sci USA* 102:15441-15446 (2005).

Long et al., "Crystal Structure of a mammalian voltage-dependent Shaker family $K^{+channel}$," *Science* 309:897-903 (2005).

Main et al., "Modulation of KCNQ2/3 potassium channels by the novel anticonvulsant retigabine," *Mol. Pharmacol.* 58:253-262 (2000).

Marrion, "Control of M-currents," *Annu Rev Physiol.* 59:483-504 (1997).

Parcej and Eckhardt-Strelau, Structural characterization of neuronal voltage-sensitive $K^+$ channels heterologously expressed in *Pichia pastoris, J Mol Biol* 333:103-116 (2003).

Passmore et al., "KCNQ/M currents in sensory neurons: significance for pain therapy," *J. Neurosci.* 23:7227-7236 (2003).

Porter et al., "Retigabine," *Neurotherapeutics* 4:149-154 (2007).

Reich et al., "Design and synthesis of novel 6,7-imidazotetrahydroquinoline inhibitors of thymidylate synthase using iterative protein crystal structure analysis," *J. Med. Chem.* 35:847-858 (1992).

Rogawski, Ma, "KCNQ2/KCNQ3 K+ channels and the molecular pathogenesis of epilepsy: implications for therapy," *Trends Neurosci.* 23:393-398 (2000).

Rostock et al., "A new anticonvulsant with broad spectrum activity in animal models of epileptic seizures," *Epilepsy Res.* 23:211-223 (1996).

Rundfeldt et al., "Multiple actions of the new anticonvulsant D-23129 on voltage-gated inward currents and GABA-induced currents in cultured neuronal cells (abstract)," *Naunyn-Schmiedeberg's Arch Pharmacol* 351 (Suppl):R160 (1995).

Rundfeldt, "Characterization of the $K^+$ channel opening effect of the anti-convulsant retigabine in PC12 cells," *Epilepsy Res.* 35:99-107 (1999).

Rundfeldt, "The new anticonvulsant retigabine (D23129) acts as an opener of K+ channels in neuronal cells," *Eur J Pharmacol.* 336:243-249 (1997).

Schroeder et al., "KCNQ5, a novel potassium channel broadly expressed in brain, mediates M-type currents," *J. Biol. Chem.* 275:24089-24095 (2000).

Schroeder, "Moderate loss of function of cyclic-AMP-modulated KNCQ2/KCNQ3 K+ channels causes epilepsy," *Nature* 396:687-690 (1998).

Singh et al., "A novel potassium channel gene, KCNQ2, is mutated in an inherited epilepsy of newborns," *Nat Genet.* 18:25-29 (1998).

Suzuki and Dickenson, "Neuropathic pain: nerves bursting with excitement," *NeuroReport* 11:R17-R21 (2000).

Tatulian and Brown, "Effect of the KCNQ potassium channel opener retigabine on single KCNQ2/3 channels express in CHO cells," *J Physiol.* 549:57-63 (2003).

Tatulian et al., "Activation of expressed KCNQ potassium currents and native neuronal M-type potassium currents by the anti-convulsant drug retigabine," *J. Neurosci.* 21:5535-5545 (2001).

Tober et al., "A potent anticonvulsant in the amygdala kindling model of complex partial seizures," *Eur J Pharmacol*, 303:163-169 (1996).

Von Bebenburg et al., "Substituierte Polyaminopyridine" *Chemiker-Zeitung* 103:387-399 (1979). (German language article attached).

Wang et al., KCNQ2 and KCNQ3 potassium channel subunits: molecular correlates of the M-channel, *Science* 282:1890-1893 (1998).

Wang et al., "Positional cloning of a novel potassium channel gene: KVLQT1 mutations cause cardiac arrhythmias," *Nat Genet* 12:17-23 (1996).

Watanbe et al., "Disruption of the epilepsy KCNQ2 gene results in neural hyperexcitability," *J. Neurochem* 75:28-33 (2000).

Wickenden et al., "KCNQ potassium channels: drug targets for the treatment of epilepsy and pain," *Exp. Opin Thera Patents* 14(4): 457-469 (2004).

Wickenden et al., "Retigabine, a novel anti-convulsant, enhances activation of KCNQ2/Q3 potassium channels," *Mol. Pharmacol.* 58:591-600 (2000).

Wuttke, "The new anticonvulsant retigabine favors voltage-dependent opening of the Kv7.2 (KCNQ2) channel by binding to its activation gate," *Mol. Pharmacol.* 67:1009-1017 (2005).

Fodor et al., "Attempts to find new spasmolytics. VIII. The synthesis of 6,7-diethoxy-3-alkyl- and 6,7-diethyl-3-phenyl-isoquinolines," *J. Chem. Soc.* 1681-1682 (1949).

Kuo et al., "Inhibition of Na+ current by diphenhydramine and other diphenyl compounds: molecular determinants of selective binding to the inactivated channels," *Mol. Pharmacol.* 57(1):135-143 (2000).

Patani, "Bioisosterism: A Rational Approach in Drug Design," *Chem. Rev.* 96:3147-3176 (1996).

Touboul et al., "A Comparative evaluation of the effects of Propafenone and lidocaine on early ventricular arrhythmias after acute myocardial infarction," *Eur. Heart J.* 9:1188-1193 (1988). Abstract.

Vippagunta et al., "Crystalline solids," *Adv. Drug Deliv. Rev.* 48:3-26 (2001).

West, Solid State Chemistry and Its Applications (John Wiley & Sons, New York) pp. 358 and 365 (1988).

Wu et al., "Regulatory perspectives of Type II prodrug development and time-dependent toxicity management: nonclinical Pharm/Tox analysis and the role of comparative toxicology," *Toxicology* 236:1-6 (2007).

Zani et al., "Sodium channels are required during in vivo sodium chloride hyperosmolarity to stimulate increase in intestinal endothelial nitric oxide production," *Am. J. Physiol. Heart Circ. Physiol.* 288:H89-H95 (2005).

* cited by examiner

DERIVATIVES OF 4-(N-AZACYCLOALKYL) ANILIDES AS POTASSIUM CHANNEL MODULATORS

CROSS REFERENCE TO RELATED APPLICATIONS

This application claims the benefit of U.S. Provisional Application Ser. No. 60/839,941, filed Aug. 23, 2006.

FIELD OF THE INVENTION

This invention concerns novel compounds that activate or otherwise modulate voltage-gated potassium channels. The compounds are useful for the treatment and prevention of diseases and disorders which are affected by modulation of potassium ion channels. One such condition is seizure disorders.

BACKGROUND OF THE INVENTION

Epilepsy is a well-known neurological disease, found in about 3% of the population. Approximately 30% of patients with epilepsy do not respond to currently available therapies. Such unfortunate patients—who number hundreds of thousands of people world-wide—must contend with both uncontrolled seizures and the resulting narrowing of their options in such crucial areas of life as health insurance, employment, and driving.

Retigabine (N-[2-amino-4-(4-fluorobenzylamino)phenyl] carbamic acid, ethyl ester) (U.S. Pat. No. 5,384,330) has been found to be an effective treatment of seizure disorders and has also been found useful in treating pain. Retigabine has been found to be particularly potent in models for the drug-refractory types of epilepsy. Bialer, M. et al., *Epilepsy Research* 1999, 34, 1-41; Blackburn-Munro and Jensen, *Eur. J. Pharmacol.* 2003, 460, 109-116; Wickenden, A. D. et al., *Expert Opin. Ther. Patents*, 2004, 14(4).

"Benign familial neonatal convulsions," an inherited form of epilepsy, has been associated with mutations in the KCNQ2/3 channels. Biervert, C. et al., *Science* 1998, 27, 403-06; Singh, N. A., et al., *Nat. Genet.* 1998, 18, 25-29; Charlier, C. et al., *Nat. Genet.* 1998, 18, 53-55; Rogawski, *Trends in Neurosciences* 2000, 23, 393-398. Subsequent investigations have established that one important site of action of retigabine is the KCNQ2/3 channel. Wickenden, A. D. et al., *Mol. Pharmacol.* 2000, 58, 591-600; Main, M. J. et al., *Mol. Pharmcol.* 2000, 58, 253-62. Retigabine has been shown to increase the conductance of the channels at the resting membrane potential, with a possible mechanism involving binding of the activation gate of the KCNQ 2/3 channel. Wuttke, T. V., et al., *Mol. Pharmacol.* 2005. Additionally, retigabine has been shown to increase neuronal M currents and to increase the channel open probability of KCNQ 2/3 channels. Delmas, P. and Brown, D. A. *Nat. Revs Neurosci.*, vol. 6, 2005, 850-62; Tatulian, L. and Brown, D. A., *J. Physiol.*, (2003) 549, 57-63.

The seizure type that has been most resistant to therapy is the so-called "complex partial seizure." Retigabine is active in several seizure models, including, as indicated above, models for drug-refractory epilepsy. Because of retigabine's broad spectrum of activity and its unusual molecular mechanism, there is hope that retigabine will be effective in management of several seizure types, including the complex partial seizure, which have been resistant to treatment. Porter, R. J., Nohria, V., and Rundfeldt, C., *Neurotherapeutics,* 2007, vol. 4, 149-154.

The recognition of retigabine as a potassium channel opener has inspired a search among compounds with structural features in common with retigabine for other compounds which can affect the opening of, or otherwise modulate, potassium ion channels.

BRIEF DESCRIPTION OF THE INVENTION

In their efforts to design a potassium channel modulating compound that is superior to retigabine, shown below, which is a benzyl amine derivative,

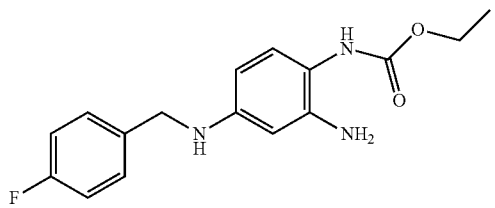

the present inventors have discovered surprising and exceptionally promising properties in a series of tetrahydroisoquinoline derivatives, specifically, para-N-(1,2,3,4-tetrahydro) isoquinolyl anilides and carbamates, and their several sulfur analogues, of the structure of formula IA below These tetrahydroisoquinoline derivatives are, of course, benzyl amines which are restricted to particular conformations because the benzylic nitrogen is a member of a second ring fused to the phenyl ring. Moreover, the present inventors have further discovered that replacement of the primary amino group of retigabine with substituents like halogen, $C_1$-$C_3$ alkyl, $OC_1$-$C_3$ alkyl, and trifluoromethyl also confers surprising and desirable properties.

Thus, in one embodiment, this invention provides or contemplates a compound of formula IA

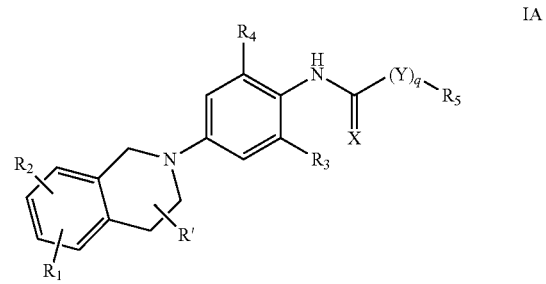

where $R_1$ and $R_2$, are, independently, H, CN, halogen, $CH_2CN$, OH, $NO_2$, $CH_2F$, $CHF_2$, $CF_3$, $CF_2CF_3$, $C_1$-$C_6$ alkyl, $C(=O)C_1$-$C_6$ alkyl; $NH_2$, NH—$C_1$-$C_6$ alkyl; N($C_1$-$C_6$ alkyl)-$C_1$-$C_6$ alkyl, NHC(=O)$C_1$-$C_6$ alkyl, C(=O)N(CH$_3$)$_2$, C(=O)N(Et)$_2$, C(=O)NH$_2$, C(=O)NH—$C_1$-$C_6$ alkyl, SO$_2$NH$_2$, NHSO$_2$—$C_1$-$C_6$ alkyl; C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_6$ cycloalkyl, $(CH_2)_m C_3$-$C_6$ cycloalkyl, $C_3$-$C_6$ cycloalkenyl, $(CH_2)_m C_3$-$C_6$ cycloalkenyl, $C_2$-$C_6$ alkenyl, $C_2$-$C_6$ alkynyl, Ar, $(CH_2)_m$thienyl, $(CH_2)_m$furyl, $(CH_2)_m$imidazolyl, $(CH_2)_m$pyrazyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl, which cycloalkyl and said cycloalkenyl groups optionally contain one or two heteroatoms selected independently from O, N, and S, and which are optionally substituted as described below; where m is zero, 1, or 2, Ar is a 5- to 10-member mono- or bicyclic aromatic group, optionally containing 1-4 ring heteroatoms selected independently from N, O, and S; or $R_1$ and $R_2$, together with the ring carbon atoms to which they are attached, form a 5- or 6-member fused ring, which ring may be saturated, unsaturated, or aromatic, which optionally contains one or two heteroatoms selected independently from O, N, and S, and which is optionally substituted as described below; R' is H, halogen, phenyl, 2-(N,N-dimethylamino) ethyl, $CF_3$, $OC_1$-$C_3$ alkyl or $C_1$-$C_3$ alkyl; $R_3$ and $R_4$ are, independently, H, CN, halogen, $CF_3$, $OCF_3$, $OC_1$-$C_3$ alkyl, or $C_1$-$C_6$ alkyl; X=O or S; Y is O or S; q=1 or zero; $R_5$ is $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, Ar, $(CHR_6)_w$Ar, $CH_2(CHR_6)_w$Ar, or $(CHR_6)_w CH_2$Ar, where w=zero, 1, 2, or 3, Ar is a 5- to 10-member mono- or bicyclic aromatic group, optionally containing 1-4 ring heteroatoms selected independently from N, O, and S; $R_6$ is H or $C_1$-$C_3$ alkyl; where all cycloalkyl and cycloalkenyl groups optionally contain one or two ring heteroatoms selected independently from N, O, and S; where all alkyl, cycloalkyl, alkenyl, cycloalkenyl, heterocycloalkyl, heterocycloalkenyl, alkynyl, aryl, and heteroaryl groups in $R_1$, $R_2$, R', $R_3$, $R_4$, $R_5$, $R_6$, and Ar are optionally substituted with one or two substituents selected independently from $C_1$-$C_3$ alkyl, halogen, CN, OH, OMe, OEt, CN, $CH_2F$, and trifluoromethyl; and where, additionally, all cycloalkyl and heterocycloalkyl groups are optionally substituted with a carbonyl group. Such compounds are potassium channel activators or modulators.

Essentially all combinations of the several variables in formula IA are contemplated by this invention.

In another embodiment, this invention provides or contemplates a composition comprising a pharmaceutically acceptable carrier or diluent and at least one of the following: a pharmaceutically effective amount of a compound of formula IA, a pharmaceutically acceptable salt of a compound of formula IA, a pharmaceutically acceptable solvate of a compound of formula IA, and a pharmaceutically acceptable ester of a compound of formula IA.

In yet another embodiment, this invention provides or contemplates a pediatric pharmaceutical composition comprising a pharmaceutically acceptable carrier or diluent, a syrup for pediatric use, and at least one of the following: a pharmaceutically effective amount of a compound of formula IA, a pharmaceutically acceptable salt of a compound of formula IA, a pharmaceutically acceptable ester of a compound of formula IA, and a pharmaceutically acceptable solvate of a compound of formula IA.

In yet another embodiment, this invention provides or contemplates a chewable tablet, suitable for pediatric pharmaceutical use, comprising a pharmaceutically acceptable carrier or diluent, and at least one of the following: a pharmaceutically effective amount of a compound of formula IA, a pharmaceutically acceptable salt of a compound of formula IA, a pharmaceutically acceptable solvate of a compound of formula IA, and a pharmaceutically acceptable ester of a compound of formula IA.

In yet another embodiment, this invention provides or contemplates a method of preventing or treating a disease or disorder which is affected by activation voltage-gated potassium channels, comprising administering to a patient in need thereof a therapeutically effective amount of a compound of formula IA or a salt or ester or solvate thereof.

This invention includes all tautomers and salts of compounds of this invention. This invention also includes all compounds of this invention where one or more atoms are replaced by a radioactive isotope thereof.

This invention provides or contemplates compounds of formula IA above where the group NH—C(=X)—$(Y)_q$—$R_5$ is each of the following: NHC(=O)$R_5$, NHC(=O)O$R_5$, NHC(=S)$R_5$, NHC(=S)S$R_5$, NHC(=S)O$R_5$, and NHC(=O)S$R_5$.

Thus, in one embodiment, this invention provides or contemplates a compound of formula IA, where NH—C(=X)—$(Y)_q$—$R_5$ is NHC(=O)$R_5$.

In another embodiment, this invention provides or contemplates a compound of formula IA, where NH—C(=X)—$(Y)_q$—$R_5$ is NHC(=S)$R_5$.

In another embodiment, this invention provides or contemplates a compound of formula IA, where NH—C(=X)—$(Y)_q$—$R_5$ is NHC(=S)S$R_5$.

In another embodiment, this invention provides or contemplates a compound of formula IA, where NH—C(=X)—$(Y)_q$—$R_5$ is each NHC(=O)O$R_5$.

In another embodiment, this invention provides or contemplates a compound of formula IA, where NH—C(=X)—$(Y)_q$—$R_5$ is NHC(=S)O$R_5$.

In another embodiment, this invention provides or contemplates a compound of formula IA, where NH—C(=X)—$(Y)_q$—$R_5$ is NHC(=O)S$R_5$.

In another generic embodiment, this invention provides or contemplates a compound of formula IA, where q is zero and $R_5$ is $C_1$-$C_6$ alkyl, or $(CHR_6)_w C_3$-$C_6$ cycloalkyl.

In another subgeneric embodiment, this invention provides or contemplates a compound of formula IA, where R' is H, methyl, ethyl, or halogen.

In another subgeneric embodiment, this invention provides or contemplates a compound of formula IA, where R' is phenyl.

In another subgeneric embodiment, this invention provides or contemplates a compound of formula IA, where R' is $OC_1$-$C_3$ alkyl.

In another subgeneric embodiment, this invention provides or contemplates a compound of formula IA, where R' is 2-dimethylaminoethyl.

In another subgeneric embodiment, this invention provides or contemplates a compound of formula IA, where R' is H.

In another subgeneric embodiment, this invention provides or contemplates a compound of formula IA, where R' halogen.

In another subgeneric embodiment, this invention provides or contemplates a compound of formula IA, where R' is methyl or ethyl.

In another subgeneric embodiment, $R_1$ is located as shown below

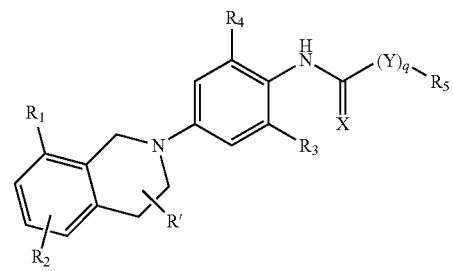

In another subgeneric embodiment, $R_1$ is located as shown below

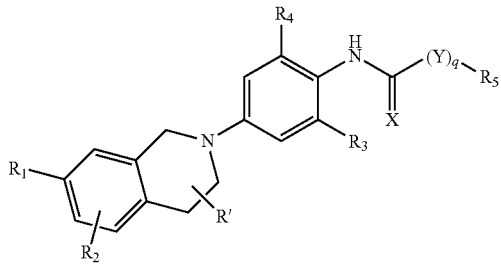

In another subgeneric embodiment, $R_1$ is located as shown below

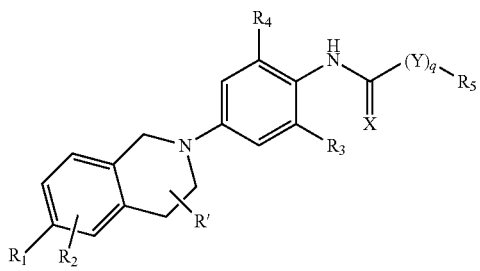

In another subgeneric embodiment, $R_1$ is located as shown below

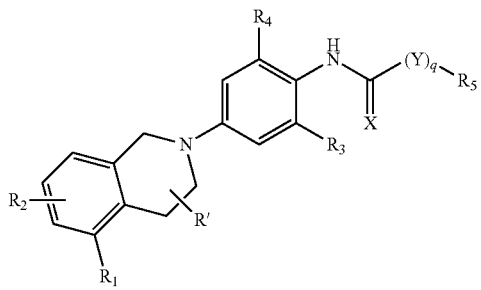

In another subgeneric embodiment, this invention provides or contemplates a compound of the structure shown below.

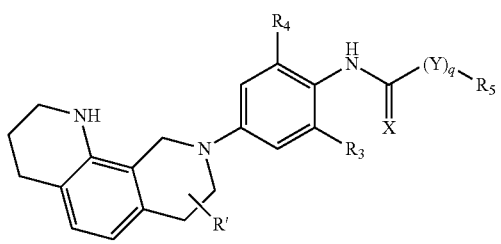

In another subgeneric embodiment, this invention provides or contemplates a compound of the structure shown below.

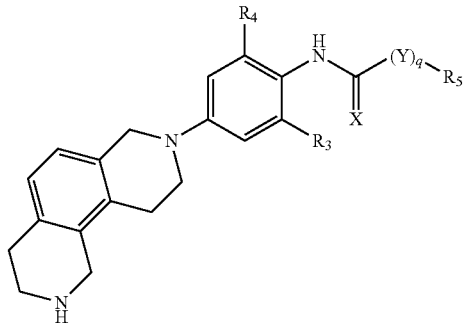

In a more specific subgeneric embodiment, this invention provides or contemplates a compound of the structure shown below, where $R_5$ is $C_5$-$C_6$ alkyl or $(CH_2)_w C_5$-$C_6$ cycloalkyl.

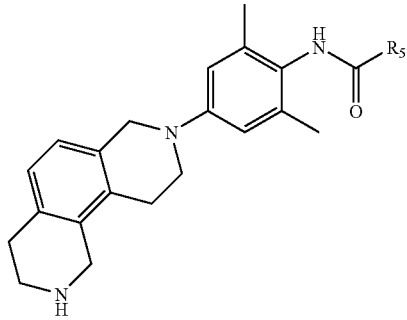

In another more specific subgeneric embodiment, this invention provides or contemplates a compound of the structure shown below, where $R_5$ is $C_5$-$C_6$ alkyl or $(CH_2)_w C_5$-$C_6$ cycloalkyl.

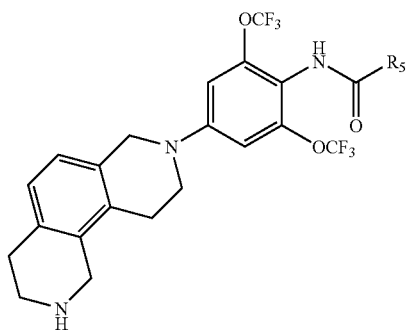

In another specific subgeneric embodiment, this invention provides or contemplates a compound of the structure shown below, where $R_3$ and $R_4$ are, independently, H, methyl, or methoxy.

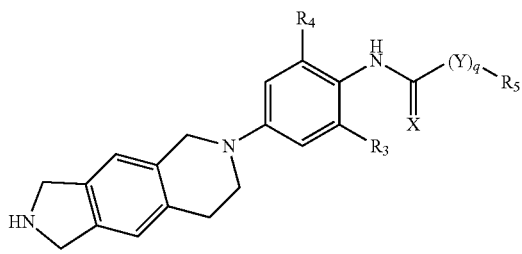

In a more specific subgeneric embodiment, this invention provides or contemplates a compound of the structure shown below, where $R_3$ and $R_4$ are, independently, H, methyl, or methoxy, and $R_5$ is $C_5$-$C_6$ alkyl or $(CH_2)_w C_5$-$C_6$ cycloalkyl.

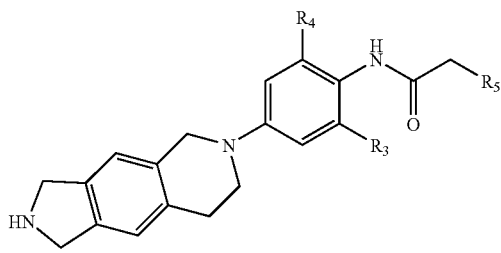

In a still more specific subgeneric embodiment, this invention provides or contemplates a compound of the structure shown below, where $R_5$ is $C_5$-$C_6$ alkyl or $(CH_2)_w C_5$-$C_6$ cycloalkyl.

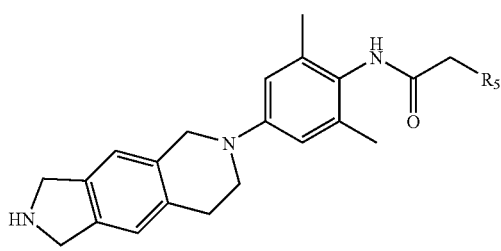

In another specific subgeneric embodiment, this invention provides or contemplates a compound of the structure shown below, where $R_3$ and $R_4$ are, independently, H, methyl, or methoxy.

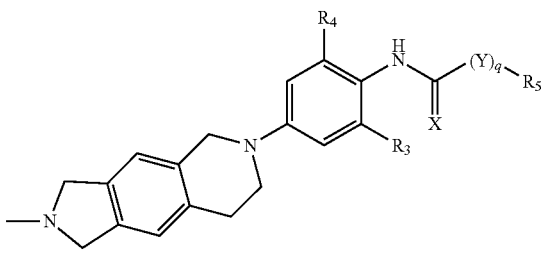

In another specific subgeneric embodiment, this invention provides or contemplates a compound of the structure shown below, where $R_3$ and $R_4$ are, independently, H, methyl, or methoxy.

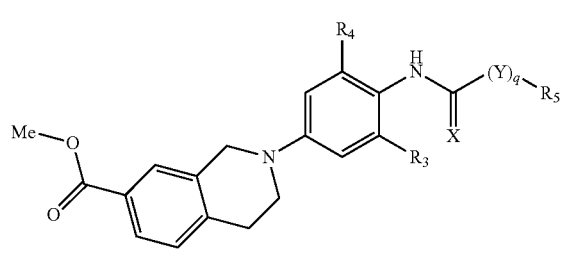

In a still more specific subgeneric embodiment, this invention provides or contemplates a compound of the structure shown below, where $R_5$ is $C_5$-$C_6$ alkyl or $(CH_2)_w C_5$-$C_6$ cycloalkyl.

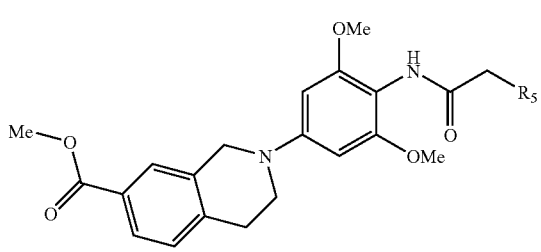

In another specific subgeneric embodiment, this invention provides or contemplates a compound of the structure shown below, where $R_3$ and $R_4$ are, independently, H, methyl, Cl, $CF_3$, $OCF_3$, or methoxy.

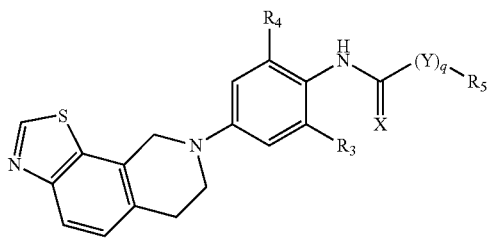

In a still more specific subgeneric embodiment, this invention provides or contemplates a compound of the structure shown below, where $R_5$ is $C_5$-$C_6$ alkyl or $(CH_2)_w C_5$-$C_6$ cycloalkyl.

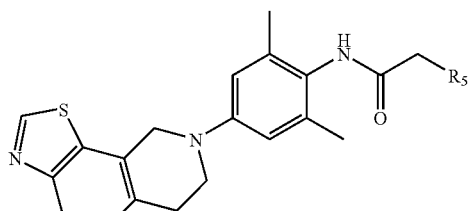

In another specific subgeneric embodiment, this invention provides or contemplates a compound of the structure shown below, where $R_3$ and $R_4$ are, independently, H, methyl, Cl, $CF_3$, $OCF_3$, or methoxy.

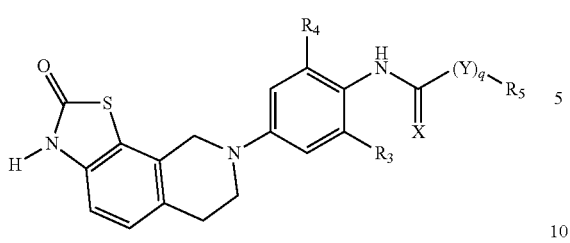

In a more specific subgeneric embodiment, this invention provides or contemplates a compound of the structure shown below, where $R_5$ is $C_5$-$C_6$ alkyl or $(CH_2)_w$ $C_5$-$C_6$ cycloalkyl.

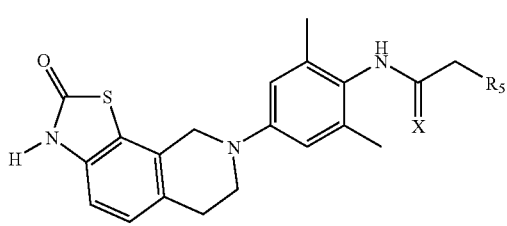

In another more specific subgeneric embodiment, this invention provides or contemplates a compound of the structure shown below, where $R_5$ is $C_5$-$C_6$ alkyl or $(CH_2)_w$ $C_5$-$C_6$ cycloalkyl.

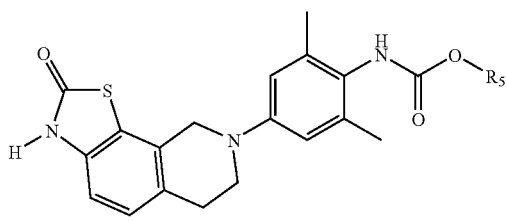

In yet another more specific subgeneric embodiment, this invention provides or contemplates a compound of the structure shown below, where $R_5$ is $(CH_2)_w$Ar or $C_3$-$C_6$ alkyl.

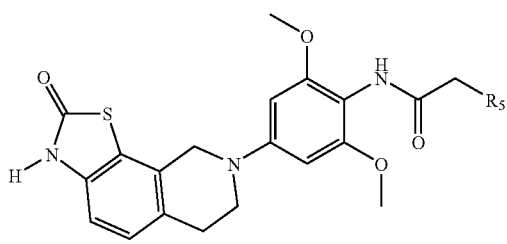

In another subgeneric embodiment, this invention provides or contemplates a compound of the structure shown below, where $R_3$ and $R_4$ are, independently, H, methyl, Cl, CF$_3$, OCF$_3$, or methoxy.

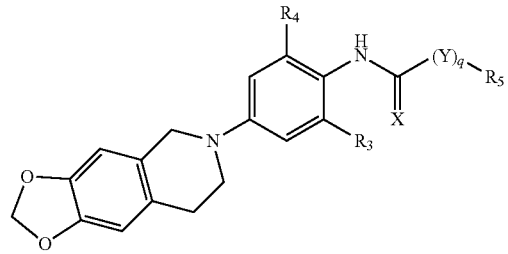

In a more specific subgeneric embodiment, this invention provides or contemplates a compound of the structure shown below, where $R_3$ and $R_4$ are, independently, H, methyl, Cl, CF$_3$, OCF$_3$, or methoxy and $R_5$ is $(CH_2)_w$Ar or $C_3$-$C_6$ alkyl

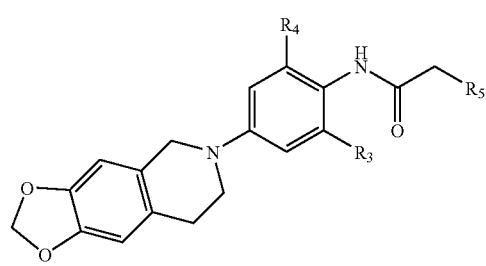

In another subgeneric embodiment, this invention provides or contemplates a compound of the structure shown below, where $R_5$ is $(CH_2)_w$Ar or $C_3$-$C_6$ alkyl.

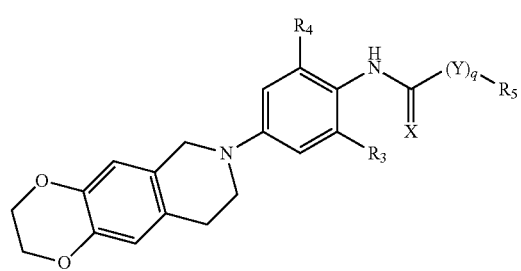

In yet another more specific subgeneric embodiment, this invention provides or contemplates a compound of the structure shown below, where $R_3$ and $R_4$ are, independently, H, methyl, Cl, CF$_3$, OCF$_3$, or methoxy and where $R_5$ is $(CH_2)_w$Ar or $C_3$-$C_6$ alkyl.

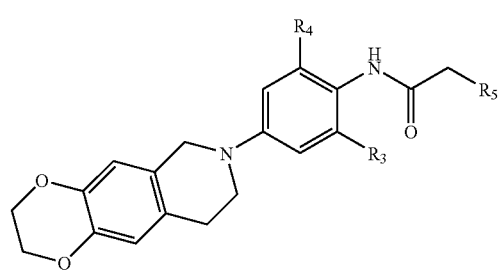

In another subgeneric embodiment, this invention provides or contemplates a compound of formula IA, where $R_2$ is H.

In another subgeneric embodiment, this invention provides or contemplates a compound of formula IA, where $R_2$ is halogen.

In another, more specific subgeneric embodiment, this invention provides or contemplates a compound of formula IA, where $R_2$ is Cl or F.

In another subgeneric embodiment, this invention provides or contemplates a compound of formula IA, where $R_2$ is trifluoromethyl.

In another subgeneric embodiment, this invention provides or contemplates a compound of formula IA, where $R_3$ and $R_4$ are, independently, H, Cl, methyl, ethyl, trifluoromethyl, or methoxy.

In another, more specific subgeneric embodiment, this invention provides or contemplates a compound of formula IA, where q is zero and $R_3$ and $R_4$ are Cl, ethyl, methoxy, or methyl.

In another, more specific subgeneric embodiment, this invention provides or contemplates a compound of formula IA, where q is zero and $R_3$ and $R_4$ are both methyl.

In another subgeneric embodiment, this invention provides or contemplates a compound of formula IA, where R' is methyl, halogen, or H; and $R_3$ and $R_4$ are, independently, H, Cl, ethyl, methoxy, or methyl.

In another subgeneric embodiment, this invention provides or contemplates a compound of formula IA, where R' is methoxy; and $R_3$ and $R_4$ are, independently, H, Cl, ethyl, methoxy, or methyl.

In another more specific subgeneric embodiment, this invention provides or contemplates a compound of formula IA, where R' is H; and $R_3$ and $R_4$ are, independently, H, Cl, ethyl, or methyl.

In another subgeneric embodiment, this invention provides or contemplates a compound of formula IA, where R' is H, q is zero, and $R_5$ is $C_1$-$C_6$ alkyl, or $(CHR_6)_w C_3$-$C_6$ cycloalkyl.

In another subgeneric embodiment, this invention provides or contemplates a compound of formula IA, where R' is H; q is 1; Y is O; and $R_5$ is $C_1$-$C_6$ alkyl, or $(CHR_6)_w C_3$-$C_6$ cycloalkyl.

In another subgeneric embodiment, this invention provides or contemplates a compound of formula IA, where R' is H; q is 1; Y is S; and $R_5$ is $C_1$-$C_6$ alkyl, or $(CHR_6)_w C_3$-$C_6$ cycloalkyl.

In a more specific subgeneric embodiment, this invention provides or contemplates a compound of formula IA, where R' and $R_2$ are H and $R_5$ is $C_1$-$C_6$ alkyl, or $(CHR_6)_w C_3$-$C_6$ cycloalkyl.

In a more specific subgeneric embodiment, this invention provides or contemplates a compound of formula IA, where R' and $R_2$ are H and $R_5$ is Ar, $(CHR_6)_w$Ar, $CH_2(CHR_6)_w$Ar, or $(CHR_6)_w CH_2$Ar.

In a more specific subgeneric embodiment, this invention provides or contemplates a compound of formula IA, where R' and $R_2$ are H and $R_5$ is $(CHR_6)_w C_5$-$C_6$ cycloalkenyl, $CH_2(CHR_6)_w C_5$-$C_6$ cycloalkenyl, $C_2$-$C_6$ alkenyl, or $C_2$-$C_6$ alkynyl.

In a more specific subgeneric embodiment, this invention provides or contemplates a compound of formula IA, where R' and $R_2$ are H and $R_5$ is $CR_6$=CH—$C_3$-$C_6$ cycloalkyl or CH=$CR_6$—$C_3$-$C_6$ cycloalkyl.

In another more specific subgeneric embodiment, this invention provides or contemplates a compound of formula IA, where R' is halogen; and $R_3$ and $R_4$ are H, Cl, ethyl, or methyl.

In another more specific subgeneric embodiment, this invention provides or contemplates a compound of formula IA, where R' is Cl or F; and $R_3$ and $R_4$ are H, Cl, ethyl, or methyl.

In another more specific subgeneric embodiment, this invention provides or contemplates a compound of formula IA, where R' is Cl or F; $R_3$ and $R_4$ are H, Cl, ethyl, or methyl; and $R_5$ is $C_1$-$C_6$ alkyl, or $(CHR_6)_w C_3$-$C_6$ cycloalkyl.

In another subgeneric embodiment, this invention provides or contemplates a compound of formula IA, where R' is phenyl, optionally substituted.

In another more specific subgeneric embodiment, this invention provides or contemplates a compound of formula IA, where R' is 1-phenyl, optionally substituted.

In another more specific subgeneric embodiment, this invention provides or contemplates a compound of formula IA, where R' is 4-phenyl, optionally substituted.

In another more specific subgeneric embodiment, this invention provides or contemplates a compound of formula IA, where R' is phenyl, optionally substituted, and $R_5$ is $C_1$-$C_6$ alkyl, or $(CHR_6)_w C_3$-$C_6$ cycloalkyl.

In another more specific subgeneric embodiment, this invention provides or contemplates a compound of formula IA, where $R_1$ is NH—$C_1$-$C_6$ alkyl, N($C_1$-$C_6$ alkyl)-$C_1$-$C_6$ alkyl, C(=O)NH—$C_1$-$C_6$ alkyl, NH—C(=O)$C_1$-$C_6$ alkyl; O—$C_1$-$C_6$ alkyl, C(=O)—$C_1$-$C_6$ alkyl, C(=O)—O$C_1$-$C_6$ alkyl, or OC(=O)$C_1$-$C_6$ alkyl; R' is phenyl, optionally substituted, and $R_5$ is $C_1$-$C_6$ alkyl, or $(CH_6)_w C_3$-$C_6$ cycloalkyl.

In another subgeneric embodiment, this invention provides or contemplates a compound of formula IA, where R' is H, methyl, or ethyl; and $R_1$ is NH—$C_1$-$C_6$ alkyl, N($C_1$-$C_6$ alkyl)-$C_1$-$C_6$ alkyl, C(=O)NH—$C_1$-$C_6$ alkyl, or NH—C(=O)$C_1$-$C_6$ alkyl.

In yet another subgeneric embodiment, this invention provides or contemplates a compound of formula IA, where R' is H, methyl, or ethyl; and $R_1$ is C(=O)O$C_1$-$C_6$ alkyl, OC(=O)$C_1$-$C_6$ alkyl, or O$C_1$-$C_6$ alkyl.

In another specific subgeneric embodiment, this invention provides or contemplates a compound of formula IA, where $R_1$ is H, methyl, methoxy, or halogen, and R' is methyl or ethyl.

In another more specific subgeneric embodiment, this invention provides or contemplates a compound of formula IA, where $R_1$ is H, methyl, methoxy, or halogen, and R' is phenyl.

In another more specific subgeneric embodiment, this invention provides or contemplates a compound of formula IA, where $R_1$ is H, methyl, methoxy, or halogen, and R' is F.

In another subgeneric embodiment, this invention provides or contemplates a compound of formula IA, where $R_1$ is methoxy, methoxymethyl, ethoxymethyl, or methoxyethyl.

In a more specific subgeneric embodiment, this invention provides or contemplates a compound of formula IA, where $R_1$ is methoxy, methoxymethyl, ethoxymethyl, or methoxyethyl; $R_2$ is H, methyl, or halogen; and $R_3$ is methyl or Cl.

In another more specific subgeneric embodiment, this invention provides or contemplates a compound of formula IA, where R' is 4-phenyl, optionally substituted, and $R_2$ is H, methyl, methoxy, or halogen.

In another more specific subgeneric embodiment, this invention provides or contemplates a compound of formula IA, where R' is $CF_3$ or $C_1$-$C_3$ alkyl, and $R_2$ is H, methyl, methoxy, or halogen.

In another more specific subgeneric embodiment, this invention provides or contemplates a compound of formula IA, where R' is methoxy, and $R_2$ is H, methyl, methoxy, or halogen.

In another more specific subgeneric embodiment, this invention provides or contemplates a compound of formula IA, where R' is 2-dimethylamino ethyl, and $R_2$ is H, methyl, methoxy, or halogen.

In another more specific subgeneric embodiment, this invention provides or contemplates a compound of formula IA, where q is zero, $R_2$ is H, methyl, methoxy, or halogen, R' is 1-phenyl, optionally substituted; and $R_3$ and $R_4$ are H, Cl, ethyl, or methyl.

In another more specific subgeneric embodiment, this invention provides or contemplates a compound of formula IA, where q is zero, $R_2$ is H, methyl, methoxy, or halogen, R' is 4-phenyl, optionally substituted; and $R_3$ and $R_4$ are H, Cl, ethyl, or methyl.

In another more specific subgeneric embodiment, this invention provides or contemplates a compound of formula IA, where q is zero, $R_2$ is H, methyl, methoxy, or halogen; R' is $CF_3$ or $C_1$-$C_3$ alkyl; and $R_3$ and $R_4$ are H, Cl, ethyl, or methyl.

In another more specific subgeneric embodiment, this invention provides or contemplates a compound of formula IA, where q is zero, $R_2$ is H, methyl, methoxy, or halogen; R' is methoxy; and $R_3$ and $R_4$ are H, Cl, ethyl, or methyl.

In another subgeneric embodiment, this invention provides or contemplates a compound of formula IA, where q is zero; R' is (2-dimethylamino)ethyl; $R_2$ is H, methyl, methoxy, or halogen; and $R_3$ and $R_4$ are H, Cl, ethyl, or methyl.

In a more specific sub-generic embodiment, the invention provides or contemplates a compound of formula IA-1 below.

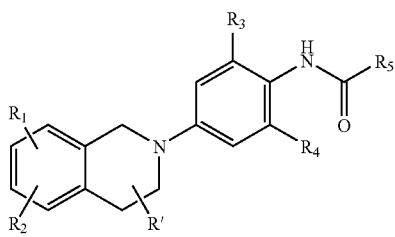

IA-1

In another more specific embodiment, this invention provides or contemplates a compound of formula IA-2 below.

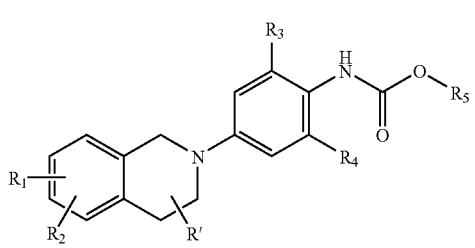

IA-2

In another more specific embodiment, this invention provides or contemplates a compound of formula IA-3 below.

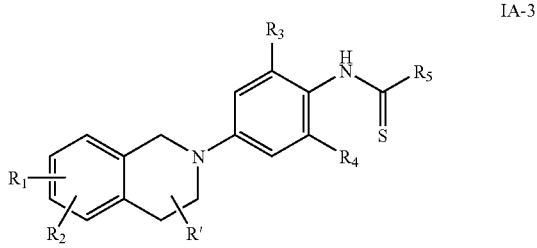

IA-3

In another more specific embodiment, this invention provides or contemplates a compound of formula IA-4 below.

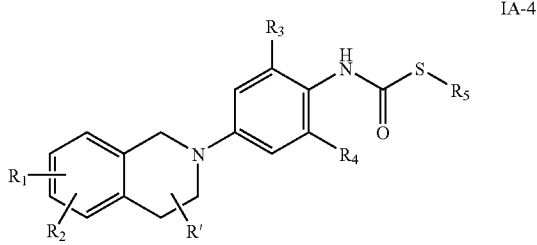

IA-4

In another more specific embodiment, this invention provides or contemplates a compound of formula IA-5 below.

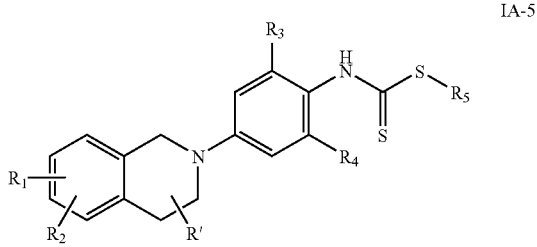

IA-5

In another subgeneric embodiment, this invention provides or contemplates a compound of formula IA-1 or formula IA-3, where $R_2$ is H, alkyl, or halogen; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA-1 or formula IA-3, where $R_1$ is $(CH_2)_m C_3$-$C_6$ cycloalkyl; $R_2$ is H, alkyl, or halogen; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In another more specific subgeneric embodiment, this invention provides or contemplates a compound of formula IA-1 or formula IA-3, where $R_1$ is methoxy, methoxymethyl, or methoxyethyl; $R_2$ is H, alkyl, or halogen; and $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In yet another more specific subgeneric embodiment, this invention provides or contemplates a compound of formula IA-2, where $R_5$ is $C_1$-$C_6$ alkyl, $(CHR_6)_w C_3$-$C_6$ cycloalkyl, $(CHR_6)_w CH_2 C_3$-$C_6$ cycloalkyl, or $CH_2(CHR_6)_w C_3$-$C_6$ cycloalkyl.

In yet another more specific subgeneric embodiment, this invention provides or contemplates a compound of formula IA-2, where $R_5$ is Ar, $(CHR_6)_w$Ar, $CH_2(CHR_6)_w$Ar, or $(CHR_6)_w CH_2$Ar.

In yet another more specific subgeneric embodiment, this invention provides or contemplates a compound of formula IA-2, where $R_5$ is $CR_6=CH-C_3-C_6$ cycloalkyl, $CH=CR_6-C_3-C_6$ cycloalkyl, $(CHR_6)_w C_5-C_6$ cycloalkenyl, $CH_2(CHR_6)_w C_5-C_6$ cycloalkenyl, $C_2-C_6$ alkenyl, or $C_2-C_6$ alkynyl.

In yet another more specific subgeneric embodiment, this invention provides or contemplates a compound of formula IA-3, where $R_2$ and R' are H; $R_3$ is methyl; and $R_5$ is $C_1-C_6$ alkyl, $(CHR_6)_w C_3-C_6$ cycloalkyl, $(CHR_6)_w CH_2 C_3-C_6$ cycloalkyl, or $CH_2(CHR_6)_w C_3-C_6$ cycloalkyl.

In a still more specific subgeneric embodiment, this invention provides or contemplates a compound of formula IA-1, where $R_1$ is H, F, Cl, Br, methoxy, methoxymethyl, ethoxymethyl, methoxyethyl, or trifluoromethyl; $R_3$ is methyl; and $R_5$ is $C_4-C_6$ alkyl, $(CHR_6)_w CH_2 C_5-C_6$ cycloalkyl, or $CH_2(CHR_6)_w C_5-C_6$ cycloalkyl.

In another still more specific subgeneric embodiment, this invention provides or contemplates a compound of formula IA-2, where $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, methoxymethyl, ethoxymethyl, methoxyethyl, or trifluoromethyl.

In another still more specific subgeneric embodiment, this invention provides or contemplates a compound of formula IA-3, where $R_1$ is H, F, Cl, Br, methoxy, methoxymethyl, ethoxymethyl, methoxyethyl, or trifluoromethyl; $R_2$ is H, methyl, or F; R' is H or methyl; $R_3$ is methyl; and $R_5$ is $C_4-C_6$ alkyl, $(CHR_6)_w C_5-C_6$ cycloalkyl, or $CH_2(CHR_6)_w C_5-C_6$ cycloalkyl.

In another more generic embodiment, this invention provides or contemplates a compound of formula IA-1, where $R_1$ is $(CH_2)_m C_3-C_6$ cycloalkyl, $C_3-C_6$ cycloalkenyl, or $(CH_2)_m C_3-C_6$ cycloalkenyl; R' is halogen; and $R_3$ is methyl or Cl.

In another more specific subgeneric embodiment, this invention provides or contemplates a compound of formula IA-1, where $R_1$ is $(CH_2)_m C_3-C_6$ cycloalkyl, $C_3-C_6$ cycloalkenyl, or $(CH_2)_m C_3-C_6$ cycloalkenyl; and R' is F or Cl.

In another more specific subgeneric embodiment, this invention provides or contemplates a compound of formula IA-1, where $R_1$ is methoxy, methoxymethyl, ethoxymethyl; or methoxyethyl; $R_2$ is H or F; $R_3$ is methyl; $R_4$ is methyl or Cl; and $R_5$ is $(CHR_6)_w C_5-C_6$ cycloalkenyl or $(CHR_6)_w$Ar.

In another more specific subgeneric embodiment, this invention provides or contemplates a compound of formula IA-1, where $R_1$ is phenyl, optionally substituted.

In another more specific subgeneric embodiment, this invention provides or contemplates a compound of formula IA-1, where $R_1$ is methyl, halomethyl, ethyl, or haloethyl.

In another subgeneric embodiment, this invention provides or contemplates a compound of formula IA-1, where R' is 2-(dimethylamino)ethyl.

In another subgeneric embodiment, this invention provides or contemplates a compound of formula IA-1, where R' is 1-methyl or 1-ethyl.

In another more specific subgeneric embodiment, this invention provides or contemplates a compound of formula IA-1, where R' is 1-fluoro, $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where R' is 4-fluoro, $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where $R_1$ is $(CH_2)_m$imidazolyl, $(CH_2)_m$pyrazoyl, $(CH_2)_m$ furyl, $(CH_2)_m$ thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl; and $R_2$ and R' are H.

In another more specific subgeneric embodiment, this invention provides or contemplates a compound of formula IA-1, where $R_1$ is $(CH_2)_m$imidazolyl, $(CH_2)_m$pyrazoyl, $(CH_2)_m$ furyl, $(CH_2)_m$ thienyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, or $(CH_2)_m$pyrimidyl; and R' is 4-phenyl, optionally substituted.

In another more specific subgeneric embodiment, this invention provides or contemplates a compound of formula IA-1, where R' is $CF_3$ or $C_1-C_3$ alkyl; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where R' is 4-methyl or 4-ethyl; and $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where R' is methoxy or ethoxy; and $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where R' is 1-phenyl, optionally substituted; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where R' is 4-phenyl, optionally substituted; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where R' is $CF_3$ or $C_1-C_3$ alkyl; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where R' is 4-methyl or 4-ethyl; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-1, where R' is methoxy or ethoxy, $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-4, where $R_1$ is H, F, Cl, Br, methoxy, or trifluoromethyl; $R_5$ is $C_4-C_6$ alkyl, $(CHR_6)_w C_5-C_6$ cycloalkyl, or $CH_2(CHR_6)_w C_5-C_6$ cycloalkyl; and $R_1$ is H, F, Cl, Br, methoxy, or trifluoromethyl.

In another more specific subgeneric embodiment, this invention provides or contemplates a compound of formula IA-4, where $R_2$ is H, F, or methyl; $R_5$ is $C_4$-$C_6$ alkyl, $(CHR_6)_wC_5$-$C_6$ cycloalkyl, or $CH_2(CHR_6)_wC_5$-$C_6$ cycloalkyl; and $R_1$ is H, F, Cl, Br, methoxy, or trifluoromethyl.

In another subgeneric embodiment, this invention provides or contemplates a compound of formula IA-2, where R' is H.

In another subgeneric embodiment, this invention provides or contemplates a compound of formula IA-2, where R' is halogen.

In another more specific subgeneric embodiment, this invention provides or contemplates a compound of formula IA-2, where R' is F.

In another more specific subgeneric embodiment, this invention provides or contemplates a compound of formula IA-2, where R' is methyl or ethyl.

In another more specific subgeneric embodiment, this invention provides or contemplates a compound of formula IA-2, where R' is methyl or ethyl; $R_5$ is $C_4$-$C_6$ alkyl, $(CHR_6)_wC_5$-$C_6$ cycloalkyl, or $CH_2(CHR_6)_wC_5$-$C_6$ cycloalkyl; and $R_1$ is H, F, Cl, Br, methoxy, or trifluoromethyl.

In another more specific subgeneric embodiment, this invention provides or contemplates a compound of formula IA-2, where R' is halogen; $R_5$ is $C_4$-$C_6$ alkyl, $(CHR_6)_wC_5$-$C_6$ cycloalkyl, or $CH_2(CHR_6)_wC_5$-$C_6$ cycloalkyl; and $R_1$ is H, F, Cl, Br, methoxy, or trifluoromethyl.

In another more specific subgeneric embodiment, this invention provides or contemplates a compound of formula IA-2, where R' is H; $R_5$ is $C_4$-$C_6$ alkyl, $(CHR_6)C_5$-$C_6$ cycloalkyl, or $CH_2(CHR_6)_wC_5$-$C_6$ cycloalkyl; and $R_1$ is H, F, Cl, Br, methoxy, or trifluoromethyl.

In another more specific subgeneric embodiment, this invention provides or contemplates a compound of formula IA-2, where R' is 1-phenyl, optionally substituted.

In another more specific subgeneric embodiment, this invention provides or contemplates a compound of formula IA-2, where R' is 4-phenyl, optionally substituted.

In another more specific subgeneric embodiment, this invention provides or contemplates a compound of formula IA-2, where R' is $CF_3$ or $C_1$-$C_3$ alkyl.

In another more specific subgeneric embodiment, this invention provides or contemplates a compound of formula IA-3, where R' is H; $R_5$ is $C_4$-$C_6$ alkyl, $(CHR_6)_wC_5$-$C_6$ cycloalkyl, or $CH_2(CHR_6)_wC_5$-$C_6$ cycloalkyl; and $R_1$ is H, F, Cl, Br, methoxy, or trifluoromethyl.

In another more specific subgeneric embodiment, this invention provides or contemplates a compound of formula IA-3, where R' is F; $R_5$ is $C_4$-$C_6$ alkyl, $(CHR_6)_wC_5$-$C_6$ cycloalkyl, or $CH_2(CHR_6)_wC_5$-$C_6$ cycloalkyl; and $R_1$ is H, F, Cl, Br, methoxy, or trifluoromethyl.

In another more specific subgeneric embodiment, this invention provides or contemplates a compound of formula IA-3, where R' is 1-phenyl, optionally substituted; $R_5$ is $C_4$-$C_6$ alkyl, $(CHR_6)_wC_5$-$C_6$ cycloalkyl, or $CH_2(CHR_6)_wC_5$-$C_6$ cycloalkyl; and $R_1$ is H, F, Cl, Br, methoxy, or trifluoromethyl.

In another more specific subgeneric embodiment, this invention provides or contemplates a compound of formula IA-3, where R' is 4-phenyl, optionally substituted; $R_5$ is $C_4$-$C_6$ alkyl, $(CHR_6)_wC_5$-$C_6$ cycloalkyl, or $CH_2(CHR_6)_wC_5$-$C_6$ cycloalkyl; and $R_1$ is H, F, Cl, Br, methoxy, or trifluoromethyl.

In another more specific subgeneric embodiment, this invention provides or contemplates a compound of formula IA-3, where R' is $CF_3$ or $C_1$-$C_3$ alkyl; $R_5$ is $C_4$-$C_6$ alkyl, $(CHR_6)_wC_5$-$C_6$ cycloalkyl, or $CH_2(CHR_6)_wC_5$-$C_6$ cycloalkyl; and $R_1$ is H, F, Cl, Br, methoxy, or trifluoromethyl.

In another subgeneric embodiment, this invention provides or contemplates a compound of formula IA-1, where $R_1$ and $R_2$, are, independently, H, CN, F, Cl, Br, $CH_2CN$, $OCH_3$, $CH_2OCH_3$, $CH_2CH_2OCH_3$, $CH_2OCH_2CH_3$; $CH_2F$, $CHF_2$, $CF_3$, $CF_2CF_3$, or $C_1$-$C_6$ alkyl and $R_5$ is $C_1$-$C_6$ alkyl or $CH_2(CHR_6)_wC_3$-$C_6$ cycloalkyl, where w=0, 1, or 2.

In another still more specific subgeneric embodiment, this invention provides or contemplates a compound of formula IA-1, $R_1$ is H, CN, F, Cl, Br, $CH_2CN$, $OCH_3$, $CH_2OCH_3$, $CH_2CH_2OCH_3$, $CH_2OCH_2CH_3$, $CH_2F$, $CHF_2$, $CF_3$, $CF_2CF_3$, or $C_1$-$C_6$ alkyl; $R_2$ is H, F, Cl, or methyl; $R_3$ is methyl or chloro; and $R_5$ is $C_1$-$C_6$ alkyl or $CH_2(CHR_6)_wC_3$-$C_6$ cycloalkyl, where $R_6$ is H or methyl and w=1 or 2.

In another more specific subgeneric embodiment, this invention provides or contemplates a compound of formula IA, where $R_5$ is Ar, $(CHR_6)_wAr$, $CH_2(CHR_6)_wAr$, or $(CHR_6)_wCH_2Ar$.

In another subgeneric embodiment, this invention provides or contemplates a compound of formula IA-2, where $R_5$ is Ar, $(CHR_6)_wAr$, $CH_2(CHR_6)_wAr$, or $(CHR_6)_wCH_2Ar_1$.

In another subgeneric embodiment, this invention provides or contemplates a compound of formula IA-3, where $R_5$ is Ar, $(CHR_6)_wAr$, $CH_2(CHR_6)_wAr$, or $(CHR_6)_wCH_2Ar$.

In another more specific subgeneric embodiment, this invention provides or contemplates compounds of formula IA-1, IA-2, IA-3, IA-4, or IA-5, where $R_1$ and $R_2$, are, independently, methyl, ethyl, F, Cl, $CF_3$, methoxy or methoxymethyl, R' is methyl, and $R_5$ is $C_4$-$C_6$ alkyl, $(CHR_6)_wC_5$-$C_6$ cycloalkyl, or $CH_2(CHR_6)_wC_5$-$C_6$ cycloalkyl.

In another more specific subgeneric embodiment, this invention provides or contemplates a compound of formula IA, where $R_5$ is $CR_6=CH$—$C_3$-$C_6$ cycloalkyl, $CH=CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another subgeneric embodiment, this invention provides or contemplates a compound of formula IA, where $R_5$ is haloalkyl.

In another subgeneric embodiment, this invention provides or contemplates a compound of formula IA-1, where $R_5$ is haloalkyl.

In another subgeneric embodiment, this invention provides or contemplates a compound of formula IA-2, where $R_5$ is haloalkyl.

In another subgeneric embodiment, this invention provides or contemplates a compound of formula IA-3, where $R_5$ is haloalkyl.

In another subgeneric embodiment, this invention provides or contemplates a compound of formula IA, where $R_5$ is methoxy alkyl.

In another subgeneric embodiment, this invention provides or contemplates a compound of formula IA, where $R_5$ is cyano alkyl.

In a more specific subgeneric embodiment, the invention provides or contemplates a compound of formula IA-4, where $R_5$ is halo alkyl.

In a more specific subgeneric embodiment, the invention provides or contemplates a compound of formula IA, where $R_5$ is $CH_2$-cycloalkyl or $CH_2CH_2$-cycloalkyl.

In a more specific subgeneric embodiment, the invention provides or contemplates a compound of formula IA-4, where $R_5$ is $CH_2$-cycloalkyl or $CH_2CH_2$-cycloalkyl.

In a more specific subgeneric embodiment, the invention provides or contemplates a compound of formula IA-5, where $R_5$ is $CH_2$-cycloalkyl or $CH_2CH_2$-cycloalkyl.

In another subgeneric embodiment, this invention provides or contemplates a compound of formula IA-1, where $R_3$ and $R_4$ are chloro, methoxy, or methyl and $R_5$ is $CH_2$-cycloalkyl.

In another subgeneric embodiment, this invention provides or contemplates a compound of formula IA-1, where $R_3$ and $R_4$ are chloro, methoxy, or methyl and $R_5$ is haloalkyl, hydroxyalkyl, or methoxyalkyl.

In a more specific subgeneric embodiment, this invention provides or contemplates a compound of formula IA-1, where $R_3$ and $R_4$ are chloro, methoxy, or methyl and $R_5$ is methoxy alkyl.

In another subgeneric embodiment, this invention provides or contemplates a compound of formula IA-2, where $R_3$ and $R_4$ are chloro, methoxy, or methyl and $R_5$ is chloroalkyl.

In another subgeneric embodiment, this invention provides or contemplates a compound of formula IA-2, where $R_3$ and $R_4$ are chloro, methoxy, or methyl and $R_5$ is methoxyalkyl.

In another subgeneric embodiment, this invention provides or contemplates a compound of formula IA-1, where $R_3$ and $R_4$ are both methyl and $R_5$ is 2-(2-halo cyclopentyl)ethyl.

In another subgeneric embodiment, this invention provides or contemplates a compound of formula IA-1, where $R_3$ and $R_4$ are both methyl and $R_5$ is 2-(2-furyl)ethyl.

In another subgeneric embodiment, this invention provides or contemplates a compound of formula IA-1, where $R_3$ and $R_4$ are both methyl and $R_5$ is 2-(2-tetrahydrofuryl)ethyl.

In another subgeneric embodiment, this invention provides or contemplates a compound of formula IA-1, where $R_3$ and $R_4$ are both methyl and $R_5$ is 2-phenyl ethyl.

In another subgeneric embodiment, this invention provides or contemplates a compound of formula IA-1, where $R_3$ and $R_4$ are both methyl and $R_5$ is 3-phenyl propyl.

In another subgeneric embodiment, this invention provides or contemplates a compound of formula IA-1, where $R_3$ and $R_4$ are both methyl and $R_5$ is 2-phenyl propyl.

In another more specific subgeneric embodiment, this invention provides or contemplates a compound of formula IA-1, where $R_5$ is $C_1$-$C_6$alkyl, $(CHR_6)C_3$-$C_6$ cycloalkyl, $(CHR_6)_wCH_2C_3$-$C_6$ cycloalkyl, or $CH_2(CHR_6)_wC_3$-$C_6$ cycloalkyl; R' is halogen or $C_1$-$C_3$ alkyl; and $R_1$ is halogen.

In another more specific subgeneric embodiment, this invention provides or contemplates a compound of formula IA-1, where $R_5$ is $C_1$-$C_6$alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; R' is halogen or $C_1$-$C_3$ alkyl; $R_2$ is H or halogen; and $R_1$ is halogen.

In another more specific subgeneric embodiment, this invention provides or contemplates a compound of formula IA-1, where $R_5$ is $C_1$-$C_6$alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; R' is phenyl, optionally substituted; $R_2$ is H or halogen; and $R_1$ is halogen.

In another more specific subgeneric embodiment, this invention provides or contemplates a compound of formula IA-1, where $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; R' is halogen or $C_1$-$C_3$ alkyl; $R_2$ is H or halogen; and $R_1$ is halogen.

In another more specific subgeneric embodiment, this invention provides or contemplates a compound of formula IA-2, where $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; R' is halogen or $C_1$-$C_3$ alkyl; and $R_1$ is halogen.

In another more specific subgeneric embodiment, this invention provides or contemplates a compound of formula IA-3, where $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl; R' is halogen or $C_1$-$C_3$ alkyl; and $R_1$ is halogen.

In another more specific subgeneric embodiment, this invention provides or contemplates a compound of formula IA, where $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA, where $R_5$ is Ar, $(CHR_6)_wAr$, $CH_2(CHR_6)_wAr$, or $(CHR_6)_wCH_2Ar_1$.

In another more specific subgeneric embodiment, this invention provides or contemplates a compound of formula IA-3, where $R_1$ is haloalkyl; $R_2$ is H or F; $R_3$ and $R_4$ are Cl, methoxy, or methyl; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of formula IA, where $R_1$ is $C_1$-$C_3$ alkyl, halogen, or haloalkyl; $R_2$ is H or F; $R_3$ and $R_4$ are H, methyl, or Cl; and $R_5$ is $CH_2CR_6$=$C_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_4$-$C_6$ alkyl, $C_2$-$C_6$ alkenyl, or $C_2$-$C_6$ alkynyl.

In another more specific subgeneric embodiment, this invention provides or contemplates a compound of formula IA-1, where $R_1$ is $C_1$-$C_3$ alkyl, halogen, or haloalkyl; $R_2$ is H or F; $R_3$ and $R_4$ are H, methyl, or Cl; and $R_5$ is $CH_2CR_6$=$C_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_4$-$C_6$ alkyl, $C_2$-$C_6$ alkenyl, or $C_2$-$C_6$ alkynyl.

In another more specific subgeneric embodiment, this invention provides or contemplates a compound of formula IA-3, where $R_1$ is $C_1$-$C_3$ alkyl, halogen, or haloalkyl; $R_2$ is H or F; $R_3$ and $R_4$ are H, methyl, or Cl; and $R_5$ is $CH_2CR_6$=$C_3$-$C_6$ cycloalkyl, $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_4$-$C_6$ alkyl, $C_2$-$C_6$ alkenyl, or $C_2$-$C_6$ alkynyl.

In another more specific subgeneric embodiment, this invention provides or contemplates a compound of formula IA-1, where $R_1$ is $C_1$-$C_3$ alkyl, halogen, or haloalkyl; $R_2$ is H or F; $R_3$ and $R_4$ are H, methyl, or Cl; and $R_5$ is $CH_2CR_6$=$C_3$-$C_6$ cycloalkyl, or $C_2$-$C_6$ alkyl.

In another more specific subgeneric embodiment, this invention provides or contemplates a compound of formula IA-3, where $R_1$ is $C_1$-$C_3$ alkyl, halogen, or haloalkyl; $R_2$ is H or F; $R_3$ and $R_4$ are H, methyl, or Cl; and $R_5$ is $CH_2CR_6$=$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-3, where $R_1$ is halogen or haloalkyl; $R_2$ is H or F; and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-3, where $R_1$ is halogen or haloalkyl; $R_2$ is H or F; and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-3, where $R_1$ is halogen or haloalkyl; $R_2$ is H or F; $R_3$ and $R_4$ are Cl, methoxy, or methyl; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of formula IA-3, where $R_1$ is halogen or haloalkyl; $R_2$ is H or F; and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-3, where $R_1$ is methyl, fluoro, or fluoroalkyl; $R_2$ is H or F; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of formula IA-3, where $R_1$ is Cl, F, or $CF_3$; $R_2$ is H or F; R' is H or $CH_3$; and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-3, where $R_1$ is Cl, F, or $CF_3$; $R_2$ is H or F; R' is H or $CH_3$; and $R_5$ is Ar, $(CHR_6)_w$Ar, $CH_2(CHR_6)_w$Ar, or $(CHR_6)_wCH_2$Ar.

In another more specific subgeneric embodiment, this invention provides or contemplates a compound of formula IA-4, where $R_3$ and $R_4$ are H, methyl, or Cl; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of formula IA-5, where $R_3$ and $R_4$ are H, methyl, or Cl; and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-1, where $R_3$ and $R_4$ are H, methyl, or Cl; and where $R_1$ and $R_2$, on adjacent carbons, form a six-membered ring.

In another more specific subgeneric embodiment, this invention provides or contemplates a compound of formula IA-1, where $R_3$ and $R_4$ are H, methyl, or Cl; where $R_5$ is $C_2$-$C_6$ alkyl, $CH_2$—$C_5$-$C_6$ cycloalkyl, $CH_2CH_2$—$C_5$-$C_6$ cycloalkyl, $CR_6$=CH—$C_3$-$C_6$ cycloalkyl, CH=$CR_6$—$C_3$-$C_6$ cycloalkyl, or $C_2$-$C_6$ alkenyl; and where $R_1$ and $R_2$, are on adjacent carbons, and are both other than H.

In another more specific subgeneric embodiment, this invention provides or contemplates a compound of formula IA-1, where $R_3$ and $R_4$ are H, methyl, or Cl; where $R_5$ is $C_2$-$C_6$ alkyl, $CH_2$—$C_5$-$C_6$ cycloalkyl, $CH_2CH_2$—$C_5$-$C_6$ cycloalkyl, $CR_6$=CH—$C_3$-$C_6$ cycloalkyl, CH=$CR_6$—$C_3$-$C_6$ cycloalkyl, or $C_2$-$C_6$ alkenyl; and where $R_1$ and $R_2$, on adjacent carbons, are both halogen.

In another more specific subgeneric embodiment, this invention provides or contemplates a compound of formula IA-1, where $R_3$ and $R_4$ are H, methyl, or Cl; where $R_5$ is $C_2$-$C_6$ alkyl, $CH_2$—$C_5$-$C_6$ cycloalkyl, $CH_2CH_2$—$C_5$-$C_6$ cycloalkyl, $CR_6$=CH—$C_3$-$C_6$ cycloalkyl, CH=$CR_6$—$C_3$-$C_6$ cycloalkyl, or $C_2$-$C_6$ alkenyl; and where $R_1$ and $R_2$, on adjacent carbons, are both fluorine.

In a more specific subgeneric embodiment, this invention provides or contemplates a compound of formula IA-1, where R' is F, methyl, or H; $R_3$ and $R_4$ are H, methyl, or Cl; and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of formula IA-1, where R' is F, methyl, or H; $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-1, where R' is halogen and $R_5$ is Ar, $(CHR_6)_w$Ar, $CH_2(CHR_6)_w$Ar, or $(CHR_6)_wCH_2Ar_1$.

In another subgeneric embodiment, this invention provides or contemplates a compound of formula IA-1, where $R_1$ and $R_2$ are on adjacent carbon atoms and are both other than H.

In a more specific subgeneric embodiment, this invention provides or contemplates a compound of formula IA-1, where $R_1$ and $R_2$, on adjacent carbon atoms are, independently trifluoromethyl or halogen; and where $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another subgeneric embodiment, this invention provides or contemplates a compound of formula IA-1, where $R_5$ is $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA-1, where $R_1$ is halogen and $R_2$ is H, or $R_1$ and $R_2$, on adjacent carbon atoms are, independently trifluoromethyl or halogen; and where $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another subgeneric embodiment, this invention provides or contemplates a compound of formula IA-1, where $R_5$ is Ar, $(CHR_6)_w$Ar, $CH_2(CHR_6)_w$Ar, or $(CHR_6)_wCH_2Ar_1$.

In another more specific subgeneric embodiment, this invention provides or contemplates a compound of formula IA-1, where $R_1$ is halogen or trifluoromethyl and $R_2$ is H, or $R_1$ and $R_2$, on adjacent carbon atoms are, independently trifluoromethyl or halogen; and where $R_5$ is Ar, $(CHR_6)_w$Ar, $CH_2(CHR_6)_w$Ar, or $(CHR_6)_wCH_2$Ar.

In another more specific subgeneric embodiment, this invention provides or contemplates a compound of formula IA, where X is S, q=1, Y is O, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of formula IA, where X is S, q=1, Y is O, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another more specific subgeneric embodiment, this invention provides or contemplates a compound of formula IA, where X is S, q=1, Y is O, and $R_5$ is Ar, $(CHR_6)_w$Ar, $CH_2(CHR_6)_w$Ar, or $(CHR_6)_wCH_2$Ar.

In another more specific subgeneric embodiment, this invention provides or contemplates a compound of formula IA, where X is S, q=zero, and $R_5$ is $C_1$-$C_6$ alkyl, $(CHR_6)_wC_3$-$C_6$ cycloalkyl, $(CHR_6)_wCH_2C_3$-$C_6$ cycloalkyl, or $CH_2(CHR_6)_wC_3$-$C_6$ cycloalkyl.

In another more specific subgeneric embodiment, this invention provides or contemplates a compound of formula IA, where X is S, q=zero, and $R_5$ is $CR_6$=CH—$C_3$-$C_6$ cycloalkyl, CH=$CR_6$—$C_3$-$C_6$ cycloalkyl, $(CHR_6)_wC_5$-$C_6$ cycloalkenyl, $CH_2(CHR_6)_wC_5$-$C_6$ cycloalkenyl, $C_2$-$C_6$ alkenyl, or $C_2$-$C_6$ alkynyl.

In another subgeneric embodiment, this invention provides or contemplates a compound of formula IA-2 where $R_5$ is $C_1$-$C_6$ alkyl or $(CHR_6)_wC_3$-$C_6$ cycloalkyl.

In another subgeneric embodiment, this invention provides or contemplates a compound of formula IA-3, where $R_5$ is $C_1$-$C_6$ alkyl or $(CHR_6)_w C_3$-$C_6$ cycloalkyl.

In another subgeneric embodiment, this invention provides or contemplates a compound of formula IA-2, where $R_1$ is halogen or trifluoromethyl and $R_2$ is H or $R_1$ and $R_2$, on adjacent carbon atoms, are, independently, halogen or trifluoromethyl; and $R_5$ is $C_1$-$C_6$ alkyl or $(CHR_6)_w C_3$-$C_6$ cycloalkyl.

In another subgeneric embodiment, this invention provides or contemplates a compound of formula IA-3, where $R_1$ is halogen or trifluoromethyl and $R_2$ is H or $R_1$ and $R_2$, on adjacent carbon atoms, are, independently, halogen or trifluoromethyl; and $R_5$ is $C_1$-$C_6$ alkyl or $(CHR_6)_w C_3$-$C_6$ cycloalkyl.

In another more specific subgeneric embodiment, this invention provides or contemplates a compound of formula IA-2, where $R_1$ and $R_2$ are, independently, methyl, methoxy, trifluoromethyl, F, Cl, or H; and $R_5$ is $C_1$-$C_6$ alkyl or $(CHR_6)_w C_3$-$C_6$ cycloalkyl.

In another more specific subgeneric embodiment, this invention provides or contemplates a compound of formula IA-3, where $R_1$ and $R_2$ are, independently, methyl, methoxy, trifluoromethyl, F, Cl, or H; R' is H; and $R_5$ is $C_1$-$C_6$ alkyl or $(CHR_6)_w C_3$-$C_6$ cycloalkyl.

In another subgeneric embodiment, this invention provides or contemplates a compound of formula IA-1 or IA-2 or IA-3, where $R_1$ is halogen, $C_1$-$C_6$ alkyl, mono-halo $C_1$-$C_6$ alkyl, CN, di-halo $C_1$-$C_6$ alkyl, $CF_3$, CN, or O—$C_1$-$C_6$ alkyl; R' is methyl or ethyl; and $R_5$ is $C_5$-$C_6$ alkyl or $CH_2$—$C_3$-$C_6$ cycloalkyl.

In another more specific subgeneric embodiment, this invention provides or contemplates a compound of formula IA-1 or IA-2 or IA-3, where $R_1$ is H, halogen, cyano, $CF_3$, or methoxy, $R_2$ is H, F, or methyl, R' is H, halogen, methyl, ethyl, or methoxy, and $R_5$ is $C_5$-$C_6$ alkyl or $CH_2$—$C_3$-$C_6$ cycloalkyl.

In another subgeneric embodiment, this invention provides or contemplates a compound of formula IA, where $R_1$ is F, Cl, or $CF_3$; $R_2$ is H; and R' is halogen, methyl, ethyl, or methoxy; $R_3$ and $R_4$ are H, methyl, or Cl; and $R_5$ is $C_5$-$C_6$ alkyl or $CH_2$—$C_3$-$C_6$ cycloalkyl.

In another subgeneric embodiment, this invention provides or contemplates a compound of formula IA, where $R_1$ is halogen or $CF_3$; $R_2$ is H, F, or methyl, R' is phenyl; $R_3$ and $R_4$ are H, methyl, or Cl; and $R_5$ is $C_5$-$C_6$ alkyl or $CH_2$—$C_5$-$C_6$ cycloalkyl.

In another subgeneric embodiment, this invention provides or contemplates a compound of formula IA, where $R_1$ is halogen or $CF_3$; $R_2$ is H, F, or methyl, R' is halophenyl; $R_3$ and $R_4$ are H, methyl, or Cl; and $R_5$ is $C_5$-$C_6$ alkyl or $CH_2$—$C_5$-$C_6$ cycloalkyl.

In another subgeneric embodiment, this invention provides or contemplates a compound of formula IA, where $R_1$ is $NH_2$, NH—$C_1$-$C_6$ alkyl; $N(C_1$-$C_6$ alkyl)-$C_1$-$C_6$ alkyl, NHC(=O) $C_1$-$C_6$ alkyl, C(=O)N($CH_3$)$_2$, C(=O)N(Et)$_2$, C(=O)NH$_2$, C(=O)NH—$C_1$-$C_6$ alkyl, $SO_2NH_2$, $NHSO_2$—$C_1$-$C_6$ alkyl.

In a more specific subgeneric embodiment, this invention provides or contemplates a compound of formula IA where $R_1$ is $NH_2$, NH—$C_1$-$C_6$ alkyl; or $N(C_1$-$C_6$ alkyl)-$C_1$-$C_6$ alkyl; and $R_2$ is H or halogen.

In another more specific subgeneric embodiment, this invention provides or contemplates a compound of formula IA where $R_1$ is NHC(=O)$C_1$-$C_6$ alkyl, C(=O)N($CH_3$)$_2$, C(=O)N(Et)$_2$, C(=O)NH$_2$, or C(=O)NH—$C_1$-$C_6$ alkyl.

In another more specific subgeneric embodiment, this invention provides or contemplates a compound of formula IA-1 where $R_1$ is NHC(=O)$C_1$-$C_6$ alkyl, C(=O)N($CH_3$)$_2$, C(=O)N(Et)$_2$, C(=O)NH$_2$, or C(=O)NH—$C_1$-$C_6$ alkyl.

In another more specific subgeneric embodiment, this invention provides or contemplates a compound of formula IA-1 where $R_1$ is $SO_2NH_2$ or $NHSO_2$—$C_1$-$C_6$ alkyl.

In another more specific subgeneric embodiment, this invention provides or contemplates a compound of formula IA-2 where $R_1$ is $SO_2NH_2$ or $NHSO_2$—$C_1$-$C_6$ alkyl.

In another subgeneric embodiment, this invention provides or contemplates a compound of formula IA, where $R_1$ is C(=O)O$C_1$-$C_6$ alkyl, OC(=O)$C_1$-$C_6$ alkyl, O$C_1$-$C_6$ alkyl, or S$C_1$-$C_6$ alkyl.

In another subgeneric embodiment, this invention provides or contemplates a compound of formula IA, where $R_1$ is $(CH_2)_m C_3$-$C_6$ cycloalkenyl, $C_2$-$C_6$ alkenyl, or $C_2$-$C_6$ alkynyl.

In another subgeneric embodiment, this invention provides or contemplates a compound of formula IA, where $R_1$ is $CH_2OCH_3$, $CH_2OCH_2CH_3$, O$C_1$-$C_6$ alkyl, or S$C_1$-$C_6$ alkyl.

In another more specific subgeneric embodiment, this invention provides or contemplates a compound of formula IA-1, where $R_1$ is C(=O)O$C_1$-$C_6$ alkyl, OC(=O)$C_1$-$C_6$ alkyl, O$C_1$-$C_6$ alkyl, or S$C_1$-$C_6$ alkyl.

In another subgeneric embodiment, this invention provides or contemplates a compound of formula IA-1, where $R_1$ is $CH_2OCH_3$, $CH_2OCH_2CH_3$, O$C_1$-$C_6$ alkyl, or S$C_1$-$C_6$ alkyl.

In another more specific subgeneric embodiment, this invention provides or contemplates a compound of formula IA-1, where $R_1$ is C(=O)O$C_1$-$C_6$ alkyl, OC(=O)$C_1$-$C_6$ alkyl, O$C_1$-$C_6$ alkyl, or S$C_1$-$C_6$ alkyl; $R_2$ is H, F, or methyl, R' is halogen or methyl; and $R_5$ is $C_5$-$C_6$ alkyl or $CH_2$—$C_5$-$C_6$ cycloalkyl.

In another more specific subgeneric embodiment, this invention provides or contemplates a compound of formula IA-1, where $R_1$ is $NH_2$, NH—$C_1$-$C_6$ alkyl; or $N(C_1$-$C_6$ alkyl)-$C_1$-$C_6$ alkyl; $R_2$ is H, F, or methyl, R' is halogen or methyl; and $R_5$ is $C_5$-$C_6$ alkyl or $CH_2$—$C_5$-$C_6$ cycloalkyl.

In another more specific subgeneric embodiment, this invention provides or contemplates a compound of formula IA-1, where $R_1$ is NHC(=O)$C_1$-$C_6$ alkyl, C(=O)N($CH_3$)$_2$, C(=O)N(Et)$_2$, C(=O)NH$_2$, C(=O)NH—$C_1$-$C_6$ alkyl, $SO_2NH_2$, or $NHSO_2$—$C_1$-$C_6$ alkyl; $R_2$ is H, F, or methyl, R' is halogen or methyl; and $R_5$ is $C_5$-$C_6$ alkyl or $CH_2$—$C_5$-$C_6$ cycloalkyl.

In another subgeneric embodiment, this invention provides or contemplates a compound of formula IA, where $R_1$ is $C_2$-$C_6$ alkynyl, optionally substituted.

In another subgeneric embodiment, this invention provides or contemplates a compound of formula IA, where $R_1$ and $R_2$ form a fused, nitrogen-containing ring.

In another subgeneric embodiment, this invention provides or contemplates a compound of formula IA, where $R_1$ and $R_2$ form a fused, oxygen-containing ring.

In another subgeneric embodiment, this invention provides or contemplates a compound of formula IA, where $R_1$ and $R_2$ form a fused thiazolo or isothiazolo group.

In another subgeneric embodiment, this invention provides or contemplates a compound of formula IA, where $R_1$ and $R_2$ form a fused cyclopentane, optionally substituted.

In another subgeneric embodiment, this invention provides or contemplates a compound of formula IA, where $R_1$ and $R_2$ form a fused cyclohexane, optionally substituted.

In another subgeneric embodiment, this invention provides or contemplates a compound of formula IA-1 or IA-2, where $R_1$ and $R_2$ form a fused, nitrogen-containing ring.

In another subgeneric embodiment, this invention provides or contemplates a compound of formula IA-1 or IA-2, where $R_1$ and $R_2$ form a fused, oxygen-containing ring.

In another subgeneric embodiment, this invention provides or contemplates a compound of formula IA-1 or IA-2, where $R_1$ and $R_2$ form a fused thiazolo or isothiazolo group.

In another subgeneric embodiment, this invention provides or contemplates a compound of formula IA-1 or IA-2, where $R_1$ and $R_2$ form a fused cyclopentane, optionally substituted.

In another subgeneric embodiment, this invention provides or contemplates a compound of formula IA-1 or IA-2, where $R_1$ and $R_2$ form a fused cyclohexane, optionally substituted.

In another subgeneric embodiment, this invention provides or contemplates a compound of formula IA-1 or IA-2, where $R_1$ and $R_2$ form a fused, nitrogen-containing ring; and $R_5$ is $C_5$-$C_6$ alkyl or $CH_2$—$C_5$-$C_6$ cycloalkyl.

In another subgeneric embodiment, this invention provides or contemplates a compound of formula IA-1 or IA-2, where $R_1$ and $R_2$ form a fused, oxygen-containing ring; and $R_5$ is $C_5$-$C_6$ alkyl or $CH_2$—$C_5$-$C_6$ cycloalkyl.

In another subgeneric embodiment, this invention provides or contemplates a compound of formula IA-1 or IA-2, where $R_1$ and $R_2$ form a fused thiazolo or isothiazolo group; and $R_5$ is $C_5$-$C_6$ alkyl or $CH_2$—$C_5$-$C_6$ cycloalkyl.

In another subgeneric embodiment, this invention provides or contemplates a compound of formula IA-1 or IA-2, where $R_1$ and $R_2$ form a fused cyclopentane, optionally substituted; and $R_5$ is $C_5$-$C_6$ alkyl or $CH_2$—$C_5$-$C_6$ cycloalkyl.

In another subgeneric embodiment, this invention provides or contemplates a compound of formula IA-1 or IA-2, where $R_1$ and $R_2$ form a fused cyclohexane, optionally substituted; and $R_5$ is $C_5$-$C_6$ alkyl or $CH_2$—$C_5$-$C_6$ cycloalkyl.

In another more specific subgeneric embodiment, this invention provides or contemplates a compound of formula IA-1, where $R_1$ is halogen; $R_2$ is H, F, or methyl, R' is halogen or methyl; and $R_5$ is $C_5$-$C_6$ alkyl or $CH_2$—$C_5$-$C_6$ cycloalkyl.

In another more specific subgeneric embodiment, this invention provides or contemplates a compound of formula IA-1, where $R_1$ is halogen; $R_2$ is H, F, or methyl, R' is 2-(dimethylamino)ethyl; and $R_5$ is $C_5$-$C_6$ alkyl or $CH_2$—$C_5$-$C_6$ cycloalkyl.

In another more specific subgeneric embodiment, this invention provides or contemplates a compound of formula IA-1, where $R_1$ is halogen; $R_2$ is H, halogen, or methyl; R' is H; and $R_5$ is $C_5$-$C_6$ alkyl or $CH_2$—$C_5$-$C_6$ cycloalkyl.

In another more specific subgeneric embodiment, this invention provides or contemplates a compound of formula IA-2, where $R_1$ is halogen; $R_2$ is H or methyl, R' is halogen or methyl; and $R_5$ is $C_5$-$C_6$ alkyl or $CH_2$—$C_5$-$C_6$ cycloalkyl.

$C(=O)OC_1$-$C_6$ alkyl, $OC(=O)C_1$-$C_6$ alkyl, $OC_1$-$C_6$ alkyl
In another more specific subgeneric embodiment, this invention provides or contemplates a compound of formula IA-1,
In another more specific subgeneric embodiment, this invention provides or contemplates a compound of formula IA-1, where $R_1$ is trifluoromethyl; $R_2$ is H or methyl, R' is halogen or methyl; and $R_5$ is $C_5$-$C_6$ alkyl or $CH_2$—$C_5$-$C_6$ cycloalkyl.

In another more specific subgeneric embodiment, this invention provides or contemplates a compound of formula IA-2, where $R_1$ where $R_1$ is trifluoromethyl; $R_2$ is H or methyl, R' is halogen or methyl; and $R_5$ is $C_5$-$C_6$ alkyl or $CH_2$—$C_5$-$C_6$ cycloalkyl.

In another more specific subgeneric embodiment, this invention provides or contemplates a compound of formula IA-3, where $R_1$ where $R_1$ is trifluoromethyl; $R_2$ is H or methyl, R' is halogen or methyl; and $R_5$ is $C_5$-$C_6$ alkyl or $CH_2$—$C_5$-$C_6$ cycloalkyl.

In another more specific subgeneric embodiment, this invention provides or contemplates a compound of formula IA-4 or IA-5, where $R_1$ where $R_1$ is trifluoromethyl; $R_2$ is H or methyl, R' is halogen or methyl; and $R_5$ is $C_5$-$C_6$ alkyl or $CH_2$—$C_5$-$C_6$ cycloalkyl.

In another more specific subgeneric embodiment, this invention provides or contemplates a compound of formula IA-2, where $R_1$ is trifluoromethyl; $R_2$ is F; R' is halogen or methyl; and $R_5$ is $C_5$-$C_6$ alkyl or $CH_2$—$C_5$-$C_6$ cycloalkyl.

In another subgeneric embodiment, this invention provides or contemplates a compound of formula IA, where $R_1$ or $R_5$ is $CH_2Ar$ or $CH_2CH_2$—Ar, where Ar is phenyl, pyridyl, pyrrolyl, imidazolyl, oxazolyl, or thiazolyl.

In another subgeneric embodiment, this invention provides or contemplates a compound of formula IA, where $R_1$ is F.

In another subgeneric embodiment, this invention provides or contemplates a compound of formula IA, where $R_1$ is Cl.

In another subgeneric embodiment, this invention provides or contemplates a compound of formula IA, where $R_1$ is Br.

In another subgeneric embodiment, this invention provides or contemplates a compound of formula IA-1, where $R_1$ is F.

In another subgeneric embodiment, this invention provides or contemplates a compound of formula IA-1, where $R_1$ is Cl.

In another subgeneric embodiment, this invention provides or contemplates a compound of formula IA-1, where $R_1$ is Br.

In another subgeneric embodiment, this invention provides or contemplates a compound of formula IA-1, where $R_1$ is F and $R_2$ is H, $OCH_3$, or F.

In another subgeneric embodiment, this invention provides or contemplates a compound of formula IA-1, where $R_1$ is F; $R_3$ and $R_4$ are both methyl; and R' is H.

In another subgeneric embodiment, this invention provides or contemplates a compound of formula IA-1, where $R_1$ is $CF_3$; $R_3$ and $R_4$ are both methyl; and R' is H.

In another subgeneric embodiment, this invention provides or contemplates a compound of formula IA, where $R_1$ and $R_2$ are both F.

In another subgeneric embodiment, this invention provides or contemplates a compound of formula IA, where $R_1$ is mono-, di-, or tri-halomethyl.

In another subgeneric embodiment, this invention provides or contemplates a compound of formula IA, where $R_1$ is $CH_2F$, $CHF_2$, or $CF_3$.

In another subgeneric embodiment, this invention provides or contemplates a compound of formula IA, where $R_1$ is $CH_2Cl$.

In another subgeneric embodiment, this invention provides or contemplates a compound of formula IA, where $R_1$ is $CH_2Br$.

In another subgeneric embodiment, this invention provides or contemplates a compound of formula IA-1, where $R_1$ and $R_2$ are both F; $R_3$ and $R_4$ are both methyl; and R' is H.

In another subgeneric embodiment, this invention provides or contemplates a compound of formula IA-2, where $R_1$ is F.

In another subgeneric embodiment, this invention provides or contemplates a compound of formula IA-2, where $R_1$ and $R_2$ are both F.

In another subgeneric embodiment, this invention provides or contemplates a compound of formula IA-3, where $R_1$ is F.

In another subgeneric embodiment, this invention provides or contemplates a compound of formula IA-3, where $R_1$ and $R_2$ are both F.

In another subgeneric embodiment, this invention provides or contemplates a compound of formula IA, where $R_1$ or $R_5$ is $CH_2Ar$ or $CH_2CH_2$—Ar, where Ar is isoxazolyl or isothiazolyl.

In another subgeneric embodiment, this invention provides or contemplates a compound of formula IA, where $R_1$ or $R_5$ is $CH_2Ar$ or $CH_2CH_2$—Ar, where Ar is quinolyl or isoquinolyl.

In another subgeneric embodiment, this invention provides or contemplates a compound of formula IA, where $R_1$ or $R_5$ is $CH_2Ar$ or $CH_2CH_2$—Ar, where Ar is pyrimidyl or purinyl.

In another subgeneric embodiment, this invention provides or contemplates a compound of formula IA, where $R_1$ or $R_5$ is $CH_2Ar$ or $CH_2CH_2$—Ar, where Ar is indolyl, isoindolyl, or benzimidazolyl.

In a more specific embodiment, this invention provides or contemplates a compound of formula IA, where $R_1$ or $R_5$ is $CH_2Ar$ or $CH_2CH_2$—Ar, where Ar is halo phenyl.

In another more specific embodiment, this invention provides or contemplates a compound of formula IA, where $R_1$ or $R_5$ is $CH_2Ar$ or $CH_2CH_2$—Ar, where Ar is dihalophenyl or dihalopyridyl.

In another more specific embodiment, invention provides or contemplates a compound of formula IA, where $R_1$ or $R_5$ is $CH_2Ar$ or $CH_2CH_2$—Ar, where Ar is mono- or di-halothienyl, mono- or di-halofuryl, mono- or di-halobenzothienyl, or mono- or di-halobenzofuryl.

In another more specific embodiment, this invention provides or contemplates a compound of formula IA, where $R_1$ or $R_5$ is $CH_2Ar$ or $CH_2CH_2$—Ar, where Ar is o-, m-, or p-xylyl or o-, m-, or p-anisyl.

In another more specific embodiment, this invention provides or contemplates a compound of formula IA, where $R_1$ or $R_5$ is $CH_2Ar$ or $CH_2CH_2$—Ar, where Ar is m- or p-cyanophenyl or m- or p-cyanomethyl phenyl.

In another subgeneric embodiment, this invention provides or contemplates a compound of formula IA, in which $R_3$ and $R_4$ are halogen, $CF_3$, or $C_1$-$C_3$ alkyl and $R_5$ is $C_1$-$C_6$ alkyl, where the alkyl group is substituted with one or two groups selected, independently, from OH, OMe, OEt, F, $CF_3$, Cl, or CN.

In another subgeneric embodiment, this invention provides or contemplates a compound of formula IA, in which $R_3$ and $R_4$ are halogen, $CF_3$, $OCF_3$, $C_1$-$C_3$ alkyl, or $OC_1$-$C_3$ alkyl, and $R_5$ is $(CH_2)_w C_3$-$C_6$ cycloalkyl, where w is 1 or 2, where the cycloalkyl group is substituted with Me, OH, OMe, OEt, F, $CF_3$, Cl, or CN.

In a more specific subgeneric embodiment, this invention provides or contemplates a compound of formula IA-1, in which $R_3$ and $R_4$ are halogen, $CF_3$, or $C_1$-$C_3$ alkyl, and $R_5$ is $(CH_2)_w$—$C_5$-$C_6$ cycloalkyl, optionally substituted, or $(CH_2)_w$—$C_5$-$C_6$ heterocycloalkyl, optionally substituted.

In another more specific embodiment, this invention provides or contemplates a compound of formula IA-1, where $R_1$ is $CH_2$-phenyl or $CH_2CH_2$-phenyl.

In another more specific embodiment, this invention provides or contemplates a compound of formula IA-1, where $R_1$ is Ar, $CH_2Ar$ or $CH_2CH_2$—Ar, where Ar is 3,5-dichlorophenyl or 3,5-difluorophenyl.

In a more specific embodiment, this invention provides or contemplates a compound of formula IA-1, where $R_5$ is Ar, $(CHR_6)_w Ar$, $CH_2(CHR_6)_w Ar$, or $(CHR_6)_w CH_2 Ar$, where Ar is phenyl or pyridyl; $R_3$ and $R_4$ are H or $C_1$-$C_6$ alkyl, unsubstituted or substituted with one or two groups selected from OH, OMe; and $R_6$ is CN, $CH_2CN$, or halogen.

In another subgeneric embodiment, this invention provides or contemplates a compound of formula IA-1, where $R_5$ is Ar, $(CHR_6)_w Ar$, $CH_2(CHR_6)_w Ar$, or $(CHR_6)_w CH_2 Ar$, where Ar is phenyl or pyridyl; and $R_1$ is F, $CH_2F$, $CHF_2$, $CF_3$, or $CF_2CF_3$.

In a more specific embodiment, this invention provides or contemplates a compound of formula IA-1, where $R_5$ is Ar, $(CHR_6)_w Ar$, $CH_2(CHR_6)_w Ar$, or $(CHR_6)_w CH_2 Ar$, where Ar is phenyl or pyridyl, and $R_1$ is $OC_1$-$C_6$ alkyl or $C(=O)C_1$-$C_6$ alkyl.

In a more specific embodiment, this invention provides or contemplates a compound of formula IA-1, where $R_5$ is Ar, $(CHR_6)_w Ar$, $CH_2(CHR_6)_w Ar$, or $(CHR_6)_w CH_2 Ar$, where Ar is phenyl or pyridyl, and $R_1$ is $C(=O)OC_1$-$C_6$ alkyl or $OC(=O)C_1$-$C_6$ alkyl.

In a more specific embodiment, this invention provides or contemplates a compound of formula IA-1, where $R_5$ is Ar, $(CHR_6)_w Ar$, $CH_2(CHR_6)_w Ar$, or $(CHR_6)_w CH_2 Ar$, where Ar is phenyl or pyridyl, $R_1$ is $C_2$-$C_6$ alkenyl or $C_2$-$C_6$ alkynyl, q is 1, and X and Y are both O.

In another more specific embodiment, this invention provides or contemplates a compound of formula IA-1, where $R_5$ is Ar, $(CHR_6)_w Ar$, $CH_2(CHR_6)_w Ar$, or $(CHR_6)_w CH_2 Ar$, Ar is phenyl or pyridyl, and $R_1$ is $SC_1$-$C_6$ alkyl.

In a more specific embodiment, this invention provides or contemplates a compound of formula IA-1, where $R_5$ is Ar, $(CHR_6)_w Ar$, $CH_2(CHR_6)_w Ar$, or $(CHR_6)_w CH_2 Ar$, where Ar is phenyl or pyridyl, $R_3$ and $R_4$ are H, Cl, methoxy, or $C_1$-$C_3$ alkyl, and $R_1$ is $C_1$-$C_6$ alkyl.

In a more specific embodiment, this invention provides or contemplates a compound of formula IA-2, where $R_5$ is Ar, $(CHR_6)_w Ar$, $CH_2(CHR_6)_w Ar$, or $(CHR_6)_w CH_2 Ar$, where Ar is phenyl or pyridyl; $R_3$ and $R_4$ are H, Cl, methoxy, or $C_1$-$C_2$ alkyl, unsubstituted or substituted with one or two groups selected from OH, OMe; and $R_1$ is CN, $CH_2CN$, or halogen.

In another subgeneric embodiment, this invention provides or contemplates a compound of formula IA-2, where $R_5$ is Ar, $(CHR_6)_w Ar$, $CH_2(CHR_6)_w Ar$, or $(CHR_6)_w CH_2 Ar$, where Ar is phenyl or pyridyl; and $R_1$ is F, $CH_2F$, $CHF_2$, $CF_3$, or $CF_2CF_3$.

In a more specific embodiment, this invention provides or contemplates a compound of formula IA-1, where $R_5$ is Ar, $(CHR_6)_w Ar$, $CH_2(CHR_6)_w Ar$, or $(CHR_6)_w CH_2 Ar$, where Ar is phenyl or pyridyl, and $R_1$ is $OC_1$-$C_6$ alkyl or $C(=O)C_1$-$C_6$ alkyl.

In a more specific embodiment, this invention provides or contemplates a compound of formula IA-2, where $R_5$ is Ar, $(CHR_6)_w Ar$, $CH_2(CHR_6)_w Ar$, or $(CHR_6)_w CH_2 Ar$, where Ar is phenyl or pyridyl, and $R_1$ is $OC_1$-$C_6$ alkyl or $C(=O)C_1$-$C_6$ alkyl.

In a more specific embodiment, this invention provides or contemplates a compound of formula IA-3, where $R_5$ is Ar, $(CHR_6)_w Ar$, $CH_2(CHR_6)_w Ar$, or $(CHR_6)_w CH_2 Ar$, where Ar is phenyl or pyridyl, and $R_1$ is $OC_1$-$C_6$ alkyl or $C(=O)C_1$-$C_6$ alkyl.

In a more specific embodiment, this invention provides or contemplates a compound of formula IA-3, where R' is phenyl or methoxy, $R_2$ is H, and $R_5$ is Ar, $(CHR_6)_w Ar$, $CH_2(CHR_6)_w Ar$, or $(CHR_6)_w CH_2 Ar$, where Ar is phenyl or pyridyl, and $R_1$ is $C(=O)OC_1$-$C_6$ alkyl or $OC(=O)C_1$-$C_6$ alkyl.

In a more specific embodiment, this invention provides or contemplates a compound of formula IA-2, where $R_5$ is Ar, $(CHR_6)_w Ar$, $CH_2(CHR_6)_w Ar$, or $(CHR_6)_w CH_2 Ar$, Ar is phenyl or pyridyl, and $R_1$ is $SC_1$-$C_6$ alkyl.

In a more specific embodiment, this invention provides or contemplates a compound of formula IA-2, where $R_5$ is Ar, $(CHR_6)_w Ar$, $CH_2(CHR_6)_w Ar$, or $(CHR_6)_w CH_2 Ar$, where Ar is phenyl or pyridyl, $R_3$ and $R_4$ are H or $C_1$-$C_3$ alkyl, and $R_1$ is $C_1$-$C_6$ alkyl.

In another embodiment, this invention provides or contemplates a method of treating or preventing a disease, disorder, or condition that is affected by modulation of potassium ion channels in a patient comprising administration of a compound of formula IA in an amount of up to 2000 mg per day.

In another embodiment, this invention provides or contemplates a method of treating or preventing a disease, disorder, or condition that is affected by modulation of potassium ion channels in a patient comprising administration of a compound of formula IA in an amount of from about 10 mg to about 2000 mg per day.

In a more specific embodiment, this invention provides or contemplates a method of treating or preventing a disease, disorder, or condition that is affected by modulation of potassium ion channels in a patient comprising administration of a compound of formula IA-1 in an amount of up to about 2000 mg per day.

In a more specific embodiment, this invention provides or contemplates a method of treating or preventing a seizure disorder in a patient comprising administration of a compound of formula IA in an amount of up to about 2000 mg per day.

In another embodiment, this invention provides or contemplates a method of treating or preventing a seizure disorder in a patient comprising administration of a compound of formula IA in an amount of from about 10 mg per day to about 2000 mg per day.

In another embodiment, this invention provides or contemplates a method of treating or preventing a seizure disorder in a patient comprising administration of a compound of formula IA in an amount of from about 300 mg per day to about 2000 mg per day.

In another embodiment, this invention provides or contemplates a method of treating or preventing a seizure disorder in a patient comprising administration of a compound of formula IA in an amount of from about 300 mg per day to about 1200 mg per day.

In another more specific embodiment, this invention provides or contemplates a method of treating or preventing a seizure disorder in a patient comprising administration of a compound of formula IA-1 in an amount of up to 2000 mg per day.

In another embodiment, this invention provides or contemplates a method of treating or preventing a seizure disorder in a patient comprising administration of a compound of formula IA-1 in an amount of from about 10 mg per day to about 2000 mg per day.

In another embodiment, this invention provides or contemplates a method of treating or preventing a seizure disorder in a patient comprising administration of a compound of formula IA-1 in an amount of from about 300 mg per day to about 2000 mg per day.

In another embodiment, this invention provides or contemplates a method of treating or preventing a seizure disorder in a patient comprising administration of a compound of formula IA-1 in an amount of from about 300 mg per day to about 1200 mg per day.

DETAILED DESCRIPTION OF INVENTION

As contemplated by this invention, compounds of formula IA are designed for oral or intravenous dosing of up to 2000 mg per day. Yet the high activities of many of these compounds indicate that dosing of less than 1200 mg per day—the current anticipated dosing level of retigabine in adults—is possible. Thus, this invention comprises tablets, capsules, solutions, and suspensions of compounds of formula IA which are formulated for oral administration. Similarly, solutions and suspensions suitable for oral pediatric administration, comprising, in addition to compounds of formula IA, a syrup such as sorbitol or propylene glycol, among many other examples, are also contemplated. More specifically, solutions and suspensions comprising, in addition to compounds of formula IA, a syrup such as sorbitol or propylene glycol, along with colorants and flavorings suitable for oral pediatric administration, are also contemplated. Additionally, both chewable and non-chewable tablets comprising compounds of formula IA, along with pharmaceutically acceptable tabletting agents and other pharmaceutically acceptable carriers and excipients, are also contemplated. As used herein, the term pharmaceutically acceptable carrier comprises such excipients, binders, lubricants, tabletting agents, disintegrants, preservatives, anti-oxidants, flavours and colourants as are typically used in the art of formulation of pharmaceuticals. Examples of such agents include—but are not limited to—starch, calcium carbonate, dibasic calcium phosphate, dicalcium phosphate, microcrystalline cellulose, hydroxypropylcellulose, hydroxypropylmethylcellulose lactose, polyethylene glycols, polysorbates, glycols, safflower oil, sesame oil, soybean oil, and Povidone. Additionally, disintegrants such as sodium starch glycolate; lubricants such as magnesium stearate, stearic acid, and $SiO_2$; and solubility enhancers such as cyclodextrins, among a great many other examples for each group, are contemplated. Such materials and the methods of using them are well known in the pharmaceutical art. Additional examples are provided in Kibbe, *Handbook of Pharmaceutical Excipients*, London, Pharmaceutical Press, 2000.

As used herein, the term "pharmaceutically acceptable acid salts" refers to acid addition salts formed from acids which provide non-toxic anions. The pharmaceutically acceptable anions include, but are not limited to, acetate, aspartate, benzoate, bicarbonate, carbonate, bisulfate, sulfate, chloride, bromide, benzene sulfonate, methyl sulfonate, phosphate, acid phosphate, lactate, maleate, malate, malonate, fumarate, lactate, tartrate, borate, camsylate, citrate, edisylate, esylate, formate, fumarate, gluceptate, glucuronate, gluconate oxalate, palmitate, pamoate, saccharate, stearate, succinate, tartrate, tosylate and trifluoroacetate salts, among a great many other examples. Hemi-salts, including but not limited to hemi-sulfate salts, are likewise contemplated.

For a review on suitable salts, see "Handbook of Pharmaceutical Salts: Properties, Selection, and Use" by Stahl and Wermuth (Wiley-VCH, Weinheim, Germany, 2002).

As is well known, pharmaceutically acceptable salts of compounds of formula I may be prepared by reaction of a compound of formula I with the desired acid; by removal of a protecting group from a suitable precursor of the compound of formula I or by ring-opening a suitable cyclic precursor, for example, a lactone or lactam, using the desired acid or base; and by conversion of one salt of the compound of formula I to another by reaction with an appropriate acid or base or by passage through an appropriate ion-exchange column.

As used herein, the term "pharmaceutically acceptable solvate" refers to describe a molecular complex comprising the compound of the invention and a stoichiometric amount of one or more pharmaceutically acceptable solvent molecules, including but not limited to water and ethanol. Thus, the term solvate includes a hydrate as one example and an ethanolate as another example.

As used herein, modulation of ion channels refers to activating the ion channels, to affecting the kinetics of opening and closing of the ion channels, or to causing any change in the channel open probability of the ion channels.

Preparation of Compounds

General Strategy

Section I. The preparation of compounds of formula VI is outlined in Scheme 1, in which, for convenience, a substituted tetrahydroisoquinoline,

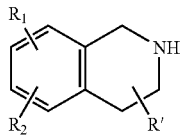

is symbolized by structure V.

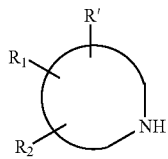

V

Such substituted tetrahydroisoquinolines are either commercially available or are prepared from commercially available materials. A great many substituted tetrahydroisoquinolines are known, including many fused isothiazole, piperidino and pyrrolidino derivatives. Thus, for example, compounds of formula IA where $R_1$ is 5-fluoro—can be prepared starting with 5-fluoro-1,2,3,4-tetrahydroisoquinoline. Similarly, as another among many examples, compounds of formula IA where $R_1$ or $R_2$ is 6-methyl—can be prepared starting with 6-methyl-1,2,3,4-tetrahydroisoquinoline. and, again, in two more examples among many, compounds of formula IA where $R_1$ and $R_2$ are 6- and 7-chloro, respectively, can be prepared starting with 6-, 7-dichloro-1,2,3,4-tetrahydroisoquinoline; and compounds with a substituent in the 9-position can be prepared starting with the appropriate 9-substituted tetrahydroisoquinoline. Analogously, compounds with R' other than H can be prepared starting with the appropriate 1-, 3-, or 4-substituted tetrahydroisoquinolines. For examples, compounds in which, in the 1- and 4-positions, R' is phenyl, methoxy, ethyl, methyl, F, or 2-(N—, N-dimethylamino)ethyl are accessible via the commercially available 1- and 4-substituted tetrahydroisoquinolines.

Scheme 1:

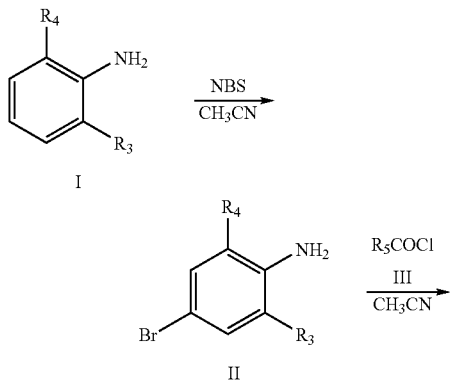

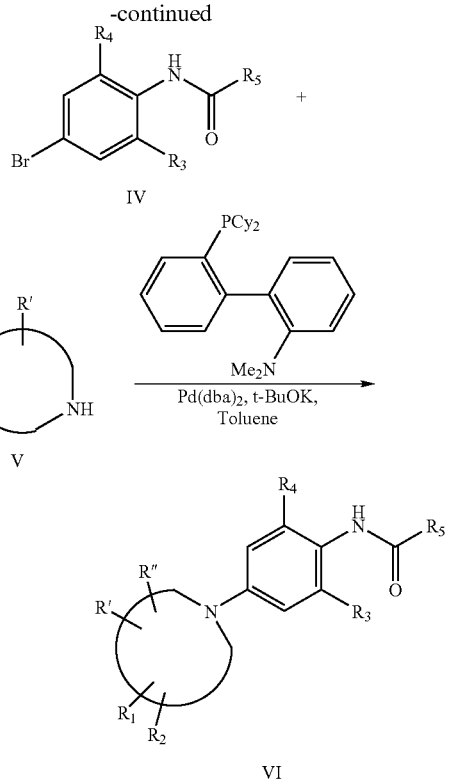

In this procedure the aromatic amine I is brominated according to standard procedures, including but not limited to the reaction with such reagents as N-bromosuccinimide in an aprotic solvent such as acetonitrile. The reaction mixture is typically heated under reflux for a period of from approximately 8 to approximately 48 hours.

In a typical procedure, the resulting bromo derivative II is purified by filtration of the crude reaction mixture through Celite. If desired, other standard purification techniques, including flash chromatography, can be used.

In the following step, the reaction of a compound II with the appropriate acyl chloride III in an aprotic solvent such as acetonitrile produces the amide of general formula IV. This reaction is typically conducted at room temperature for a period of from approximately 4 to approximately 48 hours. The resulting amide of general formula IV can be purified by a standard chromatographic technique such as flash chromatography or thin layer chromatography.

The next step of the reaction sequence is to prepare the desired product of general Formula VI using the well-known palladium coupling reaction, employing a phosphine ligand such as the commercially available dicyclohexyl phosphino-2'-(N,N,-dimethylamino)biphenyl. Thus, the amine of general formula V can be coupled to the bromine derivative of general formula IV using a palladium derivative such as, for example, bis(dibenzylidineacetone)palladium, a base such as potassium tert-butoxide and the ligand dicyclohexyl phosphino-2'-(N,N,-dimethyl amino)biphenyl in an aprotic solvent. The reaction mixture is typically heated in an oil bath at 90° C. for a period of from approximately 8 to approximately 48 hours, or it can be heated using a microwave apparatus (Horizon unit, Biotage) at a temperature range of from approximately 90° to approximately 250° C. The desired compound of general formula VI is purified by standard chromatographic techniques, such as flash chromatography or thin layer chromatography. It can also be recrystallized from toluene.

Section II. The preparation of compounds of formula IX is outlined in Scheme 2.

Section III. The preparation of compound of formula XII is outlined in Scheme 3.

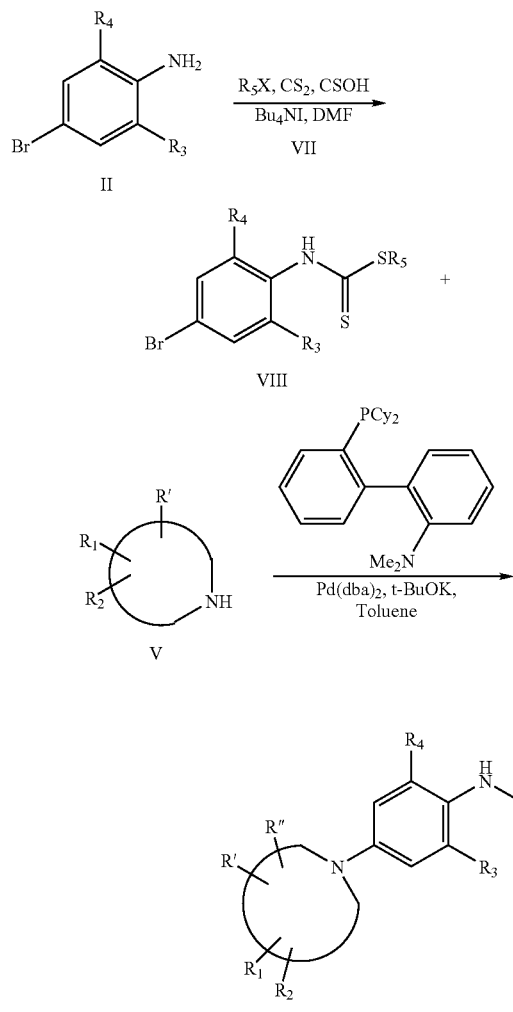

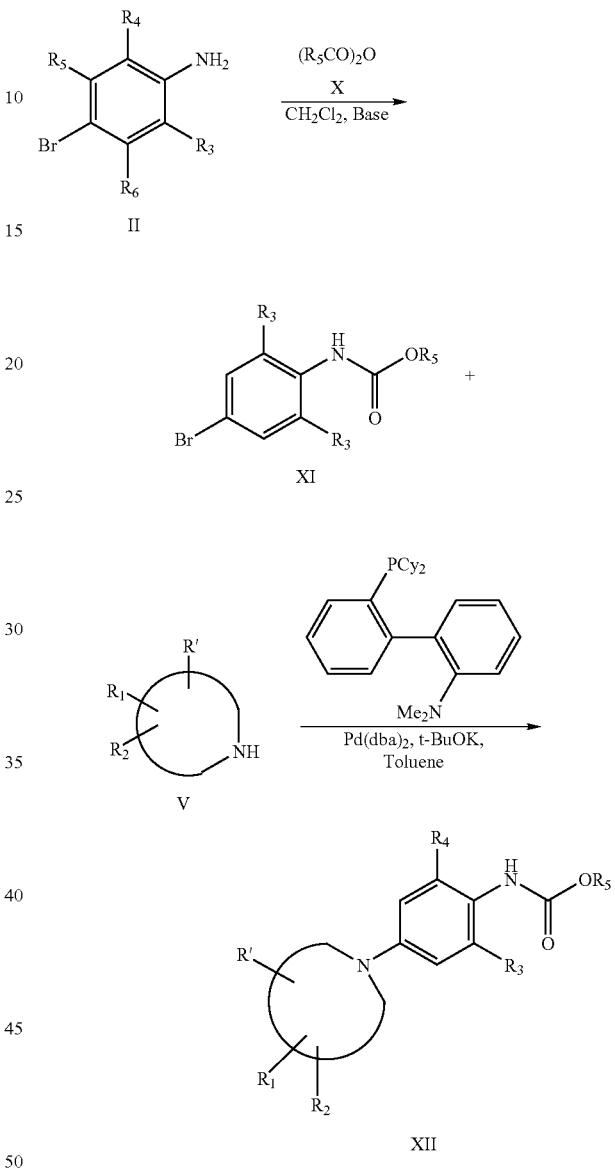

In reactions in section II, the compounds of general Formula IX are prepared in a way similar to that employed in section I. The aniline derivative II (section I) is combined with the haloalkyl compound VII under standard conditions to produce the desired thioester of general formula VIII. The reaction is typically conducted at a temperature of from approximately 20° to approximately 90° C. for a period of from approximately 8 to approximately 48 hours, or in a microwave apparatus (Horizon unit, Biotage) at a temperature range of from approximately 90° to approximately 250° C. As in the previous sequence, the thioester can be purified by standard chromatographic techniques such as flash chromatography or thin layer chromatography. The final step, a palladium coupling reaction to produce the compound of general Formula IX, is identical to that described in the corresponding step in Section I.

In section III, the carbamate derivative of general Formula XI is obtained from the aniline derivative of general Formula II (see section I) using standard conditions. Typically, the aniline is allowed to react with an anhydride derivative of general Formula X in the presence of a base such as triethylamine or diisopropyl ethylamine in an aprotic solvent such as methylene chloride. The reaction is conducted at a temperature in the range of from approximately −20° to approximately 40° C. for a period of from approximately 30 min to approximately 48 hours, depending on the particular substrates. The resulting carbamate derivative of general Formula XI can be purified by the usual chromatographic techniques, such as flash chromatography or thin layer chromatography. As in sections I and II, the final step is a palladium coupling.

Section IV. The preparation of compound of formula XIII is outlined in Scheme 4.

Scheme 4:

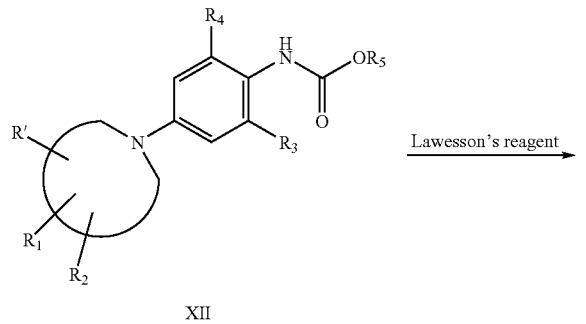

XII

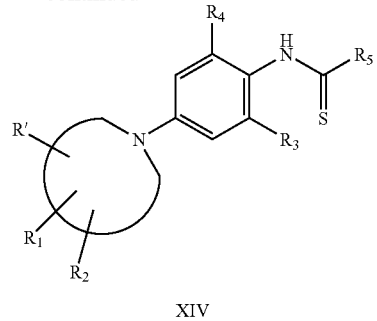

XIV

The compound of general Formula XIV is obtained under the same conditions described in section IV. The reaction is typically heated under reflux or stirred at room temperature for a period of from approximately 2 to approximately 48 hours. The resulting derivative of general Formula XIV can be purified by the usual chromatographic techniques, such as flash chromatography or thin layer chromatography.

Exemplary Compounds

Starting materials: bromodimethylaniline was obtained from either Alfa Aesar or Sigma Aldrich.

Substituted tetrahydroisoquinolines commercially available; those used in exemplary reactions here were obtained from ASW MedChem. Inc., of New Brunswick, N.J. Other substituted tetrahydroisoquinolines may be synthesized from commercially available starting materials via standard synthetic techniques.

Example 1

N-(2-chloro-4-(3,4-dihydroisoquinolin-2(1H)-yl)-6-(trifluoromethyl)phenyl)-3,3-dimethylbutanamide Step A: 4-bromo-2-chloro-6-(trifluoromethyl)aniline

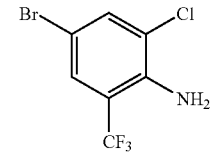

XIII

Here, a compound of general Formula XII, obtained as in section III, reacts with Lawesson's reagent in an aprotic solvent such as methylene chloride to produce the thiocarbamate. Depending on the substrates involved, the reaction is stirred at room temperature or is heated under reflux for a period of from approximately 2 to approximately 48 hours. The resulting compound XIII can be purified by the usual chromatographic techniques, such as flash chromatography or thin layer chromatography.

N-bromo succinimide (910 mg, 5.1 mmol) was added to a solution of 2-chloro-6-(trifluoromethyl)aniline (1.0 g, 5.1 mmol) and acetic acid (3 mL) in acetonitrile (10 mL) at room temperature. The mixture was heated at reflux, with stirring, for 18 h. The reaction mixture was then filtered through Celite and concentrated to give the title compound, which was used in the next step without further purification.

Section V. The preparation of compound of formula XIV is outlined in Scheme 5.

Step B: N-(4-bromo-2-chloro-6-(trifluoromethyl)phenyl)-3,3-dimethylbutanamide

Scheme 5:

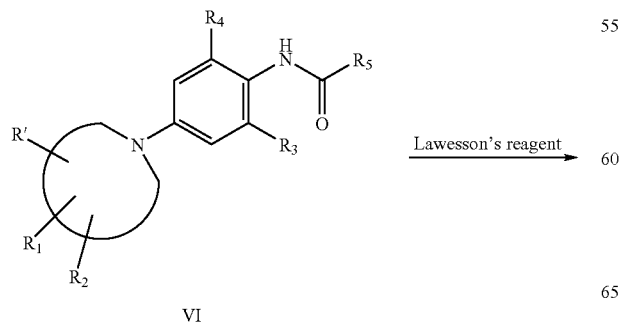

VI

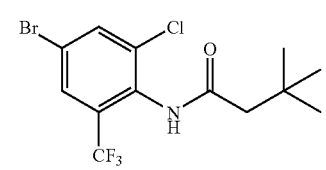

3,3-Dimethylbutanoyl chloride (1.08 g, 8.0 mmol) was added to a solution of 4-bromo-2-chloro-6-(trifluoromethyl) aniline (2.0 g, 7.3 mmol) in acetonitrile (10 mL). The reaction mixture was stirred at room temperature overnight. Water was added, and the mixture was then extracted with ethyl acetate. The organic layer was dried over sodium sulfate and concentrated. Purification by column chromatography in dichloromethane afforded the title compound as a powder (1.22 g, 65% over the two steps).

Step C: N-(2-chloro-4-(3,4-dihydroisoquinolin-2 (1H)-yl)-6-(trifluoromethyl)phenyl)-3,3-dimethylbutanamide

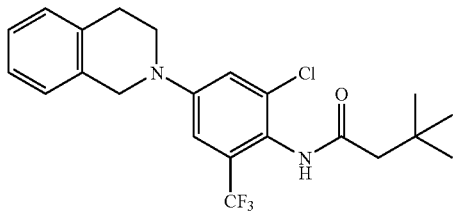

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon), and the solution was stirred for 15 minutes under argon. Potassium tert-butoxide (122 mg, 1.08 mmol), 1,2,3,4-tetrahydroisoquinoline (87 mg, 0.65 mmol), and N-(2-chloro-4-(3,4-dihydroisoquinolin-2(1H)-yl)-6-(trifluoromethyl)phenyl)-3,3-dimethylbutanamide (200 mg, 0.54 mmol) were then added, and the reaction mixture was stirred at 90° C. overnight. The reaction mixture was then cooled to room temperature, concentrated, and purified by thin layer chromatography (dichloromethane:methanol 5%) to afford the title compound as a solid. (106 mg, 47%).

$^1$H NMR (DMSO-d$_6$, 300 MHz) δ 1.02 (s, 9H), 2.07 (s, 3H), 2.17 (s, 2H), 2.92 (t, J=5.4 Hz, 2H), 3.62 (t, J=6 Hz, 2H), 4.48 (s, 2H), 7.33 (m, 6H), 9.30 (s, 1H).

Example 2

N-(4-(3,4-dihydroisoquinolin-2(1H)-yl)-2,6-dimethylphenyl)-3,3-dimethyl butanamide Step A: N-(4-Bromo-2,6-dimethyl-phenyl)-3,3-dimethyl-butanamide

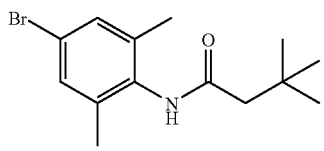

3,3-Dimethylbutanoyl chloride (3.37 g, 3.5 mL, 25 mmol) and triethylamine (2.53 g, 3.5 mL, 25 mmol) were added to a solution of 4-bromo-2,6-dimethyl-phenylamine (5.0 g, 25 mmol) in acetonitrile (30 mL). The reaction mixture was stirred at room temperature for 4 hours. Water was added to the mixture, and the precipitate which formed was collected to give the title compound as a powder (7.46 g, 100% yield).

Step B: N-(4-(3,4-dihydroisoquinolin-2(1H)-yl)-2,6-dimethylphenyl)-3,3-dimethylbutanamide

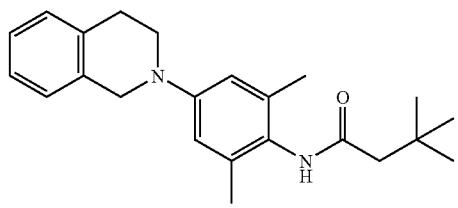

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (150 mg, 1.34 mmol), 1,2,3,4-tetrahydroisoquinoline (107 mg, 0.8 mmol) and N-(4-bromo-2,6-dimethyl-phenyl)-3,3-dimethyl-butanamide (200 mg, 0.67 mmol) were then added, and the reaction mixture was stirred at 90° C. overnight. The reaction mixture was then cooled to room temperature, concentrated, and purified by thin layer chromatography (dichloromethane:methanol 5%) to afford the title compound as a solid. (113.20 mg, 50%).

$^1$H NMR (DMSO-d$_6$, 300 MHz) δ 1.03 (s, 9H), 2.08 (s, 6H), 2.15 (s, 2H), 2.89 (t, J=5.7 Hz, 2H), 3.49 (t, J=5.7 Hz, 2H), 4.31 (s, 2H), 6.68 (s, 2H), 7.2 (m, 4H), 8.86 (s, 1H).

Example 3

N-(2-chloro-4-(3,4-dihydroisoquinolin-2(1H)-yl)-6-(trifluoromethyl)phenyl)-3-cyclopentyl propanamide Step A: 4-bromo-2-chloro-6-(trifluoromethyl)aniline

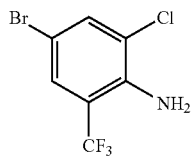

N-bromosuccinimide (910 mg, 5.1 mmol) was added to a solution of 2-chloro-6-(trifluoromethyl)aniline (1.0 g, 5.1 mmol) and acetic acid (3 mL) in acetonitrile (10 mL) at room temperature. The mixture was stirred at reflux for 18 h. The reaction mixture was then filtered through Celite and concentrated to give the title compound, which was used in the next step without further purification.

Step B: N-(4-Bromo-2-chloro-6-trifluoromethyl-phenyl)-3-cyclopentyl-propionamide

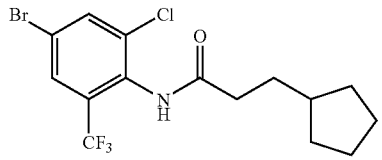

3-Cyclopentyl propionyl chloride (1.28 g, 8.0 mmol) was added to a solution of 4-bromo-2-chloro-6-(trifluoromethyl) aniline (2.0 g, 7.3 mmol) in acetonitrile (10 mL). The reaction mixture was stirred at room temperature overnight. Water was added, and the mixture was then extracted with ethyl acetate. The organic layer was dried over sodium sulfate and concentrated. Purification by column chromatography (100% DCM) afforded the title compound as a powder.

Step C: N-(2-chloro-4-(3,4-dihydroisoquinolin-2 (1H)-yl)-6-(trifluoromethyl)phenyl)-3-cyclopentyl propanamide

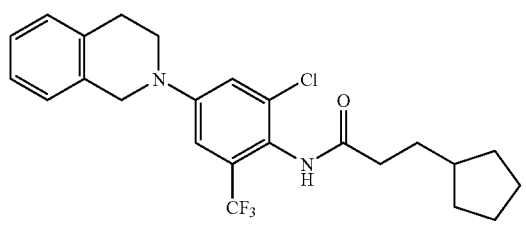

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (150 mg, 1.34 mmol), 1,2,3, 4-tetrahydroisoquinoline (107 mg, 0.8 mmol), and N-(4-bromo-2-chloro-6-trifluoromethyl phenyl)-3-cyclopentyl propionamide (200 mg, 0.5 mmol) were then added, and the reaction mixture was stirred at 90° C. overnight. The reaction mixture was then cooled to room temperature, concentrated, and purified by thin layer chromatography (dichloromethane:methanol 5%) to afford the title compound as a solid.

Yield: 28%. $^1$H NMR (CDCl$_3$, 300 MHz) δ 1.15 (m, 2H), 1.65 (m, 4H), 1.85 (m, 4H), 2.44 (t, J=7.5 Hz, 2H), 3.01 (t, J=5.7. Hz, 2H), 3.6 (t, J=5.7. Hz, 2H), 4.43 (s, 2H), 6.72 (s, 1H), 7.10 (m, 2H), 7.24 (m, 4H).

Example 4

N-(2-chloro-4-(6-fluoro-3,4-dihydroisoquinolin-2 (1H)-yl)-6-(trifluoromethyl)phenyl)-3,3-dimethylbutanamide Step A: 6-fluoro-3,4-dihydroisoquinolin-1(2H)-one

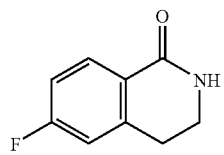

Sodium azide (0.870 g, 13.33 mmol) was added in portions to a stirred solution of 5-fluoro-1-indanone (1.0 g, 6.67 mmol) and methanesulfonic acid (4 mL) in dichloromethane (4 mL) at 0° C. The reaction mixture was stirred at room temperature for 18 h. The mixture was then cooled to 0° C. and neutralized with 2N NaOH. The layers were separated, the aqueous layer extracted with dichloromethane, and the combined organic layers were dried over Na$_2$SO$_4$ and concentrated to give the title compound as a white powder. The crude product was used in the next step.

Step B: 6-fluoro-1,2,3,4-tetrahydroisoquinoline

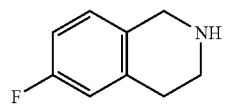

Diborane (1M, THF, 24 mL) was added at 0° C. to a solution of 6-fluoro-3,4-dihydro isoquinolin-1(2H)-one (1.14 g, 6.9 mmol) in THF (8 mL). The mixture was stirred at reflux for 18 h. It was cooled to room temperature and water was added. The mixture was extracted with dichloromethane, and the organic layer was dried over sodium sulfate and concentrated. Purification by column chromatography (hexanes: ethyl acetate 1:1) afforded the title compound.

Step C: N-(2-chloro-4-(6-fluoro-3,4-dihydroisoquinolin-2(1H)-yl)-6-(trifluoromethyl)phenyl)-3,3-dimethylbutanamide

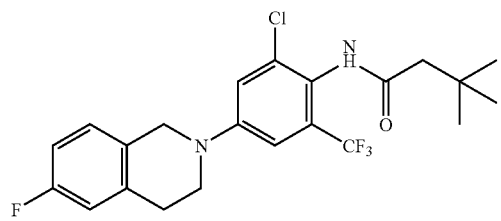

Bis(dibenzylidineacetone)palladium (2 mg, 0.0035 mmol) and (2'-dicyclohexyl phosphanyl biphenyl-2-yl)dimethylamine (3.3 mg, 0.0084 mmol) were added to dry toluene (10 mL purged with argon) and stirred for 15 minutes under argon. Potassium tert-butoxide (122 mg, 1.08 mmol), 6-fluoro-1,2,3,4-tetrahydroisoquinoline (96 mg, 0.65 mmol), and N-(4-bromo-2-chloro-6-(trifluoromethyl)phenyl)-3,3-dimethylbutanamide (200 mg, 0.54 mmol) were then added, and the reaction mixture was stirred at 90° C. overnight. The reaction mixture was then cooled to room temperature, concentrated, and purified by thin layer chromatography (dichloromethane:methanol 5%) to afford the title compound as a solid. m/z=441 [M−1]$^-$.

Example 5

N-[2-Chloro-4-(3,4-dihydro-1H-isoquinolin-2-yl)-6-methyl-phenyl]-3,3-dimethyl-butanamide Step A:
N-(4-Bromo-2-chloro-6-methylphenyl)-3,3-dimethyl butanamide

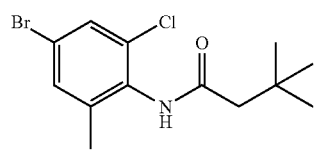

3,3-Dimethylbutanoyl chloride (3.37 g, 3.5 mL, 25 mmol) and triethylamine (2.53 g, 3.5 mL, 25 mmol) were added to a solution of 4-bromo-2-chloro-6-methyl-phenylamine (5.0 g, 25 mmol) in acetonitrile (30 mL). The reaction mixture was stirred at room temperature for 4 hours. Water was added to the mixture, and the precipitate that formed was collected to give the title compound as a powder (7.46 g, 100% yield).

Step B: N-[2-Chloro-4-(3,4-dihydro-1H-isoquinolin-2-yl)-6-methyl-phenyl]-3,3-dimethyl-butanamide The synthesis of this compound was performed as described in example 4, step C.

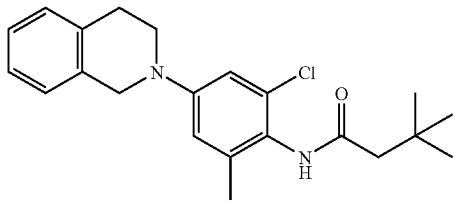

$^1$H NMR (DMSO-d$_6$, 300 MHz) δ 1.03 (s, 9H), 2.12 (s, 3H), 2.15 (s, 2H), 2.89 (t, J=5.7 Hz, 2H), 3.53 (t, J=5.7 Hz, 2H), 4.36 (s, 2H), 6.87 (d, J=9.6, 2H), 7.2 (m, 4H), 9.08 (s, 1H).

Example 6

N-[2-Chloro-4-(6-fluoro-3,4-dihydro-1H-isoquinolin-2-yl)-6-trifluoromethyl-phenyl]-3-cyclopentyl-propionamide Step A: 4-bromo-2-chloro-6-(trifluoromethyl)aniline

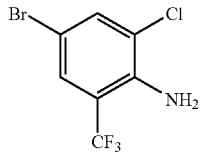

N-bromosuccinimide (910 mg, 5.1 mmol) was added at room temperature to a solution of 2-chloro-6-(trifluoromethyl)aniline (1.0 g, 5.1 mmol) and acetic acid (3 mL) in acetonitrile (10 mL). The mixture was stirred at reflux to 18 h. The reaction mixture was then filtered through celite and concentrated to give the title compound, which was used in the next step without further purification.

Step B: N-(4-Bromo-2-chloro-6-trifluoromethyl-phenyl)-3-cyclopentyl propionamide

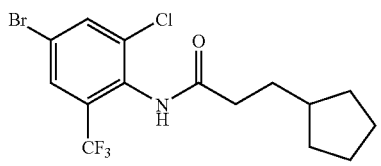

3-Cyclopentyl propionyl chloride (1.28 g, 8.0 mmol) was added to a solution of 4-bromo-2-chloro-6-(trifluoromethyl) aniline (2.0 g, 7.3 mmol) in acetonitrile (10 mL). The reaction mixture was stirred at room temperature overnight. Water was added to the mixture, which was then extracted with ethyl acetate. The organic layer was dried over sodium sulfate and concentrated. Purification by column chromatography (100% DCM) afforded the title compound as a powder.

Step C: N-[2-Chloro-4-(6-fluoro-3,4-dihydro-1H-isoquinolin-2-yl)-6-trifluoromethyl-phenyl]-3-cyclopentyl propionamide

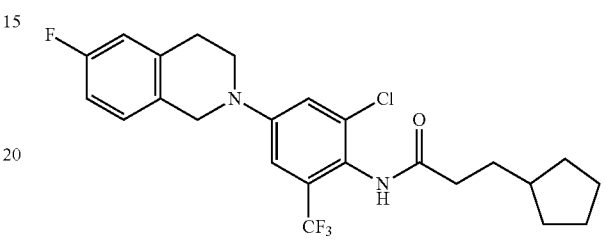

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (140 mg, 1.25 mmol), 6-fluoro-1,2,3,4-tetrahydroisoquinoline hydrochloride salt (150 mg, 0.8 mmol) and N-(4-Bromo-2-chloro-6-trifluoromethyl-phenyl)-3-cyclopentyl-propionamide (200 mg, 0.5 mmol) were then added and the reaction mixture was stirred at 90° C. overnight. The reaction mixture was then cooled to room temperature, concentrated, and purified by thin layer chromatography (dichloromethane:methanol 5%) to afford the title compound as a solid.

$^1$H NMR (DMSO-d$_6$, 300 MHz) δ 1.07 (m, 2H), 1.57 (m, 6H), 1.75 (m, 3H), 2.31 (m, 2H), 2.93 (t, J=5.1 Hz, 2H), 3.60 (t, J=5.4 Hz, 2H), 4.45 (s, 2H), 7.06 (m, 2H), 7.15 (s, 1H), 7.32 (m, 2H), 9.39 (s, 1H).

Example 7

N-[2,6-Dimethyl-4-(6-trifluoromethyl-3,4-dihydro-1H-isoquinolin-2-yl)-phenyl]-3,3-dimethyl butanamide Step A: N-(4-Bromo-2,6-dimethyl-phenyl)-3,3-dimethyl-butanamide

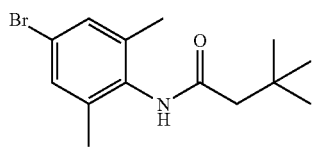

3,3-Dimethylbutanoyl chloride (3.37 g, 3.5 mL, 25 mmol) and triethylamine (2.53 g, 3.5 mL, 25 mmol) were added to a solution of 4-Bromo-2,6-dimethyl-phenylamine (5.0 g, 25 mmol) in acetonitrile (30 mL). The reaction mixture was stirred at room temperature for 4 hours. Water was added to the mixture, and the precipitate which formed was collected to give the title compound as a powder (7.46 g, 100% yield).

Step B: N-[2,6-Dimethyl-4-(6-trifluoromethyl-3,4-dihydro-1H-isoquinolin-2-yl)-phenyl]-3,3-dimethyl butanamide

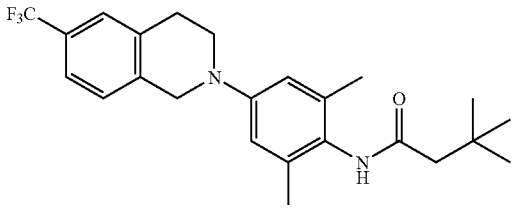

Bis(dibenzylidineacetone)palladium (390 mg, 0.68 mmol) and (2'-dicyclohexyl phosphanyl-biphenyl-2-yl)-dimethylamine (800 mg, 2.0 mmol) were added to dry toluene (150 mL purged with argon) and stirred for 30 minutes under argon. Potassium tert-butoxide (4.75 mg, 42.3 mmol), 6-Trifluoromethyl-1,2,3,4-tetrahydro-isoquinoline hydrochloride salt (4.82 g, 20.3 mmol) and N-(4-bromo-2,6-dimethyl-phenyl)-3,3-dimethyl-butanamide (5 g, 16.8 mmol) were then added, and the reaction mixture was stirred at 80° C. overnight. The reaction mixture was then cooled to room temperature and recrystallized from toluene to afford the title compound as a solid. (5.55 g, 79%).

$^1$H NMR (DMSO-$d_6$, 500 MHz) δ 1.03 (s, 9H), 2.09 (s, 6H), 2.15 (s, 2H), 2.98 (t, J=5.0 Hz, 2H), 3.52 (t, J=6.0 Hz, 2H), 4.40 (s, 2H), 6.71 (s, 2H), 7.45 (d, J=8.0, 1H), 7.52 (m, 2H), 8.87 (s, 1H).

Example 8

N-[2-Chloro-6-trifluoromethyl-4-(6-trifluoromethyl-3,4-dihydro-1H-isoquinolin-2-yl)-phenyl]-3,3-dimethyl butanamide Step A: 4-bromo-2-chloro-6-(trifluoromethyl)aniline

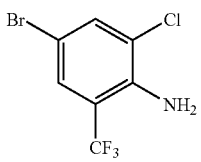

N-bromosuccinimide (910 mg, 5.1 mmol) was added to a solution of 2-chloro-6-(trifluoromethyl)aniline (1.0 g, 5.1 mmol) in acetonitrile (10 mL) and acetic acid (3 mL) at room temperature. The mixture was stirred at reflux to 18 h. The reaction mixture was then filtered through celite and concentrated to give the title compound which was used in the next step without further purification.

Step B: N-(4-bromo-2-chloro-6-(trifluoromethyl) phenyl)-3,3-dimethylbutanamide

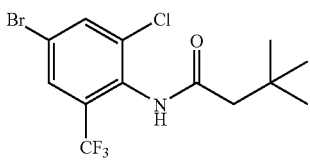

3,3-dimethylbutanoyl chloride (1.08 g, 8.0 mmol) was added to a solution of 4-bromo-2-chloro-6-(trifluoromethyl) aniline (2.0 g, 7.3 mmol) in acetonitrile (10 mL). The reaction mixture was stirred at room temperature overnight. Water was added to the mixture and then extracted with ethyl acetate. The organic layer was dried over sodium sulfate and concentrated. Purification by column chromatography (100% DCM) afforded the title compound as a powder (1.22 g, 65%) over the two steps.

Step C: N-[2-Chloro-6-trifluoromethyl-4-(6-trifluoromethyl-3,4-dihydro-1H-isoquinolin-2-yl)-phenyl]-3,3-dimethyl butanamide

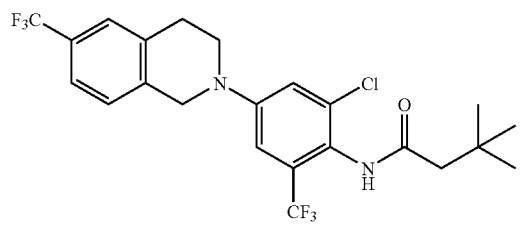

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 6-trifluoro-1,2,3,4-tetrahydroisoquinoline (154 mg, 0.65 mmol) and N-(4-bromo-2-chloro-6-(trifluoromethyl)phenyl)-3,3-dimethylbutanamide (200 mg, 0.54 mmol) were then added, and the reaction mixture was stirred at 90° C. overnight. The reaction mixture was then cooled to room temperature, concentrated, and purified by thin layer chromatography (dichloromethane:methanol 5%) to afford the title compound as a solid $^1$H NMR (DMSO-$d_6$, 500 MHz) δ 1.03 (s, 9H), 2.17 (s, 2H), 3.02 (t, J=5.35 Hz, 2H), 3.65 (t, J=5.0 Hz, 2H), 4.61 (s, 2H), 7.19 (d, J=2.0 Hz, 1H), 7.38 (d, J=1.9 Hz, 1H), 7.49 (d, J=8.0 Hz, 1H), 7.56 (d, J=8.1 Hz, 1H), 7.59 (s, 1H), 9.32 (s, 1H).

Example 9

N-[2-Chloro-4-(6-chloro-3,4-dihydro-1H-isoquinolin-2-yl)-6-trifluoromethyl-phenyl]-3,3-dimethyl butanamide Step A: 4-bromo-2-chloro-6-(trifluoromethyl)aniline

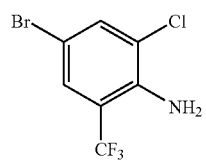

N-bromosuccinimide (910 mg, 5.1 mmol) was added to a solution of 2-chloro-6-(trifluoromethyl)aniline (1.0 g, 5.1 mmol) in acetonitrile (10 mL) and acetic acid (3 mL) at room temperature. The mixture was stirred at reflux to 18 h. The reaction mixture was then filtered through Celite and concentrated to give the title compound which was used in the next step without further purification.

Step B: N-(4-bromo-2-chloro-6-(trifluoromethyl) phenyl)-3,3-dimethylbutanamide

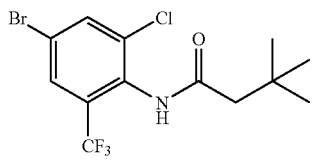

3,3-Dimethylbutanoyl chloride (1.08 g, 8.0 mmol) was added to a solution of 4-bromo-2-chloro-6-(trifluoromethyl) aniline (2.0 g, 7.3 mmol) in acetonitrile (10 mL). The reaction mixture was stirred at room temperature overnight. Water was added to the mixture and then extracted with ethyl acetate. The organic layer was dried over sodium sulfate and concentrated. Purification by column chromatography (100% DCM) afforded the title compound as a powder (1.22 g, 65%) over the two steps.

Step C: N-[2-Chloro-4-(6-chloro-3,4-dihydro-1H-isoquinolin-2-yl)-6-trifluoromethyl-phenyl]-3,3-dimethyl-butanamide

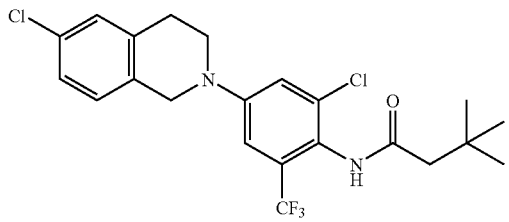

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (151 mg, 1.35 mmol), 6-chloro-1,2,3,4-tetrahydroisoquinoline hydrochloride (133 mg, 0.65 mmol) and N-(4-bromo-2-chloro-6-(trifluoromethyl)phenyl)-3,3-dimethylbutanamide (200 mg, 0.54 mmol) were then added and the reaction mixture was stirred at 90° C. overnight. The reaction mixture was then cooled to room temperature, concentrated and purified by thin layer chromatography (dichloromethane:methanol 5%) to afford the title compound as a solid $^1$H NMR (DMSO-$d_6$, 500 MHz) δ 1.02 (s, 9H), 2.17 (s, 2H), 2.92 (t, J=5.35 Hz, 2H), 3.61 (t, J=5.6 Hz, 2H), 4.47 (s, 2H), 7.16 (s, 1H), 7.29 (m, 3H), 7.34 (s, 1H), 9.31 (s, 1H).

Example 10

N-[4-(6-Chloro-3,4-dihydro-1H-isoquinolin-2-yl)-2,6-dimethyl-phenyl]-3,3-dimethyl-butanamide Step A: N-(4-Bromo-2,6-dimethyl-phenyl)-3,3-dimethyl-butanamide

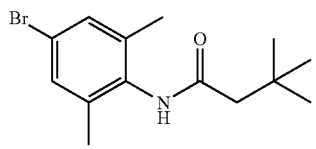

3,3-Dimethylbutanoyl chloride (3.37 g, 3.5 mL, 25 mmol) and triethylamine (2.53 g, 3.5 mL, 25 mmol) were added to a solution of 4-bromo-2,6-dimethyl phenylamine (5.0 g, 25 mmol) in acetonitrile (30 mL). The reaction mixture was stirred at room temperature for 4 hours. Water was added to the mixture and the precipitate formed collected to give the title compound as a powder (7.46 g, 100% yield).

Step B: N-[4-(6-Chloro-3,4-dihydro-1H-isoquinolin-2-yl)-2,6-dimethyl-phenyl]-3,3-dimethyl butanamide

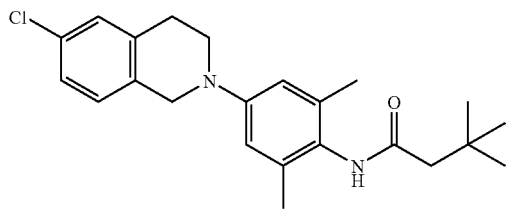

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (5 mL purged with argon) and stirred for 15 minutes under argon. Potassium tert-butoxide (188 mg, 1.7 mmol), 6-chloro-1,2,3,4-tetrahydro isoquinoline hydrochloride salt (165 mg, 0.8 mmol), and N-(4-bromo-2,6-dimethylphenyl)-3,3-dimethylbutanamide (200 mg, 0.67 mmol) were then added, and the reaction mixture was stirred at 80° C. overnight. The reaction mixture was then cooled to room temperature and filtered through silica gel. Purification by preparative thin layer chromatography afforded the title compound as a solid.

$^1$H NMR (DMSO-$d_6$, 500 MHz) δ 1.03 (s, 9H), 2.08 (s, 6H), 2.15 (s, 2H), 2.89 (t, J=5.25 Hz, 2H), 3.47 (t, J=5.6 Hz, 2H), 4.30 (s, 2H), 6.68 (s, 2H), 7.25 (m, 3H), 8.85 (s, 1H).

Example 11

N-[4-(6-fluoro-3,4-dihydro-1H-isoquinolin-2-yl)-2,6-dimethyl phenyl]-3,3-dimethyl butanamide Step A: N-(4-Bromo-2,6-dimethyl-phenyl)-3,3-dimethyl-butanamide

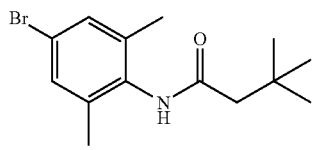

3,3-Dimethylbutanoyl chloride (3.37 g, 3.5 mL, 25 mmol) and triethylamine (2.53 g, 3.5 mL, 25 mmol) were added to a solution of 4-bromo-2,6-dimethyl-phenylamine (5.0 g, 25 mmol) in acetonitrile (30 mL). The reaction mixture was stirred at room temperature for 4 hours. Water was added to the mixture, and the precipitate which formed was collected to give the title compound as a powder (7.46 g, 100% yield).

Step B: N-[4-(6-Fluoro-3,4-dihydro-1H-isoquinolin-2-yl)-2,6-dimethylphenyl]-3,3-dimethyl butanamide

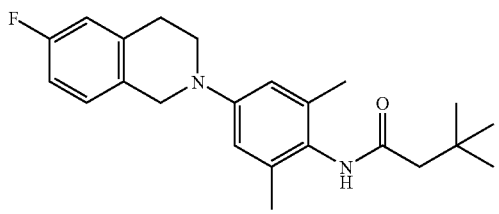

Bis(dibenzylidineacetone)palladium (390 mg, 0.68 mmol) and (2'-dicyclohexyl phosphanyl-biphenyl-2-yl)-dimethylamine (800 mg, 2.0 mmol) were added to dry toluene (150 mL purged with argon for 30 minutes) and stirred for 30 minutes under argon. Potassium tert-butoxide (4.75 mg, 42.3 mmol), 6-fluoro-1,2,3,4-tetrahydro-isoquinoline hydrochloride salt (3.2 g, 17.0 mmol), and N-(4-bromo-2,6-dimethyl-phenyl)-3,3-dimethyl-butanamide (5 g, 16.8 mmol) were then added, and the reaction mixture was stirred at 80° C. overnight. The reaction mixture was then cooled to room temperature and recrystallized from toluene to afford the title compound as a solid. (5.11 g, 83%).

$^1$H NMR (DMSO-$d_6$, 500 MHz) δ 1.03 (s, 9H), 2.08 (s, 6H), 2.15 (s, 2H), 2.89 (t, J=5.25 Hz, 2H), 3.47 (t, J=5.6 Hz, 2H), 4.30 (s, 2H), 6.68 (s, 2H), 6.99 (m, 2H), 7.25 (m, 1H), 8.84 (s, 1H).

Example 12

N-[2-Chloro-4-(7-fluoro-3,4-dihydro-1H-isoquinolin-2-yl)-6-trifluoromethyl-phenyl]-3,3-dimethylbutanamide Step A: 4-bromo-2-chloro-6-(trifluoromethyl)aniline

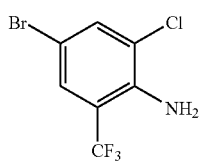

N-bromosuccinimide (910 mg, 5.1 mmol) was added to a solution of 2-chloro-6-(trifluoromethyl)aniline (1.0 g, 5.1 mmol) in acetonitrile (10 mL) and acetic acid (3 mL) at room temperature. The mixture was stirred at reflux for 18 h. The reaction mixture was then filtered through Celite and concentrated to give the title compound, which was used in the next step without further purification.

Step B: N-(4-bromo-2-chloro-6-(trifluoromethyl)phenyl)-3,3-dimethylbutanamide

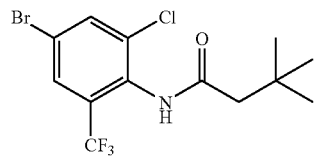

3,3-Dimethylbutanoyl chloride (1.08 g, 8.0 mmol) was added to a solution of 4-bromo-2-chloro-6-(trifluoromethyl)aniline (2.0 g, 7.3 mmol) in acetonitrile (10 mL). The reaction mixture was stirred at room temperature overnight. Water was added to the mixture and then extracted with ethyl acetate. The organic layer was dried over sodium sulfate and concentrated. Purification by column chromatography (100% DCM) afforded the title compound as a powder (1.22 g, 65%) over the two steps.

Step C: N-[2-Chloro-4-(7-fluoro-3,4-dihydro-1H-isoquinolin-2-yl)-6-trifluoromethyl-phenyl]-3,3-dimethylbutanamide

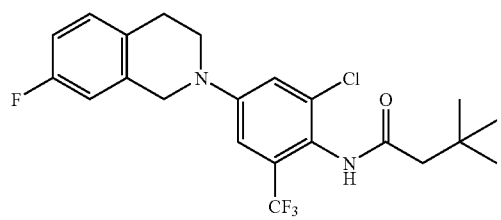

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (151 mg, 1.35 mmol), 7-fluoro-1,2,3,4-tetrahydroisoquinoline hydrochloride (122 mg, 0.65 mmol) and N-(4-bromo-2-chloro-6-(trifluoromethyl)phenyl)-3,3-dimethylbutanamide (200 mg, 0.54 mmol) were then added, and the reaction mixture was stirred at 90° C. overnight. The reaction mixture was then cooled to room temperature, concentrated, and purified by thin layer chromatography (dichloromethane:methanol 5%) to afford the title compound as a solid.

$^1$H NMR (DMSO-$d_6$, 500 MHz) δ 1.02 (s, 9H), 2.17 (s, 2H), 2.89 (t, J=5.1 Hz, 2H), 3.61 (t, J=5.7 Hz, 2H), 4.49 (s, 2H), 7.03 (dd, J=8.6, 2.3 Hz, 1H), 7.12 (m, 2H), 7.16 (d, J=2.2 Hz, 1H), 7.23 (m, 1H), 7.33 (d, J=2.6, 1H), 9.30 (s, 1H).

Example 13

N-[4-(7-Fluoro-3,4-dihydro-1H-isoquinolin-2-yl)-2,6-dimethyl-phenyl]-3,3-dimethyl-butanamide Step A: N-(4-Bromo-2,6-dimethyl-phenyl)-3,3-dimethyl-butanamide

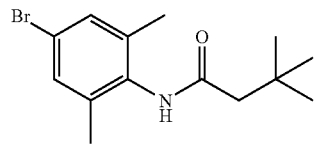

3,3-Dimethylbutanoyl chloride (3.37 g, 3.5 mL, 25 mmol) and triethylamine (2.53 g, 3.5 mL, 25 mmol) were added to a solution of 4-Bromo-2,6-dimethyl-phenylamine (5.0 g, 25 mmol) in acetonitrile (30 mL). The reaction mixture was stirred at room temperature for 4 hours. Water was added to the mixture and the precipitate formed collected to give the title compound as a powder (7.46 g, 100% yield).

Step B: N-[4-(7-Fluoro-3,4-dihydro-1H-isoquinolin-2-yl)-2,6-dimethyl-phenyl]-1-3,3-dimethyl-butanamide

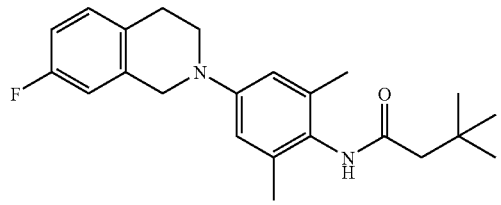

Bis(dibenzylidineacetone)palladium (156 mg, 0.28 mmol) and (2'-dicyclohexyl phosphanyl-biphenyl-2-yl)-dimethylamine (320 mg, 0.8 mmol) were added to dry toluene (60 mL purged with argon) and stirred for 15 minutes under argon. Potassium tert-butoxide (1.9 g, 16.25 mmol), 7-fluoro-1,2,3,4-tetrahydro-isoquinoline hydrochloride salt (1.28 g, 6.8 mmol), and N-(4-bromo-2,6-dimethyl-phenyl)-3,3-dimethyl-butanamide (5 g, 6.8 mmol) were then added, and the reaction mixture was stirred at 80° C. overnight. The reaction mixture was then cooled to room temperature and recrystallized from toluene to afford the title compound as a solid. (1.9 g, 76%).

$^1$H NMR (DMSO-d$_6$, 400 MHz) δ 1.05 (s, 9H), 2.10 (s, 6H), 2.17 (s, 2H), 2.89 (t, J=5.1 Hz, 2H), 3.49 (t, J=5.7 Hz, 2H), 4.34 (s, 2H), 6.70 (s, 2H), 7.0 (m, 1H), 7.1 (m, 1H), 7.2 (m, 1H), 8.9 (s, 1H).

Example 14

N-[2-Chloro-4-(6-fluoro-3,4-dihydro-1H-isoquinolin-2-yl)-6-methylphenyl]-3,3-dimethylbutanamide Step A: N-(4-Bromo-2-chloro-6-methyl-phenyl)-3,3-dimethyl-butanamide

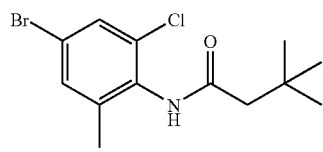

3,3-Dimethylbutanoyl chloride (3.37 g, 3.5 mL, 25 mmol) and triethylamine (2.53 g, 3.5 mL, 25 mmol) were added to a solution of 4-Bromo-2-chloro-6-methyl-phenylamine (5.0 g, 25 mmol) in acetonitrile (30 mL). The reaction mixture was stirred at room temperature for 4 hours. Water was added to the mixture and the precipitate formed collected to give the title compound as a powder (7.46 g, 100% yield).

Step B: N-[2-Chloro-4-(6-fluoro-3,4-dihydro-1H-isoquinolin-2-yl)-6-methylphenyl]-3,3-dimethylbutanamide

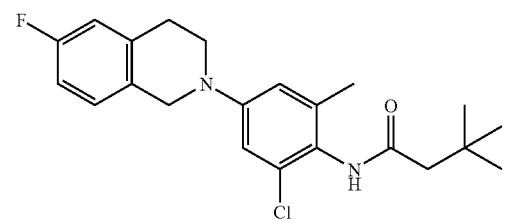

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 6-fluoro-1,2,3,4-tetrahydroisoquinoline hydrochloride salt (121 mg, 0.65 mmol) and N-(4-bromo-2-chloro-6-methylphenyl)-3,3-dimethylbutanamide (200 mg, 0.63 mmol) were then added and the reaction mixture was stirred at 90° C. overnight. The reaction mixture was then cooled to room temperature, concentrated and purified by thin layer chromatography (dichloromethane:methanol 5%) to afford the title compound as a solid.

$^1$H NMR (DMSO-d$_6$, 400 MHz) δ 1.05 (s, 9H), 2.14 (s, 3H), 2.17 (s, 2H), 2.91 (t, J=5.25 Hz, 2H), 3.52 (t, J=5.6 Hz, 2H), 4.37 (s, 2H), 6.85 (s, 1H), 6.9 (s, 1H), 7.0 (m, 2H), 7.3 (m, 1H), 9.10 (s, 1H).

Example 15

N-[2-Chloro-4-(7-fluoro-3,4-dihydro-1H-isoquinolin-2-yl)-6-methylphenyl]-3,3-dimethylbutanamide Step A: N-(4-Bromo-2-chloro-6-methyl-phenyl)-3,3-dimethyl-butanamide

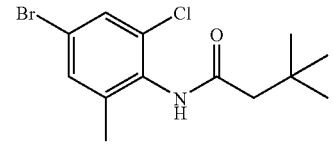

3,3-Dimethylbutanoyl chloride (3.37 g, 3.5 mL, 25 mmol) and triethylamine (2.53 g, 3.5 mL, 25 mmol) were added to a solution of 4-Bromo-2-chloro-6-methyl-phenylamine (5.0 g, 25 mmol) in acetonitrile (30 mL). The reaction mixture was stirred at room temperature for 4 hours. Water was added to the mixture and the precipitate formed collected to give the title compound as a powder (7.46 g, 100% yield).

Step B: N-[2-Chloro-4-(7-fluoro-3,4-dihydro-1H-isoquinolin-2-yl)-6-methylphenyl]-3,3-dimethylbutanamide

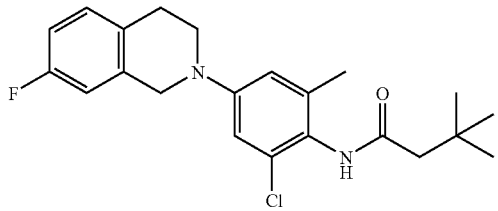

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 7-fluoro-1,2,3,4-tetrahydroisoquinoline hydrochloride salt (121 mg, 0.65 mmol) and N-(4-bromo-2-chloro-6-methylphenyl)-3,3-dimethylbutanamide (200 mg, 0.63 mmol) were then added and the reaction mixture was stirred at 90° C. overnight. The reaction mixture was then cooled to room temperature, concentrated, and purified by thin layer chromatography (dichloromethane:methanol 5%) to afford the title compound as a solid.

$^1$H NMR (DMSO-$d_6$, 400 MHz) δ 1.04 (s, 9H), 2.14 (s, 3H), 2.18 (s, 2H), 2.88 (t, J=5.25 Hz, 2H), 3.55 (t, J=5.6 Hz, 2H), 4.4 (s, 2H), 6.88 (s, 1H), 6.9 (s, 1H), 7.0 (m, 1H), 7.1 (m, 1H), 7.2 (m, 1H), 9.10 (s, 1H).

Example 16

N-[2-Chloro-6-methyl-4-(6-trifluoromethyl-3,4-dihydro-1H-isoquinolin-2-yl)-phenyl]-3,3-dimethylbutanamide Step A: N-(4-Bromo-2-chloro-6-methyl-phenyl)-3,3-dimethyl-butanamide

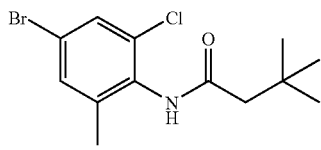

3,3-Dimethylbutanoyl chloride (3.37 g, 3.5 mL, 25 mmol) and triethylamine (2.53 g, 3.5 mL, 25 mmol) were added to a solution of 4-Bromo-2-chloro-6-methyl-phenylamine (5.0 g, 25 mmol) in acetonitrile (30 mL). The reaction mixture was stirred at room temperature for 4 hours. Water was added to the mixture and the precipitate formed collected to give the title compound as a powder (7.46 g, 100% yield).

Step B: N-[2-Chloro-6-methyl-4-(6-trifluoromethyl-3,4-dihydro-1H-isoquinolin-2-yl)-phenyl]-3,3-dimethylbutanamide

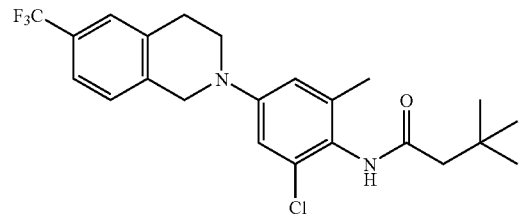

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 6-trifluoromethyl-1,2,3,4-tetrahydroisoquinoline hydrochloride salt (154 mg, 0.65 mmol) and N-(4-bromo-2-chloro-6-methylphenyl)-3,3-dimethylbutanamide (200 mg, 0.63 mmol) were then added and the reaction mixture was stirred at 90° C. overnight. The reaction mixture was then cooled to room temperature, concentrated and purified by thin layer chromatography (dichloromethane:methanol 5%) to afford the title compound as a solid.

$^1$H NMR (DMSO-$d_6$, 400 MHz) δ 1.08 (s, 9H), 2.17 (s, 3H), 2.21 (s, 2H), 3.0 (t, J=5.25 Hz, 2H), 3.6 (t, J=5.6 Hz, 2H), 4.5 (s, 2H), 6.9 (s, 1H), 6.95 (s, 1H), 7.3 (m, 1H), 7.5 (m, 2H), 9.13 (s, 1H).

Example 17

N-[2-Chloro-4-(6-chloro-3,4-dihydro-1H-isoquinolin-2-yl)-6-methyl-phenyl]-3,3-dimethylbutanamide Step A: N-(4-Bromo-2-chloro-6-methyl-phenyl)-3,3-dimethylbutanamide

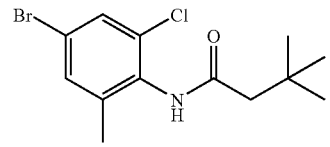

3,3-dimethylbutanoyl chloride (3.37 g, 3.5 mL, 25 mmol) and triethylamine (2.53 g, 3.5 mL, 25 mmol) were added to a solution of 4-Bromo-2-chloro-6-methyl-phenylamine (5.0 g, 25 mmol) in acetonitrile (30 mL). The reaction mixture was stirred at room temperature for 4 hours. Water was added to the mixture and the precipitate formed collected to give the title compound as a powder (7.46 g, 100% yield).

Step: N-[2-Chloro-4-(6-chloro-3,4-dihydro-1H-isoquinolin-2-yl)-6-methyl-phenyl]-3,3-dimethylbutanamide

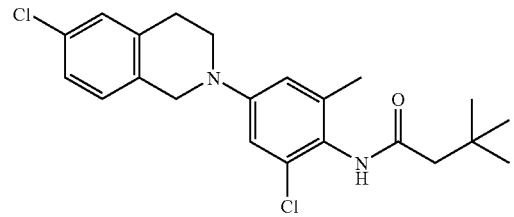

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 6-chloro-1,2,3,4-tetrahydroisoquinoline hydrochloride salt (133 mg, 0.65 mmol), and N-(4-bromo-2-chloro-6-methylphenyl)-3,3-dimethylbutanamide (200 mg, 0.63 mmol) were then added, and the reaction mixture was stirred at 90° C. overnight. The reaction mixture was then cooled to room temperature, concentrated, and purified by thin layer chromatography (dichloromethane:methanol 5%) to afford the title compound as a solid.

$^1$H NMR (DMSO-d$_6$, 400 MHz) δ 1.06 (s, 9H), 2.14 (s, 3H), 2.18 (s, 2H), 2.9 (t, J=5.25 Hz, 2H), 3.5 (t, J=5.6 Hz, 2H), 4.4 (s, 2H), 6.85 (s, 1H), 6.9 (s, 1H), 7.25 (m, 3H), 9.1 (s, 1H).

Example 18

N-[2-Chloro-4-(6-fluoro-3,4-dihydro-1H-isoquinolin-2-yl)-phenyl]-3,3-dimethylbutanamide Step A: N-(4-Bromo-2-chloro-phenyl)-3,3-dimethylbutanamide

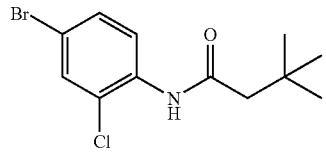

3,3-Dimethylbutanoyl chloride (717 mg, 0.74 mL, 5.32 mmol) was added to a solution of 4-Bromo-2-chloro-phenylamine (1.0 g, 4.84 mmol) in acetonitrile (10 mL). The reaction mixture was stirred at room temperature overnight. Water was added to the mixture and the precipitate formed collected to give the title compound as a powder (1.04 g, 72% yield).

Step B: N-[2-Chloro-4-(6-fluoro-3,4-dihydro-1H-isoquinolin-2-yl)-phenyl]-3,3-dimethylbutanamide The synthesis of this compound was performed as described in example 4, step C.

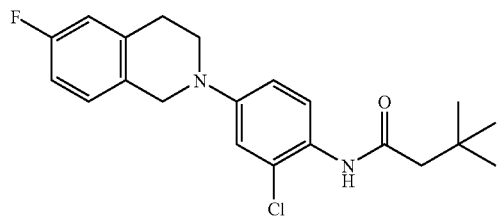

$^1$H NMR (DMSO-d$_6$, 400 MHz) δ 1.04 (s, 9H), 2.19 (s, 2H), 2.93 (t, J=8 Hz, 2H), 3.54 (t, J=8 Hz, 2H), 4.37 (s, 2H), 6.96 (dd, J=4, 12 Hz, 1H), 7.04 (m, 3H), 7.27 (m, 1H), 7.34 (d, J=8 Hz, 1H), 9.17 (s, 1H).

Example 19

N-[4-(6-Fluoro-3,4-dihydro-]-isoquinolin-2-yl)-2-methyl-phenyl)-3,3-dimethylbutanamide Step A: N-(4-Bromo-2-methyl-phenyl)-3,3-dimethylbutanamide

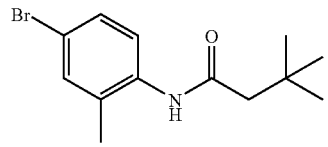

3,3-Dimethylbutanoyl chloride (724 mg, 0.75 mL, 5.4 mmol) was added to a solution of 4-Bromo-2-methyl-phenylamine (1.0 g, 5.4 mmol) in acetonitrile (10 mL). The reaction mixture was stirred at room temperature overnight. Water was added to the mixture and the precipitate formed collected to give the title compound as a powder (830 mg, 56% yield).

Step B: N-[4-(6-Fluoro-3,4-dihydro-1H-isoquinolin-2-yl)-2-methyl-phenyl]-3,3-dimethylbutanamide The synthesis of this compound was performed as described in example 4, step C.

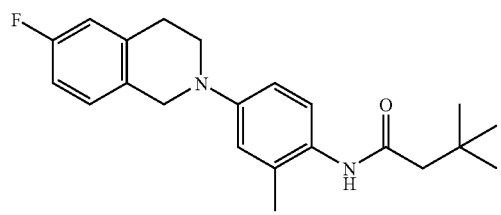

$^1$H NMR (DMSO-d$_6$, 400 MHz) δ 1.04 (s, 9H), 2.14 (s, 3H), 2.16 (s, 2H), 2.91 (t, J=8 Hz, 2H), 3.48 (t, J=8 Hz, 2H), 4.31 (s, 2H), 6.8 (dd, J=4, 12 Hz, 1H), 6.85 (s, 1H), 7.0 (m, 2H), 7.09 (d, J=8 Hz, 1H), 7.3 (m, 1H), 8.98 (s, 1H).

Example 20

N-[4-(6-Fluoro-3,4-dihydro-1H-isoquinolin-2-yl)-2-trifluoromethylphenyl]-3,3-dimethylbutanamide Step A: N-(4-Bromo-2-trifluoromethyl-phenyl)-3,3-dimethylbutanamide

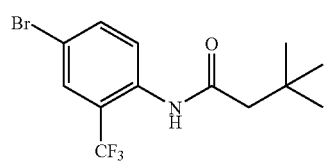

3,3-Dimethylbutanoyl chloride (617 mg, 0.64 mL, 4.6 mmol) was added to a solution of 4-Bromo-2-trifluoromethyl-phenylamine (1.0 g, 4.16 mmol) in acetonitrile (10 mL). The reaction mixture was stirred at room temperature overnight. Water was added to the mixture and the precipitate formed collected to give the title compound as a powder (1.1 g, 79% yield).

Step B: N-[4-(6-Fluoro-3,4-dihydro-1H-isoquinolin-2-yl)-2-trifluoromethyl-phenyl]-3,3-dimethylbutanamide The synthesis of this compound was performed as described in example 4, step C.

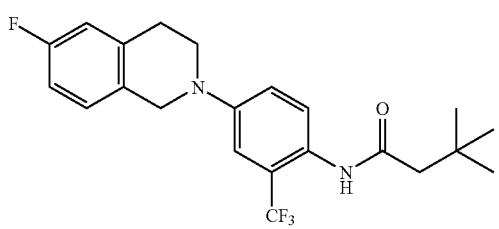

$^1$H NMR (DMSO-d$_6$, 400 MHz) δ 1.02 (s, 9H), 2.18 (s, 2H), 2.94 (t, J=8 Hz, 2H), 3.59 (t, J=8 Hz, 2H), 4.43 (s, 2H), 7.0 (m, 2H), 7.17 (m, 3H), 7.3 (m, 1H), 9.18 (s, 1H).

Example 21

N-[2-Chloro-4-(6-trifluoromethyl-3,4-dihydro-1H-isoquinolin-2-yl)-phenyl]-3,3-dimethylbutanamide Step A:
N-(4-Bromo-2-chloro-phenyl)-3,3-dimethylbutanamide

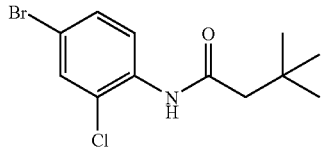

3,3-Dimethylbutanoyl chloride (717 mg, 0.74 mL, 5.32 mmol) was added to a solution of 4-Bromo-2-chloro-phenylamine (1.0 g, 4.84 mmol) in acetonitrile (10 mL). The reaction mixture was stirred at room temperature overnight. Water was added to the mixture and the precipitate formed collected to give the title compound as a powder (1.04 g, 72% yield).

Step B: N-[2-Chloro-4-(6-trifluoromethyl-3,4-dihydro-1H-isoquinolin-2-yl)-phenyl]-3,3-dimethylbutanamide

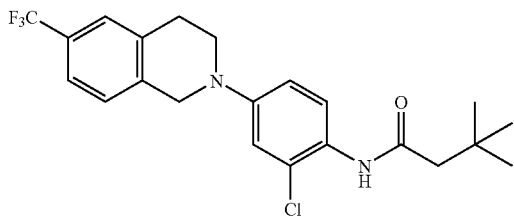

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 6-trifluoromethyl-1,2,3,4-tetrahydroisoquinoline hydrochloride salt (154 mg, 0.65 mmol) and N-(4-bromo-2-chloro)-3,3-dimethylbutanamide (200 mg, 0.66 mmol) were then added and the reaction mixture was stirred at 90° C. overnight. The reaction mixture was then cooled to room temperature, concentrated, and purified by thin layer chromatography (dichloromethane:methanol 5%) to afford the title compound as a solid.

$^1$H NMR (DMSO-d$_6$, 400 MHz) δ 1.03 (s, 9H), 2.19 (s, 2H), 2.99 (t, J=8 Hz, 2H), 3.58 (t, J=8 Hz, 2H), 4.48 (s, 2H), 6.99 (dd, J=4, 8 Hz, 1H), 7.08 (d, J=4 Hz, 1H), 7.35 (dd, J=4, 8 Hz, 1H), 7.48 (dd, J=4, 8 Hz, 1H), 7.56 (m, 2H), 9.19 (s, 1H).

Example 22

N-[4-(7-Fluoro-3,4-dihydro-1H-isoquinolin-2-yl)-2-trifluoromethyl-phenyl]-3,3-dimethylbutanamide Step A: N-(4-Bromo-2-trifluoromethyl-phenyl)-3,3-dimethyl-butanamide

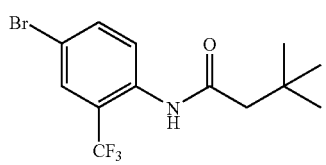

3,3-Dimethylbutanoyl chloride (617 mg, 0.64 mL, 4.6 mmol) was added to a solution of 4-Bromo-2-trifluoromethyl-phenylamine (1.0 g, 4.16 mmol) in acetonitrile (10 mL). The reaction mixture was stirred at room temperature overnight. Water was added to the mixture and the precipitate formed collected to give the title compound as a powder (1.1 g, 79% yield).

Step B: N-[4-(7-Fluoro-3,4-dihydro-1H-isoquinolin-2-yl)-2-trifluoromethyl-phenyl]-3,3-dimethylbutanamide

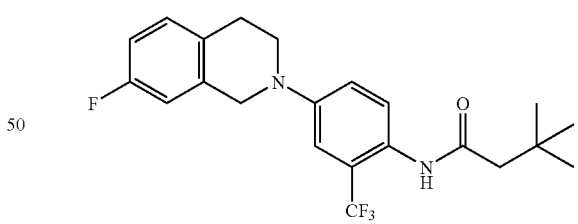

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 7-Fluoro-1,2,3,4-tetrahydroisoquinoline hydrochloride salt (122 mg, 0.65 mmol) and N-(4-bromo-2-trifluoromethyl)-3,3-dimethylbutanamide (200 mg, 0.59 mmol) were then added and the reaction mixture was stirred at 90° C. overnight. The reaction mixture was then cooled to room temperature, concentrated and purified by thin layer chromatography (dichloromethane 100%) to afford the title compound as a solid.

$^1$H NMR (DMSO-d$_6$, 400 MHz) δ 1.02 (s, 9H), 2.18 (s, 2H), 2.90 (t, J=8 Hz, 2H), 3.60 (t, J=8 Hz, 2H), 4.46 (s, 2H), 7.0 (m, 1H), 7.23 (m, 5H), 9.17 (s, 1H).

Example 23

3,3-Dimethyl-N-[2-trifluoromethyl-4-(7-trifluoromethyl-3,4-dihydro-1H-isoquinolin-2-yl)-phenyl]-butanamide Step A: N-(4-Bromo-2-trifluoromethyl-phenyl)-3,3-dimethylbutanamide

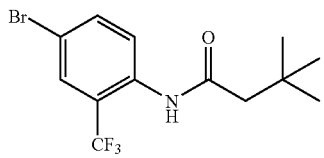

3,3-Dimethylbutanoyl chloride (617 mg, 0.64 mL, 4.6 mmol) was added to a solution of 4-Bromo-2-trifluoromethyl-phenylamine (1.0 g, 4.16 mmol) in acetonitrile (10 mL). The reaction mixture was stirred at room temperature overnight. Water was added to the mixture and the precipitate formed collected to give the title compound as a powder (1.1 g, 79% yield).

Step B: 3,3-Dimethyl-N-[2-trifluoromethyl-4-(7-trifluoromethyl-3,4-dihydro-1H-isoquinolin-2-yl)-phenyl]-butanamide

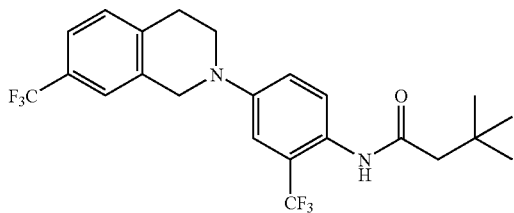

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 7-trifluoromethyl-1,2,3,4-tetrahydroisoquinoline hydrochloride salt (154 mg, 0.65 mmol) and N-(4-bromo-2-trifluoromethyl)-3,3-dimethylbutanamide (200 mg, 0.59 mmol) were then added and the reaction mixture was stirred at 90° C. overnight. The reaction mixture was then cooled to room temperature, concentrated and purified by thin layer chromatography (Dichloromethane 100%) to afford the title compound as a solid.

$^1$H NMR (DMSO-d$_6$, 400 MHz) δ 1.02 (s, 9H), 2.18 (s, 2H), 3.01 (t, J=8 Hz, 2H), 3.62 (t, J=8 Hz, 2H), 4.56 (s, 2H), 7.24 (m, 3H), 7.44 (d, J=4 Hz, 1H), 7.52 (d, J=4 Hz, 1H), 7.67 (s, 1H), 9.18 (s, 1H).

Example 24

N-[4-(6-Methoxy-3,4-dihydro-1H-isoquinolin-2-yl)-2,6-dimethyl-phenyl]-3,3-dimethyl butanamide Step A: N-(4-Bromo-2,6-dimethyl-phenyl)-3,3-dimethyl-butanamide

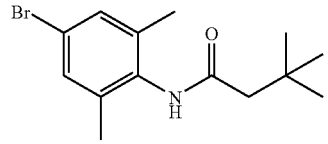

3,3-Dimethylbutanoyl chloride (3.37 g, 3.5 mL, 25 mmol) and triethylamine (2.53 g, 3.5 mL, 25 mmol) were added to a solution of 4-Bromo-2,6-dimethyl-phenylamine (5.0 g, 25 mmol) in acetonitrile (30 mL). The reaction mixture was stirred at room temperature for 4 hours. Water was added to the mixture and the precipitate formed collected to give the title compound as a powder (7.46 g, 100% yield).

Step B: N-[4-(6-Methoxy-3,4-dihydro-1H-isoquinolin-2-yl)-2,6-dimethyl-phenyl]-3,3-dimethylbutanamide

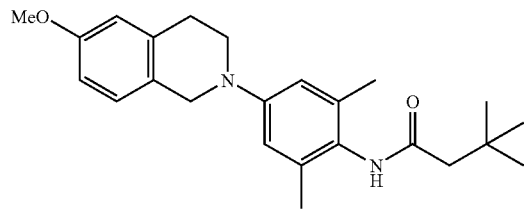

Bis(dibenzylidineacetone)palladium (2 mg, 0.0035 mmol) and (2'-dicyclohexyl phosphanyl-biphenyl-2-yl)-dimethylamine (3.3 mg, 0.0084 mmol) were added to dry toluene (10 mL purged with argon) and stirred for 15 minutes under argon. Potassium tert-butoxide (197 mg, 1.75 mmol), 6-methoxy-1,2,3,4-tetrahydroisoquinoline hydrochloride salt (134 mg, 0.67 mmol) and N-(4-bromo-2,6-dimethyphenyl)-3,3-dimethylbutanamide (200 mg, 0.67 mmol) were then added and the reaction mixture was stirred at 80° C. overnight. The reaction mixture was then cooled to room temperature, concentrated, filtered through a pad of silica gel, and recrystallized from toluene to afford the title compound as a solid.

$^1$H NMR (DMSO-d$_6$, 400 MHz) δ 1.05 (s, 9H), 2.10 (s, 6H), 2.14 (s, 2H), 2.87 (t, J=8 Hz, 2H), 3.48 (t, J=8 Hz, 2H), 3.72 (s, 3H), 4.26 (s, 2H), 6.68 (s, 2H), 6.79 (m, 2H), 7.14 (m, 1H), 8.85 (s, 1H).

Example 25

N-[2,6-Dimethyl-4-(7-trifluoromethyl-3,4-dihydro-1H-isoquinolin-2-yl)-phenyl]-3,3-dimethyl butanamide Step A: N-(4-Bromo-2,6-dimethyl-phenyl)-3,3-dimethylbutanamide

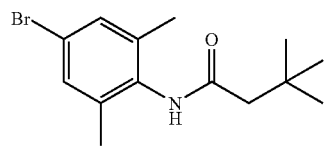

3,3-Dimethylbutanoyl chloride (3.37 g, 3.5 mL, 25 mmol) and triethylamine (2.53 g, 3.5 mL, 25 mmol) were added to a solution of 4-bromo-2,6-dimethyl-phenylamine (5.0 g, 25 mmol) in acetonitrile (30 mL). The reaction mixture was stirred at room temperature for 4 hours. Water was added to the mixture, and the precipitate that formed was collected to give the title compound as a powder (7.46 g, 100% yield).

Step B: N-[2,6-Dimethyl-4-(7-trifluoromethyl-3,4-dihydro-1H-isoquinolin-2-yl)-phenyl]-3,3-dimethyl-butanamide

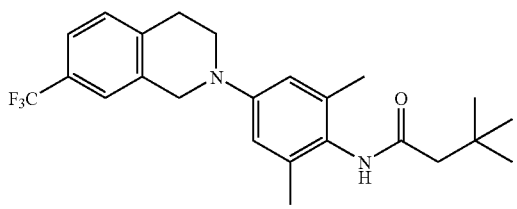

Bis(dibenzylidineacetone)palladium (390 mg, 0.68 mmol) and (2'-dicyclohexyl phosphanyl-biphenyl-2-yl)-dimethylamine (800 mg, 2.0 mmol) were added to dry toluene (150 mL purged with argon) and stirred for 15 minutes under argon. Potassium tert-butoxide (4.75 g, 42.3 mmol), 7-trifluoromethyl-1,2,3,4-tetrahydro-isoquinoline hydrochloride salt (4.82 g, 20.3 mmol) and N-(4-Bromo-2,6-dimethyl-phenyl)-3,3-dimethyl-butanamide (5 g, 16.8 mmol) were then added and the reaction mixture was stirred at 80° C. overnight. The reaction mixture was then cooled to room temperature, filtered through silica gel, and recrystallized from toluene to afford the title compound as a solid. (5.94 g, 85%).

$^1$H NMR (DMSO-d$_6$, 400 MHz) δ 1.06 (s, 9H), 2.11 (s, 6H), 2.18 (s, 2H), 2.89 (t, J=4 Hz, 2H), 3.54 (t, J=4 Hz, 2H), 4.44 (s, 2H), 6.73 (s, 2H), 7.40 (d, J=8 Hz, 1H), 7.51 (d, J=8 Hz, 1H), 7.62 (s, 1H), 8.87 (s, 1H).

Example 26

N-[4-(3,4-Dihydro-1H-isoquinolin-2-yl)-2-methoxy-6-methyl-phenyl]-3,3-dimethyl-butanamide Step A: 4-bromo-2-methoxy-6-methyl-aniline

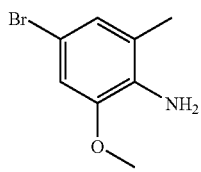

To an ice-water cooled solution of 2-methoxy-6-methylaniline (10 g, 72.9 mmol) in 30 mL of methanol and 10 mL of acetic acid was added dropwise bromine (3.75 mL, 72.9 mmol). The reaction mixture was allowed to stand for overnight. The solvent was removed under reduced pressure and the residue was suspended in 60 mL of 1N NaOH and extracted with ethyl acetate and dried over sodium sulfate and evaporated to dryness to give reddish crude product, which was recrystallized from hexane to give pure product (14.3 g, 91%).

Step B: (4-Bromo-2-methoxy-6-methyl-phenyl)-3,3-dimethyl butanamide

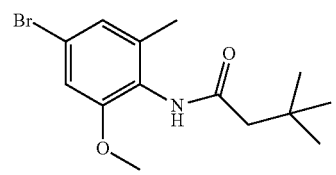

To a solution of 4-bromo-2-methoxy-6-methyl-aniline (2.2 g, 10 mmol) and triethylamine (1.5 g, 15 mmol) in anhydrous dichloromethane (50 mL) was added dropwise tert-butylacetyl chloride (1.6 g, 12 mmol) with stirring at room temperature. The reaction mixture was stirred for 3 hours at room temperature, than the reaction mixture was diluted with dichloromethane and washed with water and dried over anhydrous sodium sulfate and evaporated to dryness under reduced pressure. The residue was purified by silica gel column (ISCO, hexane/EtOAc, 0-40%, 40 min) to give a white solid (2.8 g, 89%).

Step C: N-[4-(3,4-Dihydro-1H-isoquinolin-2-yl)-2-methoxy-6-methyl-phenyl]-3,3-dimethyl-butanamide

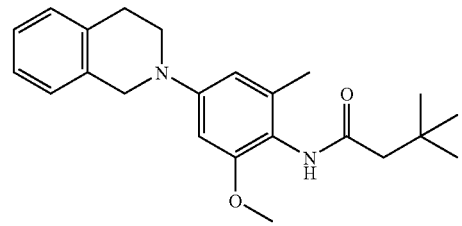

Toluene (6 ml) was degassed with nitrogen for 15 min in a 10 mL of microwave tube, then (4-bromo-2-methoxy-6-methyl-phenyl)-3,3-dimethyl-butanamide (188 mg, 0.6 mmol) and 1,2,3,4-tetrahydroisoquinoline (96 mg, 0.72 mmol) was added, followed by potassium tert-butoxide (101 mg, 0.9 mmol), bis(dibenzylidene acetone)palladium (17 mg, 0.03 mmol), and 2-dicyclohexyphosphino-2-(N,N-dimethylamino)biphenyl (24 mg, 0.06 mmol). The reaction tube was sealed and reacted in microwave at 100° C. for 2 hours. The reaction mixture was purified by silica gel column (ISCO, hexane/EtOAc, 0-40%, 40 min) to give pure compound as a white solid.

$^1$H-NMR (DMSO-d$_6$, 400 MHz): δ 8.64 (brs, 1H, exchangeable with D$_2$O), 7.20 (m, 4H), 6.48 (s, 1H), 6.43 (s, 1H), 4.37 (s, 2H), 3.73 (s, 3H), 3.52 (t, J=6.0 Hz, 2H), 2.92 (t, J=6.0 Hz, 2H), 2.13 (s, 2H), 2.08 (S, 3H), 1.04 (s, 9H). MS: 367 (M+1).

Example 27

N-[2-Chloro-4-(3,4-dihydro-1H-isoquinolin-2-yl)-6-trifluoromethoxy-phenyl]-3,3-dimethyl-butanamide Step A: N-(4-Bromo-2-chloro-6-trifluoromethoxy-phenyl)-3,3-dimethyl-butanamide

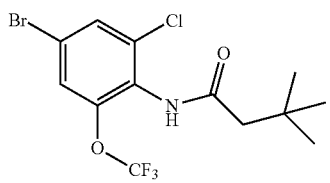

To a solution of 4-bromo-2-chloro-6-trifluoromethoxy-aniline (2.9 g, 10 mmol) and triethylamine (1.5 g, 15 mmol) in anhydrous dichloromethane (50 mL) was added dropwise tert-butylacetyl chloride (1.6 g, 12 mmol) with stirring at room temperature. The reaction mixture was stirred for 3 hours at room temperature, than the reaction mixture was diluted with dichloromethane and washed with water and dried over anhydrous sodium sulfate and evaporated to dryness under reduced pressure. The residue was purified by silica gel column (ISCO, hexane/EtOAc, 0-40%, 40 min) to give a white solid (3.6 g, 93%).

Step B: N-[2-Chloro-4-(3,4-dihydro-1H-isoquinolin-2-yl)-6-trifluoromethoxy-phenyl]-3,3-dimethylbutanamide

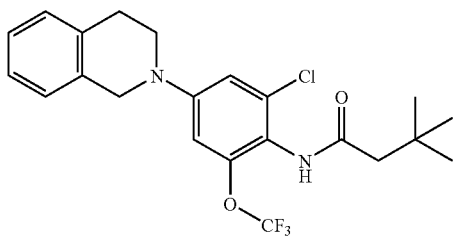

Synthesized according to example 26: $^1$H-NMR (DMSO-$d_6$, 400 MHz): δ 9.28 (brs, 1H, exchangeable with $D_2O$), 7.20 (m, 4H), 7.10 (s, 1H), 6.89 (s, 1H), 4.45 (s, 2H), 3.57 (t, J=6.0 Hz, 2H), 2.92 (t, J=6.0 Hz, 2H), 2.18 (s, 2H), 1.04 (s, 9H). MS: 441 (M+1).

Example 28

N-[4-(3,4-Dihydro-1H-isoquinolin-2-yl)-2,6-dimethoxy-phenyl]-3,3-dimethyl-butanamide Step A: 5-Bromo-1,3-dimethoxy-2-nitro-benzene

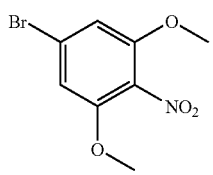

1-Bromo-3,5-dimethoxybenzene (10.9 g, 50 mmol) was dissolved in 100 mL of acetic anhydride and cooled to 0° C. A cooled solution of 70% $HNO_3$ (6.4 mL, 100 mmol) in 20 mL of acetic anhydride was added dropwise and the resulting mixture was stirred for 1 hour at 0° C. and for 3 hours at room temperature. The reaction mixture was poured into ice-water with strong stirring and the yellow solid was filtered and washed with water. The solid as a mixture of two isomers was separated by silica gel column (ISCO, hexane/EtOAc, 0-30%, 40 min) to give 3.3 g (25%) of pure 5-bromo-1,3-dimethoxy-2-nitro-benzene as an yellow solid. $^1$H-NMR (DMSO-$d_6$, 400 MHz): δ 7.17 (s, 2H), 3.89 (s, 6H).

Step B: 5-Bromo-1,3-dimethoxy-2-amino-benzene

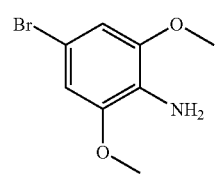

5-Bromo-1,3-dimethoxy-2-nitro-benzene (2.6 g, 10 mmol) was dissolved in 200 mL of methanol and 40 mL of water was added, followed by 2.5 g of Fe powder and 2.5 g of ammonium chloride. The mixture was heated to reflux at 80° C. for 2 hours and the cooled reaction mixture was filtered and washed with methanol. The filtrate was evaporated under reduce pressure to give the crude product, which was used for next step without further purification.

Step C: N-(4-Bromo-2,6-dimethoxy-phenyl)-3,3-dimethyl-butanamide

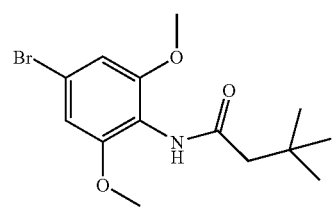

To a solution of the crude 5-bromo-1,3-dimethoxy-2-amino-benzene from above and triethylamine (1.5 g, 15 mmol) in anhydrous dichloromethane (50 mL) was added dropwise tert-butyl acetyl chloride (1.6 g, 12 mmol) with stirring at room temperature. The reaction mixture was stirred for 3 hours at room temperature. Then the reaction mixture was diluted with dichloromethane, washed with water, dried over anhydrous sodium sulfate, and evaporated to dryness under reduced pressure. The residue was purified by silica gel column (ISCO, hexane/EtOAc, 0-40%, 40 min) to give a white solid (3.0 g, 91%). $^1$H-NMR (DMSO-$d_6$, 400 MHz): δ 8.69 (brs, 1H, exchangeable with $D_2O$), 6.87 (s, 2H), 3.73 (s, 6H), 2.11 (s, 2H), 1.02 (s, 9H).

Step D: N-[4-(3,4-Dihydro-1H-isoquinolin-2-yl)-2,6-dimethoxy-phenyl]-3,3-dimethyl-butanamide

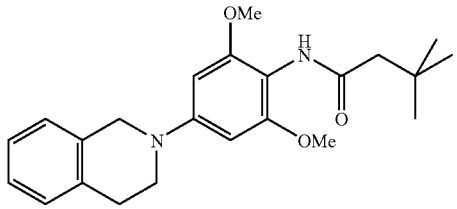

Toluene (6 mL) was degassed with nitrogen for 15 min in a 10 mL of microwave tube, then N-(4-bromo-2,6-dimethoxy phenyl)-3,3-dimethyl butanamide (200 mg, 0.6 mmol) and 1,2,3,4-tetrahydroisoquinoline (96 mg, 0.72 mmol) was added, followed by potassium tert-butoxide (101 mg, 0.9 mmol), bis(dibenzylidene acetone)palladium (17 mg, 0.03 mmol), and 2-dicyclohexyphosphino-2-(N,N-dimethylamino)biphenyl (24 mg, 0.06 mmol). The reaction tube was sealed and reacted in microwave at 100° C. for 2 hours. The reaction mixture was purified by silica gel column (ISCO, hexane/EtOAc, 0-40%, 40 min) to give pure compound as a white solid. $^1$H-NMR (DMSO-$d_6$, 400 MHz): δ 8.36 (brs, 1H, exchangeable with $D_2O$), 7.20 (m, 4H), 6.25 (s, 2H), 4.41 (s, 2H), 3.72 (s, 6H), 3.55 (t, J=6.0 Hz, 2H), 2.95 (t, J=6.0 Hz, 2H), 2.07 (s, 2H), 1.03 (s, 9H). MS: 383 (M+1).

Example 28

N-[2,6-Dimethyl-4-(6-trifluoromethyl-3,4-dihydro-1H-isoquinolin-2-yl)-phenyl]-3,3-dimethyl-thiobutanamide Step A: N-(4-Bromo-2,6-dimethyl-phenyl)-3,3-dimethyl-butyramide

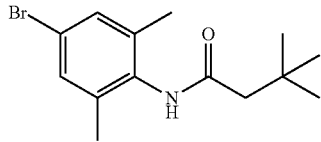

3,3-dimethylbutanoyl chloride (3.37 g, 3.5 mL, 25 mmol) and triethylamine (2.53 g, 3.5 mL, 25 mmol) were added to a solution of 4-Bromo-2,6-dimethyl-phenylamine (5.0 g, 25 mmol) in acetonitrile (30 mL). The reaction mixture was stirred at room temperature for 4 hours. Water was added to the mixture and the precipitate formed collected to give the title compound as a powder (7.46 g, 100% yield).

Step B: N-[2,6-Dimethyl-4-(6-trifluoromethyl-3,4-dihydro-1H-isoquinolin-2-yl)-phenyl]-3,3-dimethyl-butanamide

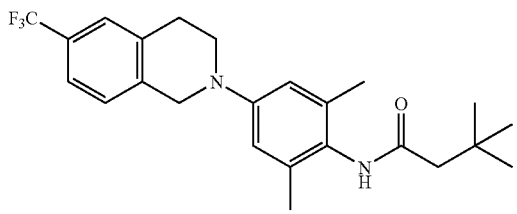

Bis(dibenzylidineacetone)palladium (390 mg, 0.68 mmol) and (2'-dicyclohexylphosphanyl-biphenyl-2-yl)-dimethylamine (800 mg, 2.0 mmol) were added to dry toluene (150 mL purged with argon) and stirred for 15 minutes under argon. Potassium tert-butoxide (4.75 mg, 42.3 mmol), 6-Trifluoromethyl-1,2,3,4-tetrahydro-isoquinoline hydrochloride salt (4.82 g, 20.3 mmol) and N-(4-Bromo-2,6-dimethyl-phenyl)-3,3-dimethyl-butyramide (5 g, 16.8 mmol) were then added and the reaction mixture was stirred at 80° C. over night. The reaction mixture was then cooled to room temperature and recrystallized from toluene to afford the title compound as a solid. (5.55 g, 79%).
$^1$H NMR (DMSO-$d_6$, 500 MHz) δ 1.03 (s, 9H), 2.09 (s, 6H), 2.15 (s, 2H), 2.98 (t, J=5.0 Hz, 2H), 3.52 (t, J=6.0 Hz, 2H), 4.40 (s, 2H), 6.71 (s, 2H), 7.45 (d, J=8.0, 1H), 7.52 (m, 2H), 8.87 (s, 1H).

Step C: N-[2,6-Dimethyl-4-(6-trifluoromethyl-3,4-dihydro-1H-isoquinolin-2-yl)-phenyl]-3,3-dimethyl-thiobutanamide

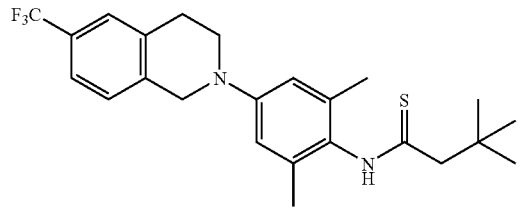

To a solution of N-[2,6-Dimethyl-4-(6-trifluoromethyl-3,4-dihydro-1H-isoquinolin-2-yl)-phenyl]-3,3-dimethyl-butyramide (200 mg, 0.48 mmol) in dichloroethane (10 mL) was added Lawesson's reagent (193 mg, 0.48 mmol) and the reaction mixture was stirred at reflux for 2 h. The mixture was then cooled to room temperature and concentrate. Purification by preparative thin layer chromatography (dichloromethane 100%) afforded the desired compound as a solid.
$^1$H NMR (DMSO-$d_6$, 400 MHz) δ 1.12 (s, 9H), 2.11 (s, 6H), 2.73 (s, 2H), 3.0 (t, J=5.0 Hz, 2H), 3.57 (t, J=4.0 Hz, 2H), 4.46 (s, 2H), 6.75 (s, 2H), 7.47 (d, J=8.0, 1H), 7.56 (m, 2H), 10.7 (s, 1H).

Example 29

[2,6-Dimethyl-4-(6-trifluoromethyl-3,4-dihydro-1H-isoquinolin-2-yl)-phenyl]-carbamic acid ethyl ester Step A: (4-Bromo-2,6-dimethyl-phenyl)-carbamic acid ethyl ester

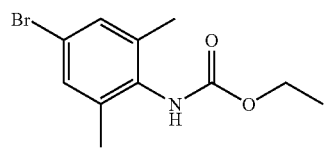

Ethyl chloroformate (0.55 g, 0.48 mL, 5 mmol) was added to a solution of 4-bromo-2,6-dimethyl-phenylamine (1.0 g, 5 mmol) in acetonitrile (20 mL). The reaction mixture was stirred at reflux for 16 hours. Water was added to the mixture and the precipitate formed collected to give the title compound as a powder (1.32 g, 97% yield).

Step B: [2,6-Dimethyl-4-(6-trifluoromethyl-3,4-di-hydro-1H-isoquinolin-2-yl)-phenyl]-carbamic acid ethyl ester

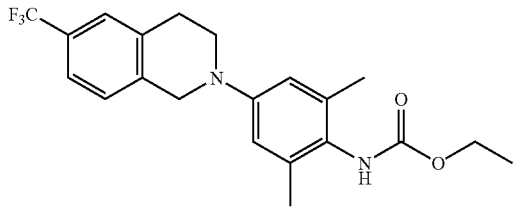

Bis(dibenzylidineacetone)palladium (17 mg, 0.03 mmol) and (2'-dicyclohexylphosphanyl-biphenyl-2-yl)-dimethylamine (35 mg, 0.09 mmol) were added to dry toluene (5 mL purged with argon) and stirred for 15 minutes under argon. Potassium tert-butoxide (166 mg, 1.48 mmol), 6-Trifluoromethyl-1,2,3,4-tetrahydro-isoquinoline hydrochloride salt (176 mg, 0.74 mmol) and (4-Bromo-2,6-dimethyl-phenyl)-carbamic acid ethyl ester (200 mg, 0.74 mmol) were then added and the reaction mixture was stirred at 80° C. overnight. The reaction mixture was then cooled to room temperature filtered through silica gel and purified by preparative thin layer chromatography (DCM 100%) to give the desired compound as a solid.

$^1$H NMR (DMSO-$d_6$, 400 MHz) δ 1.23 (t, J=7.2 Hz, 3H), 2.12 (s, 6H), 3.0 (t, J=6.4 Hz, 2H), 3.52 (t, J=6.3 Hz, 2H), 4.08 (q, J=13.6, 8.3 Hz, 2H), 4.42 (s, 2H) 6.73 (s, 2H), 7.46 (d, J=7.4, 1H), 7.54 (m, 2H), 8.32 (s, 1H).

Biological Results

Compounds of this invention formula were evaluated for activity toward potassium channels in a cell-based $Rb^+$ efflux assay This cellular bioassay is believed to faithfully represent the M current channel activities identified with KCNQ2/3 heteromultimers. The most active compounds of this invention have $EC_{50}$s in the single-digit nM range, which represents a 40- to 400-fold improvement over retigabine. Additionally, antiseizure activity in vivo was evaluated in a mouse maximal electroshock seizure (MES) model, and neurotoxicities were determined from a rotorod neurocognitive motor impairment model.

Methods:
Rubidium Efflux Test

PC-12 cells were grown at 37° C. and 5% $CO_2$ in DMEM/F12 Medium (Dulbecco's Modified Eagle Medium with Nutrient Mix F-12, available from Invitrogen of Carlsbad, Calif.), supplemented with 10% horse serum, 5% fetal bovine serum, 2 mM glutamine, 100 U/ml penicillin, and 100 U/ml streptomycin. They were plated in poly-D-lysine-coated 96-well cell culture microplates at a density of 40,000 cells/well and differentiated with 100 ng/ml NGF-7s for 2-5 days. For the assay, the medium was aspirated, and the cells were washed once with 0.2 ml in wash buffer (25 mM HEPES, pH 7.4, 150 mM NaCl, 1 mM $MgCl_2$, 0.8 mM $NaH_2PO_4$, 2 mM $CaCl_2$). The cells were then loaded with 0.2 ml $Rb^+$ loading buffer (wash buffer plus 5.4 mM $RbCl_2$, 5 mM glucose) and incubated at 37° C. for 2 h. Attached cells were quickly washed three times with buffer (same as $Rb^+$ loading buffer, but containing 5.4 mM KCl instead of RbCl) to remove extracellular $Rb^+$. Immediately following the wash, 0.2 ml of depolarization buffer (wash buffer plus 15 mM KCl) with or without compounds was added to the cells to activate efflux of potassium ion channels. After incubation for 10 min at room temperature, the supernatant was carefully removed and collected. Cells were lysed by the addition of 0.2 ml of lysis buffer (depolarization buffer plus 0.1% Triton X-100) and the cell lysates were also collected. If collected samples were not immediately analyzed for $Rb^+$ contents by atomic absorption spectroscopy (see below), they were stored at 4° C. without any negative effects on subsequent $Rb^+$ analysis.

The concentrations of $Rb^+$ in the supernatants ($Rb^+_{Sup}$) and the cell lysates ($Rb^+_{Lys}$) were quantified using an ICR8000 flame atomic absorption spectrometer (Aurora Biomed Inc., Vancouver, B.C.) under conditions defined by the manufacturer. Samples 0.05 ml in volume were processed automatically from microtiter plates by dilution with an equal volume of $Rb^+$ sample analysis buffer and injection into an air-acetylene flame. The amount of $Rb^+$ in the sample was measured by absorption at 780 nm using a hollow cathode lamp as light source and a PMT detector. A calibration curve covering the range 0-5 mg/L $Rb^+$ in sample analysis buffer was generated with each set of plates. The percent $Rb^+$ efflux (F) was defined by $$F=[Rb^+_{Sup}/(Rb^+_{Sup}+Rb^+_{Lys})]\times 100\%.$$

where the $F_c$ is the efflux in the presence of compound in depolarization buffer, $F_b$ is the efflux in basal buffer, and $F_s$ is the efflux in depolarization buffer, and $F_c$ is the efflux in the presence of compound in depolarization buffer. The efflux (F) and compound concentration relationship was plotted to calculate an $EC_{50}$ value, a compound's concentration for 50% of maximal $Rb^+$ efflux. The results are shown below.

Maximal Electroshock Seizure (MES) and Acute Toxicity Tests

MES Test

The MES testing protocol is based on procedures established at the National Institute of Neurological Disorders and Stroke in conjunction with the Anticonvulsant Screening Program (ASP) at the University of Utah (White, H. S., Woodhead, J. H., Wilcox, K. S., Stables, J. P., Kupferberg, H. J and Wolf, H. H. 2002. "General Principles: Discovery and Preclinical Development of Antiepileptic Drugs," in *Antiepileptic Drugs*, 5$^{th}$ Edition, R. H. Levy, ed.; R. H. Mattson, B. S. Meldrum, and E. Perucca. Philadelphia, Lippincott Williams & Wilkins.), The goal of the test rapid identification and characterization of the in vivo anticonvulsant activity of any compounds that have been shown active in PC-12 cellular based $Rb^+$ efflux assay.

Adult male CF-1 albino mice (18-25 g, Charles River Laboratories) are exclusively used for in-house MES screen of compounds. Male Sprague-Dawley albino rats (100-125 g, Charles River Laboratories) are also used to test anticonvulsant compounds. Variability of test outcomes is reduced by using animals of the same sex, age, and weight. Animals are permitted to rest and recover from transit for at least 48 hr prior to experimentation. Animals are used for AED testing only once. In some instances, the animals may be anesthetized prior to blood collection and/or whole brain extraction for pharmacokinetic assay. All animals are maintained and handled as outlined in standard animal care guidelines.

In the experiments, testing compounds are prepared as suspensions in 0.5% methyl cellulose (Sigma, Cat # M0512, Viscosity 4000 cP at 20° C.) in water, regardless of solubility. Dry powder compounds are initially ground with a glass rod in a test tube in several drops of methyl cellulose to create a paste and to break down any large chunks. After several minutes of grinding, the volume of the suspension is increased to the final concentration desired. The suspension is then sonicated using a Branson sonicator model 3510 in a water bath at room temperature for 15 minutes. Compound suspensions are further vortexed prior to animal dosing. In some of the cases, DMSO is used to initially solubilize compounds in small volumes and then this solution is added to the 0.5% methyl cellulose solution, in order to create more even and less aggregated compound suspensions. The final concentration of DMSO is 3.75%, an amount with no apparent toxicity or neuroprotective effects in our usual rotarod and MES tests. Methyl cellulose/DMSO compound suspensions are identically prepared for intraperitoneally (i.p.) to mice or orally (p.o.) to rat dosing.

Initially the animals are weighed with an electronic scale and then marked. Data recording sheets are generated for each compound assessment. Mice or rats are dosed with the compound suspension at 0.01 mL/g of body weight. The typical injection volume range is between 180-250 µl for mice. Compounds are dosed by i.p. to mice using a 25 or 22 gauge needle, depending on the viscosity of the suspension. Rats are p.o. dosed using a flexible feeding tube, typically starting at a compound dose of 5 mg/kg.

A Rodent Electroconvulsive Stimulator (Model 200, Hamit-Darvin-Freesh, Snow Canyon Clinic, Ivins, Utah) is used for MES testing. A 60-Hz alternating current (50 mA for mice; 150 mA for rats) is delivered for 0.2 seconds through corneal electrodes to the mice. A drop of 0.5% tetracaine (Sigma, Cat. # T-7508) solution is placed on the eye prior to current delivery. The electrodes are subsequently placed gently onto the eyes of the animal and the electrical shock is initiated by triggering through a foot-pedal activator. The animals are restrained by hand and gently released as the shock is delivered and the seizure commences. Animals are monitored for hind limb tonic extension as the end point for this test. Current delivery is recorded as a measure of overall seizure-induction potential. Electrical current delivery can vary from approximately 30-55 mA (mice) or 90-160 mA (rats) depending on impedance in the animal and quality of the current delivery (ie. correct placement of the electrodes on the cornea). Seizures will be successfully induced in control animals throughout this current range. Tonic extension is considered abolished if the hind limbs fail to become fully extended at 180° with the plane of the body. Lack of tonic extension suggests that the test compound has prevented the spread of seizure discharge through neural tissue. Although unnecessary in mice, the rats are pre-screened for seizure induction potential using the MES 24 hr prior to compound dosing and the subsequent MES test. A success rate of 92-100% has been determined for the rat seizure induction potential. Rats that fail to develop tonic/clonic seizures during the pre-screening are not used for drug testing.

For a compound testing, time-to-peak effect studies are initially performed using 0.5, 1, 2, 4, 8 and 24 hr time points, typically using a single 5 or 25 mg/kg dose. The determined time-to-peak effect is used for further titration of a compound's potency ($ED_{50}$, the dose of a drug that protects 50% of animals from electrical induced seizure) in both mouse and rat models. For titrations, 8 animals are used per concentration and dose (normal 5 concentrations) is varied until a full dose response curve can be obtained. Probit analysis (ASP method) or non-linear regression analysis on Graph Pad (constraining the lower dose/effect value) is used to calculate an $ED_{50}$ value for the test compound.

Rotarod Test

Prior to MES testing, compound dosed mice are scrutinized for abnormal neurologic status as defined by motor impairment on a slowly turning (6 rpm) rotarod apparatus (Model 755, Series 8, IITC Life Sciences, Woodland Hills, Calif.). The inability of a mouse to maintain its balance on the rotarod over a period of one minute (three falls=failure) signifies motor impairment and hence acute toxicity. These measurements are done at the same time points as the MES assay. Untreated normal mice are able to maintain balance on the rotarod for at least one minute without falling. Median toxicity of a compound ($TD_{50}$, the dose of a drug that results in motor impairment in 50% of animals) is determined.

Open Field Test

Before MES test, compound treated rats are visually observed for acute toxicity signs for approximately one minute in the open field test. Here, rats are gently placed into a plexiglass enclosure and are monitored for behavior consistent with toxicity including ataxia, trembling, hypoactivity (including failure to seek the walls), hypersensitivity, lack of exploratory behavior and lack of avoidance of the open area. Typically if the rats exhibits two or more of these abnormal behaviors they are scored as toxic.

TABLE 1

| ACTIVITIES OF EXEMPLARY COMPOUNDS | | | |
|---|---|---|---|
| COMPOUND | Mouse $ED_{50}$ (mg/kg) | Rat $ED_{50}$ (mg/kg) | ACTIVITY $EC_{50}$ |
| 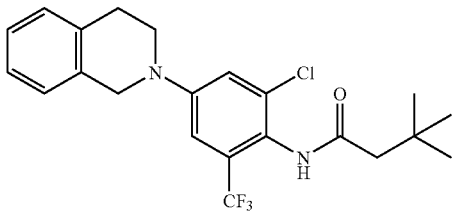 | γ | NA | B |
| 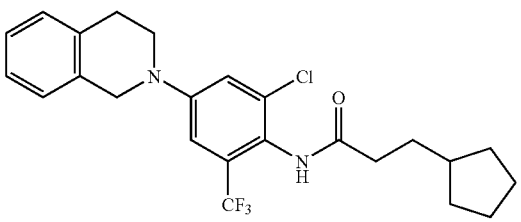 | γ | NA | B |

TABLE 1-continued

ACTIVITIES OF EXEMPLARY COMPOUNDS

| COMPOUND | Mouse ED$_{50}$ (mg/kg) | Rat ED$_{50}$ (mg/kg) | ACTIVITY EC$_{50}$ |
|---|---|---|---|
| (structure) | β | NA | C |
| (structure) | γ | NA | C |
| (structure) | β | NA | B |
| (structure) | β | α | C |
| (structure) | β | NA | B |
| (structure) | γ | NA | B |

TABLE 1-continued
ACTIVITIES OF EXEMPLARY COMPOUNDS
| COMPOUND | Mouse ED$_{50}$ (mg/kg) | Rat ED$_{50}$ (mg/kg) | ACTIVITY EC$_{50}$ |
|---|---|---|---|
| 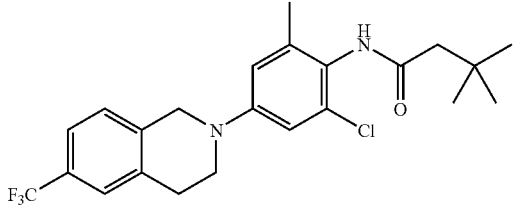 | γ | NA | B |
| 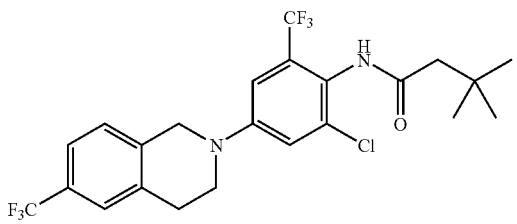 | γ | NA | B |
| 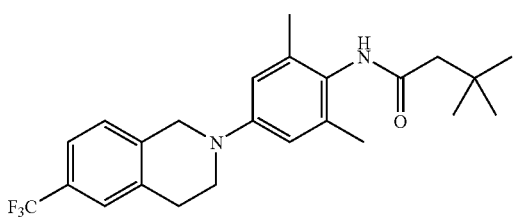 | α | α | B |
| 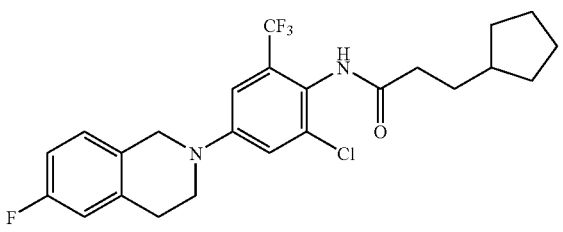 | γ | NA | A |
| 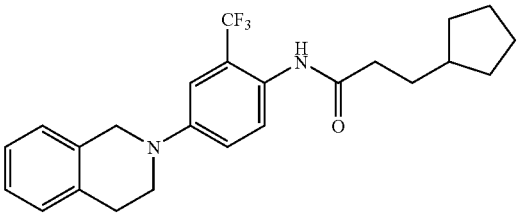 | NA | NA | C |
| 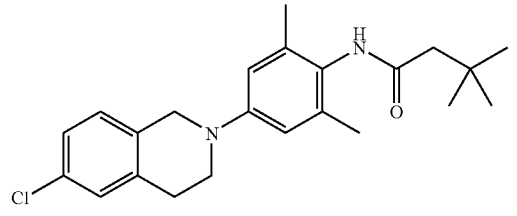 | β | NA | C |

TABLE 1-continued

ACTIVITIES OF EXEMPLARY COMPOUNDS

| COMPOUND | Mouse ED$_{50}$ (mg/kg) | Rat ED$_{50}$ (mg/kg) | ACTIVITY EC$_{50}$ |
|---|---|---|---|
| (6-chloro-tetrahydroisoquinoline, 2-Cl, 6-CF$_3$ phenyl, t-Bu amide) | γ | NA | C |
| (7-fluoro-tetrahydroisoquinoline, 2-Cl, 6-Me phenyl, t-Bu amide) | β | NA | B |
| (6-chloro-tetrahydroisoquinoline, 2-Me, 6-Cl phenyl, t-Bu amide) | β | NA | C |
| (7-fluoro-tetrahydroisoquinoline, 2-Cl, 6-CF$_3$ phenyl, t-Bu amide) | γ | NA | B |
| (6-fluoro-tetrahydroisoquinoline, 2-Me phenyl, t-Bu amide) | NA | NA | D |
| (6-fluoro-tetrahydroisoquinoline, 2-Cl phenyl, t-Bu amide) | γ | NA | D |

TABLE 1-continued

ACTIVITIES OF EXEMPLARY COMPOUNDS

| COMPOUND | Mouse ED$_{50}$ (mg/kg) | Rat ED$_{50}$ (mg/kg) | ACTIVITY EC$_{50}$ |
|---|---|---|---|
| *(6-fluoro-tetrahydroisoquinoline attached to 2-CF$_3$-aniline N-acyl-3,3-dimethylbutanamide)* | β | NA | D |
| *(6-CF$_3$-tetrahydroisoquinoline attached to 2-chloro-aniline N-acyl-3,3-dimethylbutanamide)* | γ | NA | D |
| *(7-CF$_3$-tetrahydroisoquinoline attached to 2,6-dimethyl-aniline N-acyl-3,3-dimethylbutanamide)* | α | α | B |
| *(tetrahydroisoquinoline attached to 2-methoxy-6-methyl-aniline N-acyl-3,3-dimethylbutanamide)* | β | NA | B |
| *(tetrahydroisoquinoline attached to 2-OCF$_3$-6-chloro-aniline N-acyl-3,3-dimethylbutanamide)* | γ | NA | B |
| *(tetrahydroisoquinoline attached to 2,6-dimethoxy-aniline N-acyl-3,3-dimethylbutanamide)* | α | α | C |

TABLE 1-continued

ACTIVITIES OF EXEMPLARY COMPOUNDS

| COMPOUND | Mouse ED$_{50}$ (mg/kg) | Rat ED$_{50}$ (mg/kg) | ACTIVITY EC$_{50}$ |
|---|---|---|---|
| [structure: 7-CF$_3$-tetrahydroisoquinoline linked to 2-CF$_3$-4-aminophenyl-NH-C(O)-CH$_2$-C(CH$_3$)$_3$] | β | NA | D |
| [structure: 6-methoxy-tetrahydroisoquinoline linked to 2,6-dimethyl-4-aminophenyl-NH-C(O)-CH$_2$-C(CH$_3$)$_3$] | γ | NA | D |
| [structure: 7-F-tetrahydroisoquinoline linked to 2-CF$_3$-4-aminophenyl-NH-C(O)-CH$_2$-C(CH$_3$)$_3$] | NA | NA | D |
| [structure: 6-CF$_3$-tetrahydroisoquinoline linked to 2,6-dimethyl-4-aminophenyl-NH-C(O)-O-ethyl] | NA | NA | C |
| [structure: 6-CF$_3$-tetrahydroisoquinoline linked to 2,6-dimethyl-4-aminophenyl-NH-C(S)-CH$_2$-C(CH$_3$)$_3$] | NA | NA | D |

Legend:
A: EC$_{50}$ ≦ 1 nM;
B: = 1 nM < EC$_{50}$ ≦ 10 nM;
C: 10 nM < EC$_{50}$ ≦ 50 nM;
D: 50 nM < EC$_{50}$ ≦ 500 nM
α: 0.12 < ED50 < 1.2
β: 1.2 < ED50 < 12
γ: 12 < ED50

Studies of KCNQ2/3 Opening Activity and KCNQ Subtype Selectivity Using Electrophysiological Patch clamp in *Xenopus* Oocytes Expression in *Xenopus Laevis* Oocytes Female *Xenopus laevis* extracted ovaries were purchased from eNASCO (LM00935MX, eNASCO Fort Atkinson, Wis.). Following manual dissection of the oocytes into smaller groups, the oocytes were defolliculated by enzymatic treatment with collagenase type 2 (LS004177, Worthington, Lakewood, N.J.) for 1½ hour in the presence of calcium-free Culture Bath solution (88 mM NaCl, 1 mM KCl, 0.82 mM MgSO$_4$, 2.4 mM NaHCO$_3$, and 5 mM HEPES, pH 7.5). Oocytes were then kept in supplemented Culture Bath solution (88 mM NaCl, 1 mM KCl, 0.82 mM MgSO$_4$, 0.9 mM CaCl$_2$, 2.4 mM NaHCO$_3$, 1 mM sodium pyruvate, 0.05 mg/ml Geneticin, 100 U/ml penicillin, 0.1 mg/ml streptomycin and 5 mM HEPES, pH 7.5) at 19° C. for 24 hours before injection of cRNA. Approximately 50 nl cRNA (about 50 ng)

was injected for KCNQ1, KCNQ4, and KCNQ5 using a Nanoject microinjector (Drummond, Broomall, Pa., USA). For co-expression of KCNQ2 and KCNQ3 and of KCNQ1 and KCNE1, cRNA's were mixed in equal molar ratios before injection of approximately 50 nl. The mixtures contained about 10+10 ng and 12.5+2.5 ng cRNA, respectively. The smaller amounts are needed because larger currents arise when KCNQ2/KCNQ3 and KCNQ1/KCNE1 are co-expressed. Oocytes were kept in Culture Barth solution at 19° C. which was changed daily and currents were recorded after 3 to 5 days.

Electrophysiology

KCNQ channel currents expressed in *Xenopus laevis* oocytes were recorded using a two-electrode voltage-clamp. The recordings were made at room temperature in recording solution (96 mM NaCl, 2 mM KCl, 1 mM $MgCl_2$, 1.8 mM $CaCl_2$, and 5 mM HEPES, pH 7.5) using a two-electrode voltage-clamp amplifier (OC-725C, Warner Instrument, Hamden, Conn., USA). The oocytes were placed in custom built perfusion chambers connected to a continuous flow system and impaled with a current electrode and a voltage-clamp electrode pulled from borosilicate glass on a Flaming/Brown Micropipette Puller (Sutter Instruments Co, Novato, Calif., USA). Recording electrodes were filled with 3 M KCl and had a resistance of 0.5 to 2.5 MΩ.

Compounds

All compounds were dissolved in DMSO to obtain concentrated stock solutions. On the day of electrophysiological experiments the stock solutions were thawed and diluted in recording solution to their final concentrations. The final DMSO concentration never exceeded 0.1%. Compound delivery was performed using a custom built multi-barrel apparatus connected to the flow system.

Calculations

Data were acquired by means of an Axograph X software (Axograph Scientific, Sydney, AU) and analyzed using Graph Pad Prism (GraphPad Software Inc., CA, USA).

Concentration—response curves were constructed by plotting the increase in steady-state current expressed in percentages as a function of drug concentration. During the course of the experiment, while various concentrations of the drug were being dosed, the resting voltage was held at −90 mV and pulsed to −60 mV, −40 mV, and −50 mV for 5 s for KCNQ2/KCNQ3, KCNQ4 and KCNQ5 channels respectively. The plot was then fitted to a Hill function:

$$Response = R2 + (R1-R2)/[1+(C/EC_{50})^{nH}]$$

where R1 is the initial response, R2 is the maximum response, C is the drug concentration and nH is the slope (Hill coefficient) of the curve.

The efficacy of compounds of this invention in comparison with Retigabine (as a positive control) was determined by recording the steady current using the above voltage protocol for the channels in the presence of the $EC_{75}$ of the drugs. After steady channel current was recorded in the presence of Retigabine at its EC75, recorded oocyte was washed with the recording solution until its steady current returned to its normal level without the presence of any drugs. Then the channel steady current was recorded in the presence of the test compound at its $EC_{75}$. The percent efficacy was then expressed as:

$$\% \; efficacy = (C2/C1) \times 100\%$$

where C2 is the recorded steady current in the presence of follow-on compound at its $EC_{75}$ and C1 is the recorded steady current in the presence of Retigabine at its $EC_{75}$.

What is claimed is:
1. A compound of formula IA

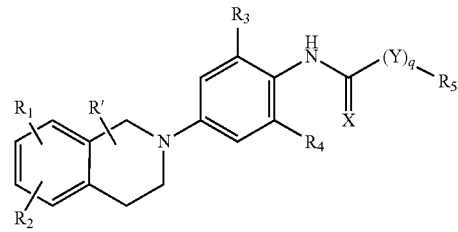

wherein
$R_1$ and $R_2$, vary independently, and are selected from the group consisting of H, CN, halogen, $CH_2CN$, OH, $CH_2F$, $CHF_2$, $CF_3$, $CF_2CF_3$, $C_1$-$C_6$ alkyl, C(=O)$C_1$-$C_6$ alkyl; NH—$C_1$-$C_6$ alkyl; N($C_1$-$C_6$ alkyl)-$C_1$-$C_6$ alkyl, NHC(=O)$C_1$-$C_6$ alkyl, C(=O)N($CH_3$)$_2$, C(=O)N(Et)$_2$, C(=O)$NH_2$, C(=O)NH—$C_1$-$C_6$alkyl, $SO_2NH_2$, $NHSO_2$—$C_1$-$C_6$ alkyl; C(=O)O$C_1$-$C_6$ alkyl, OC(=O)$C_1$-$C_6$ alkyl, O$C_1$-$C_6$ alkyl, S$C_1$-$C_6$ alkyl, $C_3$-$C_6$ cycloalkyl, $(CH_2)_m C_3$-$C_6$ cycloalkyl, $C_3$-$C_6$ cycloalkenyl, $(CH_2)_m C_3$-$C_6$ cycloalkenyl, $C_2$-$C_6$ alkenyl, $C_2$-$C_6$ alkynyl, Ar, $(CH_2)_m$thienyl, $(CH_2)_m$imidazolyl, $(CH_2)_m$pyrazyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, and $(CH_2)_m$pyrimidyl,
wherein
m=zero, 1, or 2;
Ar is a 5- to 10-member mono- or bicyclic aromatic group, optionally containing 1-4 ring heteroatoms selected independently from N, O, and S;
or
$R_1$ and $R_2$, together with the ring carbon atoms to which they are attached, form a 5- or 6-member fused ring;
wherein said fused ring may be saturated, unsaturated, or aromatic, and said fused ring optionally contains one or two heteroatoms selected independently from the group consisting of O, N, and S;
R' is selected from the group consisting of H, halogen, phenyl, 2-(N,N-dimethylamino)ethyl, $CF_3$, O$C_1$-$C_3$ alkyl and $C_1$-$C_3$ alkyl;
$R_3$ and $R_4$ vary independently, and are selected from the group consisting of H, CN, halogen, $CF_3$, $OCF_3$, O$C_1$-$C_3$ alkyl, and $C_1$-$C_3$ alkyl;
X is O or S;
Y is O or S;
q=1 or zero; and
$R_5$ is selected from the group consisting of $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, Ar, $(CHR_6)_w$Ar, $CH_2(CHR_6)_w$Ar, and $(CHR_6)_w CH_2$Ar,
wherein
w=zero, 1, 2, or 3;
Ar is a 5- to 10-member mono- or bicyclic aromatic group, optionally containing 1-4 ring heteroatoms selected independently from the group consisting of N, O, and S; and
$R_6$ is selected from the group consisting of H or $C_1$-$C_3$ alkyl; where all cycloalkyl and cycloalkenyl optionally contain one or two ring heteroatoms selected independently from N, O, and S;

wherein all alkyl, cycloalkyl, alkenyl, cycloalkenyl, heterocycloalkyl, heterocycloalkenyl, alkynyl, aryl, and heteroaryl groups in $R_1$, $R_2$, R', $R_3$, $R_4$, $R_5$, $R_6$, and Ar are optionally substituted with one or two substituents selected independently from the group consisting of $C_1$-$C_3$ alkyl, halogen, OH, OEt, OMe, CN, $CH_2F$, $OCF_3$, and $CF_3$; and wherein, additionally, all cycloalkyl and heterocycloalkyl groups are optionally substituted with a carbonyl group.

2. The compound of claim 1, wherein:

$R_1$ and $R_2$, vary independently, and are selected from the group consisting of H, halogen, $CF_3$, $C_1$-$C_6$ alkyl, $C(=O)C_1$-$C_6$ alkyl, $C(=O)OC_1$-$C_6$ alkyl, $OC(=O)C_1$-$C_6$ alkyl, $OC_1$-$C_6$ alkyl, $SCH_3$, $C_3$-$C_6$ cycloalkyl, $(CH_2)_m C_3$-$C_6$ cycloalkyl, phenyl, pyridyl, pyrrolyl, thienyl, $(CH_2)_m$phenyl, $(CH_2)_m$pyrrolyl, and $(CH_2)_m$pyridyl;

wherein said cycloalkyl groups optionally contain one or two heteroatoms selected independently from the group consisting of O, N, and S;

wherein said alkyl, cycloalkyl, phenyl, pyrrolyl, and pyridyl groups are optionally substituted with one or two groups selected, independently, from halogen, methyl, ethyl, or trifluoromethyl; and wherein m is zero, 1, or 2;

R' is selected from the group consisting of H, halogen, phenyl, 2-(N,N-dimethylamino)ethyl, $CF_3$, $OC_1$-$C_3$ alkyl and $C_1$-$C_3$ alkyl;

$R_3$ and $R_4$ vary independently, and are selected from the group consisting of H, halogen, $CF_3$, $OCF_3$, $OC_1$-$C_3$ alkyl, and $C_1$-$C_3$ alkyl;

X is O or S;

Y is O or S;

q=1 or 0;

$R_5$ is selected from the group consisting of $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, Ar, $(CHR_6)_w$Ar, $CH_2(CHR_6)_w$Ar, and $(CHR_7)_w CH_2$Ar;

wherein w=0-3;

Ar is selected from the group consisting of phenyl, pyrimidyl, or pyridyl, and a 5-member heteroaromatic ring;

wherein said heteroaromatic ring contains 1 or 2 ring heteroatoms selected independently from the group consisting of N, O, and S; and $R_6$ is selected from the group consisting of H and methyl;

wherein all cycloalkyl and cycloalkenyl groups in $R_5$ optionally contain one or two ring heteroatoms selected independently from the group consisting of N, O, and S; and wherein all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, and Ar are optionally substituted with one or two substituents selected independently from the group consisting of $C_1$-$C_3$ alkyl, halogen, OEt, OMe, and trifluoromethyl.

3. The compound of claim 1, wherein:

$R_1$ and $R_2$, vary independently, and are selected from the group consisting of H, halogen, $CF_3$, $C_1$-$C_6$ alkyl, $C(=O)C_1$-$C_6$ alkyl, $C(=O)OC_1$-$C_6$ alkyl, $OC(=O)C_1$-$C_6$ alkyl, $OC_1$-$C_6$ alkyl, $SCH_3$, $(CH_2)_m$ cyclopropyl, $(CH_2)_m$cyclobutyl, $(CH_2)_m$ cyclopentyl, $(CH_2)_m$ cyclohexyl, $(CH_2)_m$oxazolyl, $(CH_2)_m$isoxazolyl, $(CH_2)_m$thiazolyl, $(CH_2)_m$isothiazolyl, $(CH_2)_m$phenyl, $(CH_2)_m$pyrrolyl, $(CH_2)_m$pyridyl, and $(CH_2)_m$pyrimidyl;

wherein said cyclopentyl and said cyclohexyl groups optionally contain one or two ring heteroatoms selected independently from the group consisting of O, N, and S;

wherein said alkyl, cycloalkyl, phenyl, pyrrolyl, and pyridyl groups are optionally substituted with one or two groups selected, independently, from the group consisting of halogen, $CH_3$, ethyl, and $CF_3$; and m is zero, 1, or 2;

R' is selected from the group consisting of H, halogen, $CF_3$, and $C_1$-$C_3$ alkyl;

$R_3$ and $R_4$ vary independently, and are selected from the group consisting of H, halogen, $CF_3$, $OCF_3$, $OC_1$-$C_3$ alkyl, and $C_1$-$C_3$ alkyl;

X is O or S;

Y is O;

q=1 or 0;

$R_5$ is selected from the group consisting of $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, $CR_6$=CH—$C_3$-$C_6$ cycloalkyl, CH=$CR_6$—$C_3$-$C_6$ cycloalkyl, $(CHR_6)_w C_5$-$C_6$ cycloalkenyl, $CH_2(CHR_6)_w C_5$-$C_6$ cycloalkenyl, $C_2$-$C_6$ alkenyl, $C_2$-$C_6$ alkynyl, Ar, $(CHR_6)_w$Ar, $CH_2(CHR_6)_w$Ar, and $(CHR_6)_w CH_2$Ar;

wherein w=0-3,

Ar is selected from the group consisting of phenyl, pyridyl, and a 5-member heteroaromatic ring, wherein said heteroaromatic ring contains 1 or 2 ring heteroatoms selected independently from the group consisting of N, O, and S;

$R_6$ is H or methyl;

wherein all cycloalkyl and cycloalkenyl groups optionally contain one or two ring heteroatoms selected independently from the group consisting of N, O, and S; and wherein all alkyl, cycloalkyl, alkenyl, cycloalkenyl, heterocycloalkyl, heterocycloalkenyl, alkynyl, aryl, and heteroaryl groups in $R_1$, $R_2$, $R_3$, $R_4$, $R_5$, $R_6$, and Ar are optionally substituted with one or two substituents selected independently from the group consisting of $C_1$-$C_3$ alkyl, halogen, OMe, OEt, and $CF_3$.

4. The compound of claim 2, wherein:

$R_1$ and $R_2$, vary independently, and are selected from the group consisting of H, halogen, $CF_3$, $OC_1$-$C_3$ alkyl, $C_1$-$C_6$ alkyl, $C(=O)OC_1$-$C_3$ alkyl, $OC(=O)C_1$-$C_3$ alkyl, and $C(=O)C_1$-$C_3$ alkyl;

R' is selected from the group consisting of H, F, $CH_3$, and ethyl;

$R_3$ and $R_4$ vary independently, and are selected from the group consisting of H, F, Cl, $CF_3$, $OCF_3$, $OC_1$-$C_3$ alkyl, and $C_1$-$C_3$ alkyl; and $R_5$ is $C_1$-$C_6$ alkyl, $(CHR_6)_w C_3$-$C_6$ cycloalkyl, $(CHR_6)_w CH_2 C_3$-$C_6$ cycloalkyl, $CH_2(CHR_6)_w C_3$-$C_6$ cycloalkyl, or $(CHR_6)_w$Ar, $CH_2(CHR_6)_w$Ar, or $(CHR_6)_w CH_2$Ar.

5. The compound of claim 1, wherein:

$R_2$ is H or F;

R' is H;

$R_3$ is selected from the group consisting of H, $CH_3$, $OCH_3$, $CF_3$, $OCF_3$, and Cl;

R$_4$ is selected from the group consisting of CH$_3$, OCH$_3$, CF$_3$, OCF$_3$, and Cl; and
R$_5$ is C$_3$-C$_6$ alkyl or (CH$_2$)$_w$C$_3$-C$_6$ cycloalkyl.

6. The compound of claim 1 or claim 2, wherein:
R$_1$ is halogen or CF$_3$;
R$_2$ is H or F;
R' is H;
R$_3$ and R$_4$ vary independently, and are selected from the group consisting of H, CH$_3$, OCH$_3$, CF$_3$, OCF$_3$, or Cl; and
R$_5$ is selected from the group consisting of C$_1$-C$_6$ alkyl, (CHR$_6$)$_w$C$_3$-C$_6$ cycloalkyl, (CHR$_6$)$_w$CH$_2$C$_3$-C$_6$ cycloalkyl, CH$_2$(CHR$_6$)$_w$C$_3$-C$_6$ cycloalkyl, CR$_6$=CH—C$_3$-C$_6$ cycloalkyl, CH=CR$_6$—C$_3$-C$_6$ cycloalkyl, (CHR$_6$)$_w$C$_5$-C$_6$ cycloalkenyl, CH$_2$(CHR$_6$)$_w$C$_5$-C$_6$ cycloalkenyl, C$_2$-C$_6$ alkenyl, C$_2$-C$_6$ alkynyl, Ar, (CHR$_6$)$_w$Ar, CH$_2$(CHR$_6$)$_w$Ar, and (CHR$_6$)$_w$CH$_2$Ar.

7. The compound of claim 1 which is a compound of formula IA-1

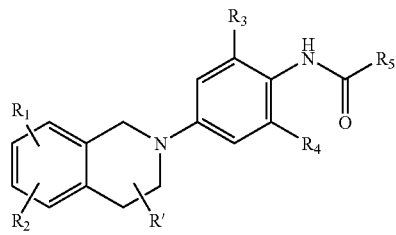

IA-1 wherein:
R$_1$ is selected from the group consisting of H, halogen, CN, CH$_2$CN, CF$_3$, C$_1$-C$_6$ alkyl, OCH$_3$, (C=O)OCH$_3$, O(C=O)CH$_3$, OCF$_3$, (CH$_2$)$_m$C$_3$-C$_6$ cycloalkyl, phenyl, and pyridyl;
R$_2$ is selected from the group consisting of H, F, OCH$_3$, CH$_3$, and CF$_3$;
R$_3$ and R$_4$ vary independently, and are selected from the group consisting of H, F, Cl, CF$_3$, OCF$_3$, OC$_1$-C$_3$ alkyl, or C$_1$-C$_3$ alkyl; and
R$_5$ is selected from the group consisting of C$_1$-C$_6$ alkyl, (CHR$_6$)$_w$C$_3$-C$_6$ cycloalkyl, (CHR$_6$)$_w$CH$_2$C$_3$-C$_6$ cycloalkyl, CH$_2$(CHR$_6$)$_w$C$_3$-C$_6$ cycloalkyl, CR$_6$=CH—C$_3$-C$_6$ cycloalkyl, CH=CR$_6$—C$_3$-C$_6$ cycloalkyl, (CHR$_6$)$_w$C$_5$-C$_6$ cycloalkenyl, CH$_2$(CHR$_6$)$_w$C$_5$-C$_6$ cycloalkenyl, C$_2$-C$_6$ alkenyl, C$_2$-C$_6$ alkynyl, Ar, (CHR$_6$)$_w$Ar, CH$_2$(CHR$_6$)$_w$Ar, and (CHR$_6$)$_w$CH$_2$Ar,
wherein w=0-3;
Ar is phenyl, furyl, pyrrolyl, oxazolyl, thiazolyl, thienyl, or pyridyl; and
R$_6$ is C$_1$-C$_3$ alkyl;
wherein all alkyl, cycloalkyl, aryl, and heteroaryl groups in R$_1$, R$_2$, R$_3$, R$_4$, R$_5$, R$_6$, and Ar are optionally substituted with one or two substituents selected independently from the group consisting of C$_1$-C$_3$ alkyl, halogen, OCH$_3$, OCH$_2$CH$_3$, CN, and CF$_3$.

8. The compound of claim 7, wherein:
R$_1$ is selected from the group consisting of H, F, Cl, Br, CF$_3$, C$_1$-C$_6$ alkyl, OCH$_3$, CH$_2$OCH$_3$, CH$_2$CH$_2$OCH$_3$, CH$_2$OCH$_2$CH$_3$, and OCH$_2$CH$_3$;
R' is selected from the group consisting of H, CH$_3$, CH$_2$CH$_3$, or halogen;
R$_3$ and R$_4$ vary independently, and are selected from the group consisting of H, F, Cl, CF$_3$, OCF$_3$, OCH$_3$, and CH$_3$; and R$_5$ is selected from the group consisting of C$_1$-C$_6$ alkyl, CH$_2$C$_3$-C$_6$ cycloalkyl, CH$_2$CH$_2$C$_3$-C$_6$ cycloalkyl, CH=CH—C$_3$-C$_6$ cycloalkyl, CH=CH—C$_5$-C$_6$ cycloalkenyl, CH$_2$C$_5$-C$_6$ cycloalkenyl, CH$_2$CH$_2$C$_5$-C$_6$ cycloalkenyl, C$_2$-C$_6$ alkenyl, and (CH$_2$)$_w$Ar;
wherein w=1 or 2;
Ar is selected from the group consisting of phenyl, oxazolyl, thiazolyl, isoxazolyl, isothiazolyl, furyl, thienyl, pyrrolyl, and pyridyl;
wherein all alkyl, cycloalkyl, aryl, and heteroaryl groups in R$_1$, R$_2$, R$_3$, R$_4$, R$_5$, R$_6$, and Ar are optionally substituted with one or two substituents selected independently from the group consisting of CH$_3$, halogen, OCH$_3$, OCH$_2$CH$_3$, CN, and CF$_3$.

9. The compound of claim 8, wherein:
R$_1$ is selected from the group consisting of F, CF$_3$, Cl, CH$_3$, CH$_2$CH$_3$, SCH$_3$, OCH$_3$, CH$_2$OCH$_3$, CH$_2$OCH$_2$CH$_3$, OCF$_3$, phenyl, thienyl, and H;
R$_2$ is selected from the group consisting of H, F, Cl, and OCH$_3$;
R' is selected from the group consisting of H, F, CH$_2$CH$_3$, and CH$_3$;
R$_3$ and R$_4$ vary independently, and are selected from the group consisting of H, Cl, CH$_3$, CF$_3$, OCH$_3$, and OCF$_3$; and
R$_5$ is selected from the group consisting of C$_4$-C$_6$ alkyl, (CH$_2$)$_w$Ar, and (CH$_2$)$_w$C$_5$-C$_6$ cycloalkyl;
wherein w is 1, 2, or 3.

10. The compound of claim 9, wherein:
R$_1$ is selected from the group consisting of F, CF$_3$, Cl, CH$_3$, OCH$_3$, CH$_2$OCH$_3$, and H;
R$_2$ is selected from the group consisting of H, F, CH$_3$, and Cl;
R' is H;
R$_3$ is selected from the group consisting of H, Cl, CH$_3$, CF$_3$, OCH$_3$, and OCF$_3$;
R$_4$ is selected from the group consisting of Cl, OCH$_3$, and CH$_3$; and
R$_5$ is C$_4$-C$_6$ alkyl or 2-cyclopentyl ethyl.

11. The compound of claim 10, wherein R$_3$ and R$_4$ are both CH$_3$ or both OCH$_3$; and R$_5$ is C$_5$-C$_6$ alkyl.

12. The compound of claim 3, wherein:
R' and R$_2$ are H;
R$_3$ and R$_4$ are both methyl; and
R$_5$ is C$_5$-C$_6$ alkyl or (CH$_2$)$_w$C$_5$-C$_6$ cycloalkyl;
wherein w is 1, 2, or 3.

13. A compound according to claim 1, wherein said compound is one of the following:
N-(2-chloro-4-(3,4-dihydroisoquinolin-2(1H)-yl)-6-(trifluoromethyl)phenyl)-3,3-dimethylbutanamide;
N-(4-(3,4-dihydroisoquinolin-2(1H)-yl)-2,6-dimethylphenyl)-3,3-dimethylbutanamide;
N-(2-chloro-4-(3,4-dihydroisoquinolin-2(1H)-yl)-6-(trifluoromethyl)phenyl)-3-cyclopentylpropanamide;
N-(2-chloro-4-(6-fluoro-3,4-dihydroisoquinolin-2(1H)-yl)-6-(trifluoromethylphenyl)-3,3-dimethylbutanamide;
N-[2-chloro-4-(3,4-dihydro-1H-isoquinolin-2-yl)-6-methyl phenyl]-3,3-dimethylbutanamide;
N-[2-chloro-4-(6-fluoro-3,4-dihydro-1H-isoquinolin-2-yl)-6-trifluoromethyl phenyl]-3-cyclopentylpropionamide;
N-[2,6-dimethyl-4-(6-trifluoromethyl-3,4-dihydro-1H-isoquinolin-2-yl)-phenyl]-3,3-dimethylbutanamide;
N-[2-chloro-6-trifluoromethyl-4-(6-trifluoromethyl-3,4-dihydro-1H-isoquinolin-2-yl)-phenyl]-3,3-dimethylbutanamide;

N-[2-chloro-4-(6-chloro-3,4-dihydro-1H-isoquinolin-2-yl)-6-trifluoromethyl phenyl]-3,3-dimethylbutanamide;
N-[4-(6-chloro-3,4-dihydro-1H-isoquinolin-2-yl)-2,6-dimethyl-phenyl]-3,3-dimethylbutanamide;
N-[4-(6-fluoro-3,4-dihydro-1H-isoquinolin-2-yl)-2,6-dimethyl phenyl]-3,3-dimethylbutanamide;
N-[2-chloro-4-(7-fluoro-3,4-dihydro-1H-isoquinolin-2-yl)-6-trifluoromethyl-phenyl]-3,3-dimethylbutanamide;
N-[4-(7-fluoro-3,4-dihydro-1H-isoquinolin-2-yl)-2,6-dimethyl-phenyl]-3,3-dimethylbutanamide;
N-[2-chloro-4-(6-fluoro-3,4-dihydro-1H-isoquinolin-2-yl)-6-methylphenyl]-3,3-dimethylbutanamide;
N-[2-chloro-4-(7-fluoro-3,4-dihydro-1H-isoquinolin-2-yl)-6-methylphenyl]-3,3-dimethylbutanamide;
N-[2-chloro-6-methyl-4-(6-trifluoromethyl-3,4-dihydro-1H-isoquinolin-2-yl)-phenyl]-3,3-dimethylbutanamide;
N-[2-chloro-4-(6-chloro-3,4-dihydro-1H-isoquinolin-2-yl)-6-methyl-phenyl]-3,3-dimethylbutanamide;
N-[2-chloro-4-(6-fluoro-3,4-dihydro-1H-isoquinolin-2-yl)-phenyl]-3,3-dimethylbutanamide;
N-[4-(6-fluoro-3,4-dihydro-1H-isoquinolin-2-yl)-2-methyl-phenyl]-3,3-dimethylbutanamide;
N-[4-(6-fluoro-3,4-dihydro-1H-isoquinolin-2-yl)-2-trifluoromethylphenyl]-3,3-dimethylbutanamide;
N-[2-chloro-4-(6-trifluoromethyl-3,4-dihydro-1H-isoquinolin-2-yl)-phenyl]-3,3-dimethylbutanamide;
N-[4-(7-fluoro-3,4-dihydro-1H-isoquinolin-2-yl)-2-trifluoromethyl-phenyl]-3,3-dimethylbutanamide;
3,3-dimethyl-N-[2-trifluoromethyl-4-(7-trifluoromethyl-3,4-dihydro-1H-isoquinolin-2-yl)-phenyl]butanamide;
N-[4-(6-methoxy-3,4-dihydro-1H-isoquinolin-2-yl)-2,6-dimethyl-phenyl]-3,3-dimethylbutanamide;
N-[4-(3,4-dihydro-1H-isoquinolin-2-yl)-2-methoxy-6-methyl-phenyl]-3,3-dimethylbutanamide;
N-[2-chloro-4-(3,4-dihydro-1H-isoquinolin-2-yl)-6-trifluoromethoxy-phenyl]-3,3-dimethylbutanamide;
N-[4-(3,4-dihydro-M-isoquinolin-2-yl)-2,6-dimethoxy-phenyl]-3,3-dimethylbutanamide;
N-[2,6-dimethyl-4-(7-trifluoromethyl-3,4-dihydro-1H-isoquinolin-2-yl)-phenyl]-3,3-dimethyl butanamide;
N-[2,6-Dimethyl-4-(6-trifluoromethyl-3,4-dihydro-1H-isoquinolin-2-yl)-phenyl]-3,3-dimethyl-thiobutanamide;
[2,6-Dimethyl-4-(6-trifluoromethyl-3,4-dihydro-1H-isoquinolin-2-yl)-phenyl]-carbamic acid ethyl ester; and
N-[2,6-Dimethyl-4-(7-trifluoromethyl-3,4-dihydro-1H-isoquinolin-2-yl)-phenyl]-3,3-dimethyl butanamide.

* * * * *